(12) United States Patent
Ohkawa et al.

(10) Patent No.: US 6,962,933 B1
(45) Date of Patent: Nov. 8, 2005

(54) METHOD FOR INHIBITING P38 MAP KINASE OR TNF-α PRODUCTION USING A 1,3-THIAZOLE

(75) Inventors: Shigenori Ohkawa, Takatsuki (JP); Kenichi Naruo, Sanda (JP); Hiroyuki Kimura, Sakai (JP); Seiji Miwatashi, Ikeda (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 11 days.

(21) Appl. No.: 10/048,937

(22) PCT Filed: Aug. 3, 2000

(86) PCT No.: PCT/JP00/05198

§ 371 (c)(1),
(2), (4) Date: Feb. 6, 2002

(87) PCT Pub. No.: WO01/10865

PCT Pub. Date: Feb. 15, 2001

(30) Foreign Application Priority Data

Aug. 6, 1999 (JP) ............................................ 11-224651

(51) Int. Cl.⁷ ................ A61K 31/4421; A61K 31/4436; C07D 417/04
(52) U.S. Cl. ..................... 514/340; 514/342; 546/270.4
(58) Field of Search .................................. 514/340, 342; 546/270.4

(56) References Cited

U.S. PATENT DOCUMENTS 4,612,321 A * 9/1986 Terao et al. ................. 514/338

FOREIGN PATENT DOCUMENTS

| | | |
|---|---|---|
| EP | 61425 | 9/1982 |
| EP | 149884 | 7/1985 |
| JP | 5-70446 | 3/1993 |
| JP | 11-49762 | 2/1999 |
| JP | 2000-302680 | 10/2000 |
| WO | 97/12876 | 4/1997 |
| WO | 99/21555 | * 5/1999 |
| WO | 99/21555 | 7/1999 |
| WO | 99/64418 | 12/1999 |
| WO | 00/49015 | 8/2000 |

* cited by examiner

*Primary Examiner*—Rita Desai
(74) *Attorney, Agent, or Firm*—Wenderoth, Lind & Ponack, L.L.P.

(57) ABSTRACT

A 1,3-thiazole compound substituted at the 5-position by a pyridyl group optionally having substituent(s) has a superior p38 MAP kinase inhibitory activity and TNF-α production inhibitory activity.

12 Claims, No Drawings

METHOD FOR INHIBITING P38 MAP KINASE OR TNF-α PRODUCTION USING A 1,3-THIAZOLE

This application is a 371 of PCT/JP00/05198 filed Aug. 3, 2000.

TECHNICAL FIELD

The present invention relates to superior p38 MAP kinase inhibitors, selective phosphodiesterase IV (PDE IV) inhibitors and the like. More particularly, the present invention relates to a pharmaceutical agent containing a 1,3-thiazole compound having a prophylactic or therapeutic activity of cytokine-mediated diseases, based on a p38 MAP kinase inhibitory activity, a TNF-α production inhibitory activity, a phosphodiesterase (PDE) inhibitory activity and the like.

BACKGROUND ART

Cytokines such as TNF-α (tumor necrosis factor-α), IL-1 (interleukin-1) and the like are biological substances which is are produced by a variety of cells such as monocyte or macrophage in response to the infection and other cellular stress (Koj, A., Biochim. Biophys. Acta, 1317, 84–94 (1996)). Although these cytokines play important roles in the immune response when they are present at an appropriate amount, it is thought that the overproduction is associated with a variety of inflammatory diseases (Dinarello, C. A., Curr. Opin. Immunol., 3, 941–948 (1991)). p38 MAP kinase which was cloned as a homologue of MAP kinase is involved in the control of production of these cytokines and signal transduction system coupled with receptors, and there is a possibility that the inhibition of p38 MAP kinase provides a drug for treating inflammatory diseases (Stein, B., Anderson, D., Annual Report in Medicinal Chemistry, edited by Bristol, J. A., Academic Press, vol. 31, pages 289–298, 1996).

As compounds having a p38 MAP kinase inhibitory activity, imidazole derivatives are described in JP-T 7-50317 (WO 93/14081) and oxazole derivatives are described in JP-T 9-505055 (WO 95/13067), respectively.

On the other hand, as thiazole compounds, the following compounds are known:
1) 1,3-thiazole derivatives represented by the formula:

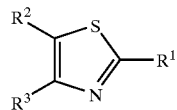

wherein $R^1$ represents a cycloalkyl group, a cyclic amino group, an amino group optionally having, as substituent(s), 1 or 2 lower alkyl, phenyl, acetyl or lower alkoxycarbonylacetyl, an alkyl group optionally having, as substituent(s), hydroxyl, carboxyl or lower alkoxycarbonyl, or a phenyl group optionally having, as substituent(s), carboxyl, 2-carboxyethenyl or 2-carboxy-1-propenyl, $R^2$ represents a pyridyl group optionally having, as substituent(s), lower alkyl, $R^3$ represents a phenyl group optionally having, as substituent(s), lower alkoxy, lower alkyl, hydroxyl, halogen or methylenedioxy, or salts thereof, which have analgesic, antipyretic, anti-inflammatory, anti-ulcerative, thromboxane $A_2$ ($TXA_2$) synthase-inhibitory, and is platelet coagulation-inhibitory activities (JP-A 60-58981),
2) 1,3-thiazole derivatives represented by the formula:

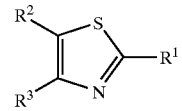

wherein $R^1$ represents an alkyl group, an alkenyl group, an aryl group, an aralkyl group, a cycloalkyl group, a heterocyclic group employing carbon as an attachment point or an amino group optionally having substituent(s), $R^2$ represents a pyridyl group optionally substituted with alkyl group(s), $R^3$ represents a phenyl group optionally having substituent(s), or salts thereof, which have analgesic, antipyretic, anti-inflammatory, anti-ulcerative, $TXA_2$ synthase-inhibitory, and platelet coagulation-inhibitory activities (JP-A 61-10580),
3) 1,3-thiazole derivatives represented by the formula:

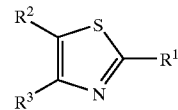

wherein $R^1$ represents an alkyl group, an alkenyl group, an aryl group, an aralkyl group, a cycloalkyl group, a heterocyclic group employing carbon as an attachment point or an amino group optionally having substituent(s), $R^2$ represents a pyridyl group optionally substituted with alkyl group(s), $R^3$ represents an aryl group optionally having substituent(s), or salts thereof, which have analgesic, antipyretic, anti-inflammatory, anti-ulcerative, $TXA_2$ synthase-inhibitory, and platelet coagulation-inhibitory activities (U.S. Pat. No. 4,612,321),
4) a compound of the formula

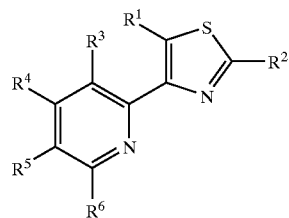

wherein $R^1$ represents an optionally substituted phenyl, $R^2$ represents $C_{1-6}$ alkyl or $(CH_2)_nAr$, n represents 0–2, Ar represents an optionally substituted phenyl, $R^3$ represents a hydrogen or $C_{1-4}$alkyl, $R^4$ represents a hydrogen, $C_{1-4}$ alkyl and the like, $R^5$ represents a hydrogen or $C_{1-4}$ alkyl, $R^6$ represents a hydrogen, $C_{1-4}$ alkyl and the like, or a salt thereof, having an inhibitory activity of gastric acid secretion (JP-T 7-503023, WO93/15071),
5) a compound of the formula

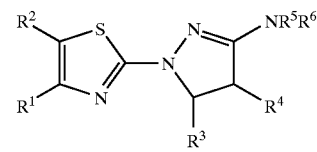

wherein $R^1$ represents pyridyl and the like, $R^2$ represents phenyl and the like, $R^3$ and $R^4$ represent a hydrogen or methyl, $R^5$ represents methyl and the like, and $R^6$ represents a hydrogen, methyl and the like, or a salt thereof, which is an antiinflammatory agent and antiallergic agent (DE-A-3601411);

6) a compound of the formula

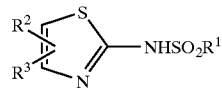

wherein $R^1$ represents a lower alkyl substituted by halogen, $R^2$ represents pyridyl and the like, and $R^3$ represents phenyl and the like, or a salt thereof, having an antiinflammatory, antipyretic, analgesic and antiallergic activity (JP-A-5-70446), and 7) a thiazole compound of the formula

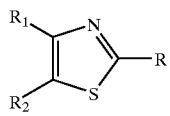

wherein R represents a lower alkyl group; a lower haloalkyl group; a lower hydroxyalkyl group; a lower alkoxy(lower)alkyl group; an aralkyloxy(lower)alkyl group and the like, $R^1$ represents a cycloalkyl group optionally substituted by lower alkyl group(s) and the like, and $R^2$ represents an optionally substituted aryl group and the like, or a pharmaceutically acceptable salt thereof, having a selective inhibitory activity of TNF-α production and/or IFN-γ production (JP-A-11-49762).

In as much as a p38 MAP kinase inhibitor, TNF-α production inhibitor or PDE IV inhibitor satisfactory in the action effect, safety, metabolism stability and the like has not been found yet, the development of a p38 MAP kinase inhibitor, TNF-α production inhibitor or PDE IV inhibitor having superior property as a pharmaceutical agent effective for the prophylaxis or treatment of cytokine-mediated diseases and the like has been demanded.

DISCLOSURE OF THE INVENTION

The present inventors studied variously and, as a result, have first found that a 1,3-thiazole compound (hereinafter sometimes to be briefly referred to as Compound (I)) characterized by a chemical structure where the 1,3-thiazole structure is substituted at the 5-position by a pyridyl group optionally having substituent(s) includes, for example, a compound of the formula (Ia)

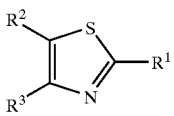

wherein
$R^1$ represents a hydrogen atom, a hydrocarbon group optionally having substituent(s), a heterocyclic group optionally having substituent(s), an amino group optionally having substituent(s) or an acyl group;
$R^2$ represents a pyridyl group optionally having substituent(s); and
$R^3$ represents an aromatic group optionally having substituent(s), and a salt thereof [hereinafter sometimes to be briefly referred to as Compound (Ia)], and that they have, based on their specific chemical structure, an unexpectedly superior p38 MAP kinase-inhibitory activity, a TNF-α production-inhibitory activity, a PDE IV-inhibitory activity and the like, as well as superior properties as a pharmaceutical product, such as stability and the like, and are sufficiently satisfactory as a pharmaceutical, and completed the present invention based on these findings.

Accordingly, the present invention relates to (1) a p38 MAP kinase inhibitory agent comprising a 1,3-thiazole compound substituted at the 5-position by a pyridyl group optionally having substituent(s), a salt thereof or a prodrug thereof, (2) a TNF-α production inhibitory agent comprising a 1,3-thiazole compound substituted at the 5-position by a pyridyl group optionally having substituent(s), a salt thereof or a prodrug thereof, excluding a compound of the formula

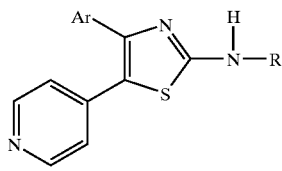

wherein Ar is an unsubstituted or substituted aryl group bonded to a thiazole ring by a carbon atom of an aromatic ring, and R is a hydrogen atom, an acyl group, or a monovalent aromatic group having not more than 10 carbon atoms, which is bonded to a nitrogen atom by a carbon atom of the aromatic ring, and a salt thereof, (3) the agent of (1) or (2), wherein the 1,3-thiazole compound is a 1,3-thiazole compound substituted at the 4-position by an aromatic group optionally having substituent(s), (4) the agent of (1) or (2), wherein the 1,3-thiazole compound is a 1,3-thiazole compound substituted at the 2-position by an aryl group optionally having substituent(s) or an amino group optionally having substituent(s), (5) the agent of (1) or (2), wherein the 1,3-thiazole compound is a compound of the formula

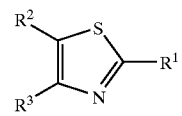

wherein $R^1$ represents a hydrogen atom, a hydrocarbon group optionally having substituent(s), a heterocyclic group optionally having substituent(s), an amino group optionally having substituent(s) or an acyl group;
$R^2$ represents a pyridyl group optionally having substituent(s); and
$R^3$ represents an aromatic group optionally having substituent(s), or a salt thereof, (6) the agent of (1) or (2), which is a prophylactic or therapeutic agent of cytokine-mediated diseases, (7) the compound of (5), wherein $R^1$ is
(i) a hydrogen atom,
(ii) a $C_{1-10}$ alkyl group, a $C_{2-6}$ alkenyl group, a $C_{2-6}$ alkynyl group, a $C_{3-6}$ alkcycloalkyl group, a $C_{6-14}$ aryl group or a $C_{7-16}$ aralkyl group [these groups may have substituent(s) selected from the group (substituent group A) consisting of oxo, halogen atom, $C_{1-3}$ alkylenedioxy, nitro, cyano, optionally halogenated $C_{1-6}$ alkyl, optionally halogenated $C_{2-6}$ alkenyl, carboxy $C_{2-6}$ alkenyl, optionally halogenated $C_{2-6}$ alkynyl, optionally halogenated $C_{3-6}$ alkcycloalkyl, $C_{6-14}$ aryl, optionally halogenated $C_{1-8}$ alkoxy, $C_{1-6}$ alkoxy-carbonyl-$C_{1-6}$ alkoxy, hydroxy, $C_{6-14}$ aryloxy, $C_{7-16}$ aralkyloxy, mercapto, optionally halogenated $C_{1-6}$ alkylthio, $C_{6-14}$ arylthio, $C_{7-16}$ aralkylthio, amino, mono-$C_{1-6}$ alkylamino, mono-$C_{6-14}$ arylamino, di-$C_{1-6}$ alkylamino, di-$C_{6-14}$ arylamino, formyl, carboxy, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5 or 6 membered heterocyclic carbonyl, carbamoyl, thiocarbamoyl, mono-$C_{1-6}$ alkyl-carbamoyl, di-$C_{1-6}$ alkyl-carbamoyl, $C_{6-14}$ aryl-carbamoyl, 5 or 6 membered heterocyclic carbamoyl, $C_{1-6}$ alkylsulfonyl, $C_{6-14}$ arylsulfonyl, $C_{1-6}$ alkylsulfinyl, $C_{6-14}$ arylsulfinyl, formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino, $C_{6-14}$ arylsulfonylamino, $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy, nicotinoyloxy, 5 to 7 membered saturated cyclic amino optionally having 1 to 4 of one or two kinds of heteroatom(s) selected from a nitrogen atom, a sulfur atom and an oxygen atom in addition to one nitrogen atom and carbon atoms (this cyclic amino may have substituents selected from the group consisting of $C_{1-6}$ alkyl, $C_{6-14}$ aryl, $C_{1-6}$ alkyl-carbonyl, 5 to 10 membered aromatic heterocyclic group and oxo), 5 to 10 membered aromatic heterocyclic group containing 1 to 4 of one or two kinds of heteroatom(s) selected from a nitrogen atom, a sulfur atom and an oxygen atom, in addition to carbon atoms, sulfo, sulfamoyl, sulfinamoyl and sulfenamoyl], (iii) a monovalent heterocyclic group obtained by removing one arbitrary hydrogen atom from a 5 to 14 membered heterocycle containing 1 to 4 of one or two kinds of heteroatom(s) selected from a nitrogen atom, a sulfur atom and an oxygen atom in addition to carbon atoms optionally having substituents selected from the above-mentioned substituent group A, (iv) an acyl group represented by the formula:

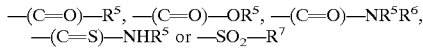

wherein $R^5$ represents (a) a hydrogen atom, (b) a $C_{1-6}$ alkyl group, a $C_{2-6}$ alkenyl group, a $C_{2-6}$ alkynyl group, a $C_{3-6}$ cycloalkyl group, a $C_{6-14}$ aryl group or a $C_{7-16}$ aralkyl group as defined in the above (ii) or (c) a heterocyclic group as defined in the above (iii), $R^6$ represents a hydrogen atom or a $C_{1-6}$ alkyl group, $R^7$ represents (a) a $C_{1-6}$ alkyl group, a $C_{2-6}$ alkenyl group, a $C_{2-6}$ alkynyl group, a $C_{3-6}$ alkcycloalkyl group, a $C_{6-14}$ aryl group or a $C_{7-16}$ aralkyl group as defined in the above (ii), or (b) a heterocyclic group as defined in the above (iii), (v) an amino group (this amino group may have substituent(s) selected from the group consisting of (a) a $C_{1-6}$ alkyl group, a $C_{2-6}$ alkenyl group, a $C_{2-6}$ alkynyl group, a $C_{3-6}$ cycloalkyl group, a $C_{6-14}$ aryl group or a $C_{7-16}$ aralkyl group as defined in the above (ii), (b) a heterocyclic group as defined in the above (iii), (c) an acyl group as defined in the above (iv), and (d) a $C_{1-6}$ alkylidene group optionally having substituent(s) selected from the above substituent group A), or (vi) a 5 to 7 membered non-aromatic cyclic amino group optionally containing 1 to 4 of one or two kinds of heteroatom(s) selected from a nitrogen atom, a sulfur atom and an oxygen atom in addition to one nitrogen atom and carbon atoms (this cyclic amino group-may have substituent(s) selected from the group consisting of $C_{1-6}$ alkyl, $C_{6-14}$ aryl, $C_{1-6}$ alkyl-carbonyl, 5 to 10 membered aromatic heterocyclic group and oxo);

$R^2$ represents a pyridyl group optionally having substituent(s) selected from the above substituent group A; and $R^3$ represents (a) a $C_{6-14}$ monocyclic or fused polycyclic aromatic hydrocarbon group optionally having substituents selected from the substituent group A or (b) a monovalent aromatic heterocyclic group obtained by removing one arbitrary hydrogen atom from a 5 to 14 membered aromatic heterocycle containing 1 to 4 of one or two kinds of heteroatom(s) selected from a nitrogen atom, a sulfur atom and an oxygen atom in addition to carbon atoms, said 5 to 14 membered aromatic heterocycle optionally having substituent(s) selected from the substituent group A, (8) the agent of (5), wherein $R^1$ is (a) a $C_{6-14}$ aryl group (preferably $C_{6-10}$ aryl) optionally having 1 to 5 substituent(s) selected from halogen atom, optionally halogenated $C_{1-6}$ alkyl, carboxy $C_{2-6}$ alkenyl, optionally halogenated $C_{1-6}$ alkoxy, $C_{1-6}$ alkoxy-carbonyl-$C_{1-6}$ alkoxy, hydroxy, amino, mono- or di-$C_{1-6}$ alkylamino, carboxy, $C_{1-6}$ alkoxy-carbonyl, mono- or di-$C_{1-6}$ alkyl-carbamoyl, $C_{6-14}$ aryl-carbonylamino, $C_{1-3}$ alkylenedioxy, $C_{1-6}$ alkylthio, $C_{6-14}$ arylthio, $C_{1-6}$ alkylsulfinyl, $C_{6-14}$ arylsulfinyl, $C_{1-6}$ alkylsulfonyl, $C_{6-14}$ arylsulfonyl and nitro, (b) a $C_{1-8}$ alkyl group optionally having 1 to 5 substituent(s) selected from halogen atom, optionally halogenated $C_{1-6}$ alkyl, carboxy $C_{2-6}$ alkenyl, optionally halogenated $C_{1-6}$ alkoxy, $C_{1-6}$ alkoxy-carbonyl-$C_{1-6}$ alkoxy, hydroxy, amino, mono- or di-$C_{1-6}$ alkylamino, carboxy, $C_{1-6}$ alkoxy-carbonyl, mono- or di-$C_{1-6}$ alkyl-carbamoyl and $C_{6-14}$ aryl-carbonylamino, (c) a $C_{3-6}$ cycloalkyl group (e.g., cyclohexyl) optionally having 1 to 5 substituent(s) selected from halogen atom, optionally halogenated $C_{1-6}$ alkyl, carboxy $C_{2-6}$ alkenyl, optionally halogenated $C_{1-6}$ alkoxy, $C_{1-6}$ alkoxy-carbonyl-$C_{1-6}$ alkoxy, hydroxy, amino, mono- or di-$C_{1-6}$ alkylamino, carboxy, $C_{1-6}$ alkoxy-carbonyl, mono- or di-$C_{1-6}$ alkyl-carbamoyl and $C_{6-14}$ aryl-carbonylamino, (d) a $C_{7-16}$ aralkyl group (e.g., phenyl-$C_{1-6}$ alkyl group), (e) a 5 to 10 membered aromatic heterocyclic group containing 1 to 4 of one or two kinds of heteroatom(s) selected from a nitrogen atom, a sulfur atom and an oxygen atom in addition to carbon atoms (e.g., 5 or 6 membered aromatic heterocyclic group such as pyridyl, thienyl and the like), (f) a 5 to 10 membered non-aromatic heterocyclic group containing 1 or 2 of one or two kinds of heteroatom(s) selected from a nitrogen atom, a sulfur atom and an oxygen atom in addition to carbon atoms, said 5 to 14 membered aromatic heterocycle optionally having $C_{6-14}$ aryl (e.g., phenyl), $C_{1-6}$ alkyl-carbonyl or oxo (e.g., 5 or 6 membered non-aromatic cyclic amino group such as piperidino, piperazino and the like), (g) an amino group optionally having 1 or 2 substituent(s) selected from the group consisting of the following (1) to (7) [(1) $C_{1-6}$ alkyl, (2) $C_{6-14}$ aryl, (3) $C_{7-16}$ aralkyl, (4) 5 or 6 membered heterocyclic group containing 1 or 2 heteroatom(s) selected from a nitrogen atom, a sulfur atom and an oxygen atom in addition to carbon atoms (e.g., pyridyl), (5) $C_{1-6}$ alkyl-carbonyl, $C_{3-6}$ cycloalkyl-carbonyl, $C_{6-14}$ aryl-carbonyl, $C_{7-16}$ aralkyl-carbonyl, $C_{1-6}$ alkyl-carbamoyl or 5 or 6 membered heterocyclic carbonyl group, optionally having 1 to 3 substituent(s) selected from halogen atom, $C_{1-6}$ alkyl, $C_{1-6}$ alkoxy, carboxy, $C_{1-6}$ alkoxy-carbonyl, cyano, tetrazine and the like, (6) $C_{6-14}$ aryl-carbamoyl group optionally having 1 to 3 substituent(s) selected from halogen atom, $C_{1-6}$ alkyl, $C_{1-6}$ alkoxy, carboxy, $C_{1-6}$ alkoxy-carbonyl, cyano, nitro, mono- or di-$C_{1-6}$ alkylamino and the like and (7) di-$C_{1-6}$ alkylamino-$C_{1-6}$ alkylidene], or (h) a carboxy group, (9) the agent of (5), wherein $R^1$ is a $C_{6-14}$ aryl group optionally having $C_{1-6}$ alkylsulfonyl,

(10) the agent of (5), wherein $R^2$ is a 4-pyridyl group optionally having substituent(s),

(11) the agent of (5), wherein $R^3$ is a $C_{6-10}$ aryl group optionally having substituent(s),

(12) the agent of (5), wherein $R^3$ is a phenyl group optionally having substituent(s),

(13) the agent of (5), wherein $R^3$ is a $C_{6-14}$ aryl group optionally having substituent(s) selected from the group consisting of halogen atom, $C_{1-3}$ alkylenedioxy, optionally halogenated $C_{1-6}$ alkyl, carboxy $C_{2-6}$ alkenyl, optionally halogenated $C_{1-8}$ alkoxy, carboxy $C_{1-8}$ alkoxy, hydroxy, $C_{1-14}$ aryloxy, $C_{1-6}$ alkoxy-carbonyl, $C_{1-6}$ alkyl-carbonyloxy, mono- or di-$C_{1-6}$ alkylamino and $C_{1-6}$ alkoxy-carbonyl-$C_{1-6}$ alkoxy,

(14) the agent of (5), wherein $R^3$ is a phenyl group optionally having substituent(s) selected from the group consisting of halogen atom and $C_{1-6}$ alkyl group,

(15) the agent of (5), wherein $R^1$ is (a) an amino group optionally having 1 or 2 acyl represented by the formula: —(C=O)—$R^5$ or —(C=O)—$NR^5R^6$ wherein each symbol is as defined above, (b) $C_{6-14}$ aryl group optionally having 1 to 5 substituent(s) selected from $C_{1-6}$ alkylthio, $C_{6-14}$ arylthio, $C_{1-6}$ alkylsulfinyl, $C_{6-14}$ arylsulfinyl, $C_{1-6}$ alkylsulfonyl, $C_{6-14}$ arylsulfonyl and carboxy or (c) $C_{1-6}$ alkyl group optionally substituted by halogen atom, $R^2$ is a pyridyl group, and $R^3$ is a $C_{6-14}$ aryl group optionally having 1 to 5 substituent(s) selected from halogen atom, optionally halogenated $C_{1-6}$ alkyl, optionally halogenated $C_{1-6}$ alkoxy and carboxy,

(16) the agent of (5), wherein $R^1$ is (i) $C_{1-8}$ alkyl, $C_{3-6}$ cycloalkyl or $C_{6-14}$ aryl optionally having 1 to 5 substituent(s) selected from halogen atom, optionally halogenated $C_{1-6}$ alkyl, carboxy $C_{2-6}$ alkenyl, optionally halogenated $C_{1-6}$ alkoxy, $C_{1-6}$ alkoxy-carbonyl-$C_{1-6}$ alkoxy, hydroxy, amino, mono- or di-$C_{1-6}$ alkylamino, carboxy, $C_{1-6}$ alkoxy-carbonyl, mono- or di-$C_{1-6}$ alkyl-carbamoyl and $C_{6-14}$ aryl-carbonylamino, (ii) a 5 membered heterocyclic group, (iii) an amino group optionally having 1 or 2 substituent(s) selected from (a) $C_{1-6}$ alkyl, (b) $C_{6-14}$ aryl, (c) $C_{7-16}$ aralkyl, (d) 6 membered heterocyclic group and (e) $C_{1-6}$ alkyl-carbonyl, $C_{3-6}$ cycloalkyl-carbonyl, $C_{6-14}$ aryl-carbonyl, $C_{7-16}$ aralkyl-carbonyl, $C_{1-6}$ alkyl-carbamoyl or 5 or 6 membered heterocyclic carbonyl, optionally having 1 to 3 substituent(s) selected from halogen atom, $C_{1-6}$ alkyl, $C_{1-6}$ alkoxy, carboxy and $C_{1-6}$ alkoxy-carbonyl, or an amino group optionally having di-$C_{1-6}$ alkylamino-$C_{1-6}$ alkylidene, (iv) a 5 or 6 membered non-aromatic cyclic amino group optionally substituted by $C_{1-6}$ alkyl-carbonyl or oxo, or (v) a carboxy group; and $R^2$ is a pyridyl group; and $R^3$ is a $C_{6-10}$ aryl group optionally having 1 to 3 substituent(s) selected from halogen atom, $C_{1-3}$ alkylenedioxy, optionally halogenated $C_{1-6}$ alkyl, carboxy $C_{2-6}$ alkenyl, optionally halogenated $C_{1-8}$ alkoxy, hydroxy, $C_{7-16}$ aralkyloxy and $C_{1-6}$ alkyl-carbonyloxy (two adjacent alkyl groups as substituents may be bonded to form a 5 membered non-aromatic carbon ring),

(17) the agent of (5), wherein $R^1$ is a $C_{6-15}$ aryl group optionally having $C_{1-6}$ alkylsulfonyl, $R^2$ is a pyridyl group, and $R^3$ is a $C_{6-14}$ aryl group optionally having halogen atom(s),

(18) the agent of (1) or (2), which is a prophylactic or therapeutic agent of asthma, chronic obstructive pulmonary disease (COPD), allergic disease (e.g., allergic dermatitis, allergic rhinitis), inflammation, Addison's disease, autoimmune hemolytic anemia, systemic lupus erythematosus, Crohn's disease, psoriasis, rheumatism, cerebral hemorrhage, cerebral infarction, head trauma, spinal cord injury, brain edema, multiple sclerosis, Alzheimer's disease, Parkinson's disease, amyotrophic lateral sclerosis, diabetes, arthritis (e.g., chronic rheumatoid arthritis, osteoarthritis), osteoporosis, toxemia (e.g., sepsis), Crohn's disease, ulcerative colitis, chronic pneumonia, pulmonary silicosis, pulmonary sarcoidosis, pulmonary tuberculosis, cachexia, arteriosclerosis, Creutzfeldt-Jakob disease, virus infection, atopic dermatitis, AIDS encephalopathy, meningitis, angina pectoris, cardiac infarction, congestive heart failure, hepatitis, kidney failure, nephritis, malignant tumor, transplantation, dialysis hypotension or disseminated intravascular coagulation,

(19) the agent of (1) or (2), which is a prophylactic or therapeutic agent of chronic rheumatoid arthritis or osteoarthritis,

(20) N-ethyl-[4-(4-methoxyphenyl)-5-(4-pyridyl)-1,3-thiazol-2-yl]amine (Reference Example 23-269), N-propyl-[4-(3,5-dimethylphenyl)-5-(4-pyridyl)-1,3-thiazol-2-yl]amine (Reference Example 23-276), N-butyl-[4-(3,5-dimethylphenyl)-5-(4-pyridyl)-1,3-thiazol-2-yl]amine (Reference Example 23-280), N-benzyl-[4-(3,5-dimethylphenyl)-5-(4-pyridyl)-1,3-thiazol-2-yl]amine (Reference Example 23-281), N-propyl-[4-(4-methoxyphenyl)-5-(4-pyridyl)-1,3-thiazol-2-yl]amine (Reference Example 23-290), N-isopropyl-[4-(4-methoxyphenyl)-5-(4-pyridyl)-1,3-thiazol-2-yl]amine (Reference Example 23-291), N-[4-(4-methoxyphenyl)-5-(4-pyridyl)-1,3-thiazol-2-yl]-N'-phenylurea (Reference Example 23-296), 4-[[[4-(4-methoxyphenyl)-5-(4-pyridyl)-1,3-thiazol-2-yl]amino]carbonyl]benzoic acid (Reference Example 23-299), methyl 4-[2-[4-(methylthio)phenyl]-5-(4-pyridyl)-1,3-thiazol-4-yl]phenyl ether (Reference Example 23-300), 4-[4-(3,5-dimethylphenyl)-5-(4-pyridyl)-1,3-thiazol-2-yl]phenylmethylsulfide (Reference Example 23-302), 4-[4-(4-methoxyphenyl)-5-(4-pyridyl)-1,3-thiazol-2-yl]phenylmethylsulfoxide (Reference Example 23-303), 4-[4-(3,5-dimethylphenyl)-5-(4-pyridyl)-1,3-thiazol-2-yl]phenylmethylsulfoxide (Reference Example 23-305), 4-[4-(4-methoxyphenyl)-5-(4-pyridyl)-1,3-thiazol-2-yl]phenylmethylsulfone (Reference Example 23-306), 4-[4-(3,5-dimethylphenyl)-5-(4-pyridyl)-1,3-thiazol-2-yl]phenylmethylsulfone (Reference Example 23-308), 4-[4-(4-fluorophenyl)-5-(4-pyridyl)-1,3-thiazol-2-yl]
  phenylmethylsulfide (Reference Example 23-309),
4-[4-(4-chlorophenyl)-5-(4-pyridyl)-1,3-thiazol-2-yl]
  phenylmethylsulfide (Reference Example 23-310),
4-[4-(4-fluorophenyl)-5-(4-pyridyl)-1,3-thiazol-2-yl]
  phenylmethylsulfoxide (Reference Example 23-311),
4-[4-(4-chlorophenyl)-5-(4-pyridyl)-1,3-thiazol-2-yl]
  phenylmethylsulfoxide (Reference Example 23-312),
4-[4-(4-fluorophenyl)-5-(4-pyridyl)-1,3-thiazol-2-yl]
  phenylmethylsulfone (Reference Example 23-313),
4-[4-(4-chlorophenyl)-5-(4-pyridyl)-1,3-thiazol-2-yl]
  phenylmethylsulfone (Reference Example 23-314),
N-[4-(3,5-dimethylphenyl)-5-(4-pyridyl)-1,3-thiazol-2-yl]-
  N'-phenylurea (Reference Example 23-315),
2-hydroxy-N-[4-(4-methoxyphenyl)-5-(4-pyridyl)-1,3-
  thiazol-2-yl]propionamide (Reference Example 23-325),
4-[4-(3,4-dimethylphenyl)-5-(4-pyridyl)-1,3-thiazol-2-yl]
  phenylmethylsulfide (Reference Example 23-326),
4-[4-(3,4-dimethylphenyl)-5-(4-pyridyl)-1,3-thiazol-2-yl]
  phenylmethylsulfoxide (Reference Example 23-327),
4-[4-(3,4-dimethylphenyl)-5-(4-pyridyl)-1,3-thiazol-2-yl]
  phenylmethylsulfone (Reference Example 23-328),
2-hydroxy-N-[4-(4-methoxyphenyl)-5-(4-pyridyl)-1,3-
  thiazol-2-yl]acetamide (Reference Example 23-329),
4-[[[4-(3,5-dimethylphenyl)-5-(4-pyridyl)-1,3-thiazol-2-yl]
  amino]carbonyl]benzoic acid (Reference Example
  23-337),
3-[[[4-(3,5-dimethylphenyl)-5-(4-pyridyl)-1,3-thiazol-2-yl]
  amino]carbonyl]benzoic acid (Reference Example
  23-342),
4-(4-fluorophenyl)-2-phenyl-5-(4-pyridyl)-1,3-thiazole
  (Reference Example 44-1),
methyl 4-[4-(3-methylphenyl)-5-(4-pyridyl)-1,3-thiazol-2-
  yl]phenylsulfide (Reference Example 44-7),
methyl 4-[4-(3-methylphenyl)-5-(4-pyridyl)-1,3-thiazol-2-
  yl]phenylsulfoxide (Reference Example 44-8),
methyl 4-[4-(3-methylphenyl)-5-(4-pyridyl)-1,3-thiazol-2-
  yl]phenylsulfone (Reference Example 44-26), or a salt
  thereof,
(21) a method for inhibiting p38 MAP kinase, comprising
  administering an effective amount of a 1,3-thiazole compound substituted at the 5-position by a pyridyl group
  optionally having substituent(s), a salt thereof or a prodrug thereof to a mammal,
(22) a method for inhibiting TNF-α production, comprising
  administering an effective amount of a 1,3-thiazole compound substituted at the 5-position by a pyridyl group
  optionally having substituent(s), a salt thereof or a prodrug thereof, excluding a compound of the formula

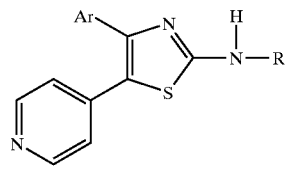

wherein Ar is an unsubstituted or substituted aryl group
  bonded to a thiazole ring by a carbon atom of an aromatic
  ring, and R is a hydrogen atom, an acyl group, or a
  monovalent aromatic group having not more than 10 carbon
  atoms, which is bonded to a nitrogen atom by a carbon atom
  of the aromatic ring, and a salt thereof, to a mammal,
(23) a method for prophylaxis or treatment of asthma,
  chronic obstructive pulmonary disease (COPD), allergic
  disease (e.g., allergic dermatitis, allergic rhinitis),
  inflammation, Addison's disease, autoimmune hemolytic
  anemia, systemic lupus erythematosus, Crohn's disease,
  psoriasis, rheumatism, cerebral hemorrhage, cerebral
  infarction, head trauma, spinal cord injury, brain edema,
  multiple sclerosis, Alzheimer's disease, Parkinson's
  disease, amyotrophic lateral sclerosis, diabetes, arthritis
  (e.g., chronic rheumatoid arthritis, osteoarthritis),
  osteoporosis, toxemia (e.g., sepsis), Crohn's disease,
  ulcerative colitis, chronic pneumonia, pulmonary
  silicosis, pulmonary sarcoidosis, pulmonary tuberculosis,
  cachexia, arteriosclerosis, Creutzfeldt-Jakob disease,
  virus infection, atopic dermatitis, AIDS encephalopathy,
  meningitis, angina pectoris, cardiac infarction, congestive
  heart failure, hepatitis, kidney failure, nephritis, malignant tumor, transplantation, dialysis hypotension or disseminated intravascular coagulation, which method comprises administering an effective amount of a 1,3-thiazole
  compound substituted at the 5-position by a pyridyl group
  optionally having substituent(s), a salt thereof or a prodrug thereof to a mammal,
(24) a method for prophylaxis or treatment of chronic
  rheumatoid arthritis or osteoarthritis, which method comprises administering an effective amount of a 1,3-thiazole
  compound substituted at the 5-position by a pyridyl group
  optionally having substituent(s), a salt thereof or a prodrug thereof to a mammal,
(25) use of a 1,3-thiazole compound substituted at the
  5-position by a pyridyl group optionally having
  substituent(s), a salt thereof or a prodrug thereof for the
  production of a p38 MAP kinase inhibitory agent,
(26) use of a 1,3-thiazole compound substituted at the
  5-position by a pyridyl group optionally having
  substituent(s), a salt thereof or a prodrug thereof, excluding a compound of the formula

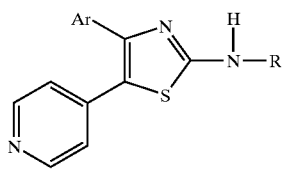

wherein Ar is an unsubstituted or substituted aryl group
  bonded to a thiazole ring by a carbon atom of an aromatic
  ring, and R is hydrogen atom, acyl group, or a monovalent
  aromatic group having not more than 10 carbon atoms,
  which is bonded to a nitrogen atom by a carbon atom of the
  aromatic ring, and a salt thereof, for the production of a
  TNF-α production inhibitory agent,
(27) use of a 1,3-thiazole compound substituted at the
  5-position by a pyridyl group optionally having
  substituent(s), a salt thereof or a prodrug thereof for the
  production of an agent for the prophylaxis or treatment of
  asthma, chronic obstructive pulmonary disease (COPD),
  allergic disease (e.g., allergic dermatitis, allergic rhinitis),
  inflammation, Addison's disease, autoimmune hemolytic
  anemia, systemic lupus erythematosus, Crohn's disease,
  psoriasis, rheumatism, cerebral hemorrhage, cerebral
  infarction, head trauma, spinal cord injury, brain edema,
  multiple sclerosis, Alzheimer's disease, Parkinson's
  disease, amyotrophic lateral sclerosis, diabetes, arthritis
  (e.g., chronic rheumatoid arthritis, osteoarthritis),
  osteoporosis, toxemia (e.g., sepsis), Crohn's disease,
  ulcerative colitis, chronic pneumonia, pulmonary
  silicosis, pulmonary sarcoidosis, pulmonary tuberculosis,
  cachexia, arteriosclerosis, Creutzfeldt-Jakob disease,
  virus infection, atopic dermatitis, AIDS encephalopathy,
  meningitis, angina pectoris, cardiac infarction, congestive heart failure, hepatitis, kidney failure, nephritis, malignant tumor, transplantation, dialysis hypotension or disseminated intravascular coagulation, and

(28) use of a 1,3-thiazole compound substituted at the 5-position by a pyridyl group optionally having substituent(s), a salt thereof or a prodrug thereof for the production of an agent for the prophylaxis or treatment of chronic rheumatoid arthritis or osteoarthritis.

BEST MODE TO PRACTICE THE INVENTION

In the present specification, as "acyl group", for example, there are an acyl group represented by the formula:

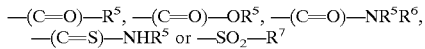
—(C=S)—NHR$^5$ or —SO$_2$—R$^7$ (wherein R$^5$ represents a hydrogen atom, a hydrocarbon group optionally having substituent(s) or a heterocyclic group optionally having substituent(s), R$^6$ represents a hydrogen atom or a C$_{1-6}$ alkyl, R$^7$ represents a hydrocarbon group optionally having substituent(s) or a heterocyclic group optionally having substituent(s)) and the like.

In the aforementioned formula, as "hydrocarbon group" of "hydrocarbon group optionally having substituent(s)" represented by R$^5$, for example, there are an acyclic or cyclic hydrocarbon group (for example, alkyl, alkenyl, alkynyl, cycloalkyl, aryl, aralkyl and the like) and the like. Among them, acyclic or cyclic hydrocarbon groups having 1 to 16 carbon atom(s) are preferable.

As "alkyl", for example, C$_{1-6}$ alkyl (for example, methyl, ethyl, propyl, isopropyl, butyl, isobutyl, sec-butyl, tert-butyl, pentyl, hexyl and the like) and the like are preferable.

As "alkenyl", for example, C$_{2-6}$ alkenyl (for example, vinyl, allyl, isopropenyl, 1-butenyl, 2-butenyl, 3-butenyl, 2-methyl-2-propenyl, 1-methyl-2-propenyl, 2-methyl-1-propenyl and the like) and the like are preferable.

As "alkynyl", for example, C$_{2-6}$ alkynyl (for example, ethynyl, propargyl, 1-butynyl, 2-butynyl, 3-butynyl, 1-hexynyl and the like) and the like are preferable.

As "cycloalkyl", for example, C$_{3-6}$ cycloalkyl (for example, cyclopropyl, cyclobutyl, cyclopentyl, cyclohexyl and the like) and the like are preferable.

As "aryl", for example, C$_{6-14}$ aryl (for example, phenyl, 1-naphthyl, 2-naphthyl, 2-biphenylyl, 3-biphenylyl, 4-biphenylyl, 2-anthryl and the like) and the like are preferable.

As "aralkyl", for example, C$_{7-16}$ aralkyl (for example, benzyl, phenethyl, diphenylmethyl, 1-naphthylmethyl, 2-naphthylmethyl, 2,2-diphenylethyl, 3-phenylpropyl, 4-phenylbutyl, 5-phenylpentyl and the like) and the like are preferable.

As "substituent(s)" of "hydrocarbon group optionally having substituent(s)" represented by R$^5$, for example, there are oxo, halogen atom (for example, fluorine, chlorine, bromine, iodine and the like), C$_{1-3}$ alkylenedioxy (for example, methylenedioxy, ethylenedioxy and the like), nitro, cyano, optionally halogenated C$_{1-6}$ alkyl, optionally halogenated C$_{2-6}$ alkenyl, carboxy C$_{2-6}$ alkenyl (for example, 2-carboxyethenyl, 2-carboxy-2-methylethenyl and the like), optionally halogenated C$_{2-6}$ alkynyl, optionally halogenated C$_{3-6}$ alkcycloalkyl, C$_{6-14}$ aryl (for example, phenyl, 1-naphthyl, 2-naphthyl, 2-biphenylyl, 3-biphenylyl, 4-biphenylyl, 2-anthryl and the like), optionally halogenated C$_{1-8}$ alkoxy, C$_{1-6}$ alkoxy-carbonyl-C$_{1-6}$ alkoxy (for example, ethoxycarbonylmethyloxy and the like), hydroxy, C$_{6-14}$ aryloxy (for example, phenyloxy, 1-naphthyloxy, 2-naphthyloxy and the like), C$_{7-16}$ aralkyloxy (for example, benzyloxy, phenethyloxy and the like), mercapto, optionally halogenated C$_{1-6}$ alkylthio, C$_{6-14}$ arylthio (for example, phenylthio, 1-naphthylthio, 2-naphthylthio and the like), C$_{7-16}$ aralkylthio (for example, benzylthio, phenethylthio and the like), amino, mono-C$_{1-6}$ alkylamino (for example, methylamino, ethylamino and the like), mono-C$_{6-14}$ arylamino (for example, phenylamino, 1-naphthylamino, 2-naphthylamino and the like), di-C$_{1-6}$ alkylamino (for example, dimethylamino, diethylamino, ethylmethylamino and the like), di-C$_{6-14}$ arylamino (for example, diphenylamino and the like), formyl, carboxy, carboxy-C$_{2-6}$ alkenyl, carboxy-C$_{1-6}$ alkyl, C$_{1-6}$ alkyl-carbonyl (for example, acetyl, propionyl and the like), C$_{3-6}$ cycloalkyl-carbonyl (for example, cyclopropylcarbonyl, cyclopentylcarbonyl, cyclohexylcarbonyl and the like), C$_{1-6}$ alkoxy-carbonyl (for example, methoxycarbonyl, ethoxycarbonyl, propoxycarbonyl, tert-butoxycarbonyl and the like), C$_{6-14}$ aryl-carbonyl (for example, benzoyl, 1-naphthoyl, 2-naphthoyl and the like), C$_{7-16}$ aralkyl-carbonyl (for example, phenylacetyl, 3-phenylpropionyl and the like), C$_{6-14}$ aryloxy-carbonyl (for example, phenoxycarbonyl and the like), C$_{7-16}$ aralkyloxy-carbonyl (for example, benzyloxycarbonyl, phenethyloxycarbonyl and the like), 5 or 6 membered heterocyclic carbonyl (for example, nicotinoyl, isonicotinoyl, thenoyl, furoyl, morpholinocarbonyl, thiomorpholinocarbonyl, piperazin-1-ylcarbonyl, pyrrolidin-1-ylcarbonyl and the like), carbamoyl, thiocarbamoyl, mono-C$_{1-6}$ alkyl-carbamoyl (for example, methylcarbamoyl, ethylcarbamoyl and the like), di-C$_{1-6}$ alkyl-carbamoyl (for example, dimethylcarbamoyl, diethylcarbamoyl, ethylmethylcarbamoyl and the like), mono- or di-C$_{6-14}$ aryl-carbamoyl (for example, phenylcarbamoyl, 1-naphthylcarbamoyl, 2-naphthylcarbamoyl and the like), mono- or di-5 or 6 membered heterocyclic carbamoyl (for example, 2-pyridylcarbamoyl, 3-pyridylcarbamoyl, 4-pyridylcarbamoyl, 2-thienylcarbamoyl, 3-thienylcarbamoyl and the like), C$_{1-6}$ alkylsulfonyl (for example, methylsulfonyl, ethylsulfonyl and the like), C$_{1-6}$ alkylsulfinyl (for example, methylsulfinyl, ethylsulfinyl and the like), C$_{6-14}$ arylsulfonyl (for example, phenylsulfonyl, 1-naphthylsulfonyl, 2-naphthylsolfonyl and the like), C$_{6-14}$ arylsulfinyl (for example, phenylsulfinyl, 1-naphthylsulfinyl, 2-naphthylsulfinyl and the like), formylamino, C$_{1-6}$ alkyl-carbonylamino (for example, acetylamino and the like), C$_{6-14}$ aryl-carbonylamino (for example, benzoylamino, naphthoylamino and the like), C$_{1-6}$ alkoxy-carbonylamino (for example, methoxycarbonylamino, ethoxycarbonylamino, propoxycarbonylamino, butoxycarbonylamino and the like), C$_{1-6}$ alkylsulfonylamino (for example, methylsulfonylamino, ethylsulfonylamino and the like), C$_{6-14}$ arylsulfonylamino (for example, phenylsulfonylamino, 2-naphthylsulfonylamino, 1-naphthylsulfonylamino and the like), C$_{1-6}$ alkyl-carbonyloxy (for example, acetoxy, propionyloxy and the like), C$_{6-14}$ aryl-carbonyloxy (for example, benzoyloxy, naphthylcarbonyloxy and the like), C$_{1-6}$ alkoxy-carbonyloxy (for example, methoxycarbonyloxy, ethoxycarbonyloxy, propoxycarbonyloxy, butoxycarbonyloxy and the like), mono-C$_{1-6}$ alkyl-carbamoyloxy (for example, methylcarbamoyloxy, ethylcarbamoyloxy and the like), di-C$_{1-6}$ alkyl-carbamoyloxy (for example, dimethylcarbamoyloxy, diethylcarbamoyloxy and the like), C$_{6-14}$ aryl-carbamoyloxy (for example, phenylcarbamoyloxy, naphthylcarbamoyloxy and the like), nicotinoyloxy, 5 to 7 membered saturated cyclic amino optionally having substituent(s), 5 to 10 membered aromatic heterocyclic group (for example, 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like), sulfo and the like.

The "hydrocarbon group" may have 1 to 5, preferably 1 to 3 aforementioned substituent(s) at a substitutable position and, when the number of substituents is 2 or more, respective substituents may be the same or different.

As aforementioned "optionally halogenated $C_{1-6}$ alkyl", for example, there are $C_{1-6}$ alkyl (for example, methyl, ethyl, propyl, isopropyl, butyl, isobutyl, sec-butyl, tert-butyl, pentyl, hexyl and the like) and the like optionally having 1 to 5, preferably 1 to 3 halogen atom(s) (for example, fluorine, chlorine, bromine, iodine and the like). Examples thereof are methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl and the like.

As the aforementioned "optionally halogenated $C_{2-6}$ alkenyl", for example, there are $C_{2-6}$ alkenyl (for example, vinyl, propenyl, isopropenyl, 2-buten-1-yl, 4-penten-1-yl, 5-hexen-1-yl) and the like optionally having 1 to 5, preferably 1 to 3 halogen atom(s) (for example, fluorine, chlorine, bromine, iodine and the like).

As the aforementioned "optionally halogenated $C_{2-6}$ alkynyl", there are $C_{2-6}$ alkynyl (for example, 2-butyn-1-yl, 4-pentyn-1-yl, 5-hexyn-1-yl and the like) and the like optionally having 1 to 5, preferably 1 to 3 halogen atom(s) (for example, fluorine, chlorine, bromine, iodine and the like).

As the aforementioned "optionally halogenated $C_{3-6}$ cycloalkyl", for example, there are $C_{3-6}$ cycloalkyl (for example, cyclopropyl, cyclobutyl, cyclopentyl, cyclohexyl and the like) and the like optionally having 1 to 5, preferably 1 to 3 halogen atom(s) (for example, fluorine, chlorine, bromine, iodine and the like). Examples thereof are cyclopropyl, cyclobutyl, cyclopentyl, cyclohexyl, 4,4-dichlorocyclohexyl, 2,2,3,3-tetrafluorocyclopentyl, 4-chlorocyclohexyl and the like.

As the aforementioned "optionally halogenated $C_{1-8}$ alkoxy", for example, there are $C_{1-8}$ alkoxy (for example, methoxy, ethoxy, propoxy, isopropoxy, butoxy, isobutoxy, sec-butoxy, pentyloxy, hexyloxy and the like) and the like optionally having 1 to 5, preferably 1 to 3 halogen atom(s) (for example, fluorine, chlorine, bromine, iodine and the like). Examples thereof are methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy and the like.

As the aforementioned "optionally halogenated $C_{1-6}$ alkylthio", for example, there are $C_{1-6}$ alkylthio (for example, methylthio, ethylthio, propylthio, isopropylthio, butylthio, sec-butylthio, tert-butylthio and the like) and the like optionally having 1 to 5, preferably 1 to 3 halogen atom(s) (for example, fluorine, chlorine, bromine, iodine and the like). Examples thereof are methylthio, difluoromethylthio, trifluoromethylthio, ethylthio, propylthio, isopropylthio, butylthio, 4,4,4-trifluorobutylthio, pentylthio, hexylthio and the like.

As "5 to 7 membered saturated cyclic amino" of the aforementioned "5 to 7 membered saturated cyclic amino optionally having substituent(s)", there are 5 to 7 membered saturated cyclic amino optionally containing 1 to 4 of one or two kinds of heteroatom(s)selected from a nitrogen atom, a sulfur atom and an oxygen atom in addition to one nitrogen atom and carbon atoms and examples thereof are pyrolidin-1-yl, piperidino, piperazin-1-yl, morpholino, thiomorpholino, hexahydroazepin-1-yl and the like.

As "substituents" of the "5 to 7 membered saturated cyclic amino optionally having substituent(s)", for example, there are 1 to 3 $C_{1-6}$ alkyl (for example, methyl, ethyl, propyl, isopropyl, butyl, isobutyl, sec-butyl, tert-butyl pentyl, hexyl and the like), $C_{6-14}$ aryl (for example, phenyl, 1-naphthyl, 2-naphthyl, 2-biphenylyl, 3-biphenylyl, 4-biphenylyl, 2-anthryl and the like), $C_{1-6}$ alkyl-carbonyl (for example, acetyl, propionyl and the like), 5 to 10 membered aromatic heterocyclic group (for example, 2-thienyl, 3-thienyl, 2-pyridyl, 3-pyridyl, 4-pyridyl, 2-quinolyl, 3-quinolyl, 4-quinolyl, 5-guinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like), oxo and the like.

As "heterocyclic group" of "heterocyclic group optionally having substituent(s)" represented by $R^5$, for example, there is a monovalent group obtained by removing one arbitrary hydrogen atom from a 5 to 14 membered (monocyclic, bicyclic or tricyclic) heterocycle containing 1 to 4 of one or two kinds of heteroatom(s) selected from a nitrogen atom, a sulfur atom and an oxygen atom in addition to carbon atoms, preferably (i) a 5 to 14 membered (preferably 5 to 10 membered) aromatic heterocycle, (ii) a 5 to 10 membered non-aromatic heterocycle or (iii) a 7 to 10 membered bridged heterocycle.

As the aforementioned "5 to 14 membered (preferably 5 to 10 membered) aromatic heterocycle", there are an aromatic heterocycle such as thiophene, benzo[b]thiophene, enzo[b]furan, benzimidazole, benzoxazole, benzothiazole, enzisothiazole, naphtho[2,3-b]thiophene, furan, pyrrole, midazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine and the like, and a ring formed by fusing these rings (preferably monocyclic) with one or more (preferably 1 to 2) aromatic ring(s) (for example, benzene ring and the like).

As the aforementioned "5 to 10 membered non-aromatic heterocycle", for example, there are pyrrolidine, imidazoline, pyrazolidine, pyrazoline, piperidine, piperazine, morpholine, thiomorpholine, dioxazole, oxadiazoline, thiadiazoline, triazoline, thiadiazole, dithiazole and the like.

As the aforementioned "7 to 10 membered bridged heterocycle", for example, there are quinuclidine, 7-azabicyclo[2,2,1]heptane and the like.

The "heterocyclic group" is preferably a 5 to 14 membered (preferably 5 to 10 membered) (monocyclic or bicyclic) heterocyclic group containing preferably 1 to 4 of one or two kinds of heteroatom(s) selected from a nitrogen atom, a sulfur atom and an oxygen atom in addition to carbon atoms. More particularly, examples thereof are an aromatic heterocyclic group such as 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 3-pyrrolyl, 2-imidazolyl, 3-pyridazinyl, 3-isothiazolyl, 3-isoxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like, and a non-aromatic heterocyclic group such as 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino and the like.

Among them, for example, a 5 or 6 membered heterocyclic group containing 1 to 3 heteroatom(s) selected from a nitrogen atom, a sulfur atom and an oxygen atom in addition to carbon s atoms is further preferable. More particularly, examples thereof are 2-thienyl, 3-thienyl, 2-pyridyl, 3-pyridyl, 4-pyridyl, 2-furyl, 3-furyl, pyrazinyl, 2-pyrimidinyl, 3-pyrrolyl, 3-pyridazinyl, 3-isothiazolyl, 3-isoxazolyl, 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino and the like.

As "substituent(s)" of "heterocyclic group optionally having substituent(s)", for example, there are the same "substituent(s)" as substituent(s) of "hydrocarbon group optionally having substituent(s)" represented by $R^5$.

The "heterocyclic group" may have 1 to 5, preferably 1 to 3 aforementioned substituent(s) at a substitutable position and, when the number of substituents is 2 or more, respective substituents may be the same or different.

As "$C_{1-6}$ alkyl" represented by $R^6$, for example, there are methyl, ethyl, propyl, isopropyl, butyl, isobutyl, sec-butyl, tert-butyl, pentyl, hexyl and the like.

As "hydrocarbon group optionally having substituent(s)" and "heterocyclic group optionally having substituent(s)" represented by $R^7$, for example, there are the aforementioned "hydrocarbon group optionally having substituent(s)" and "heterocyclic group optionally having substituent(s)" represented by $R^5$, respectively.

As "hydrocarbon group optionally having substituent(s)" represented by $R^1$, for example, there are "hydrocarbon group optionally having substituent(s)" represented by $R^5$.

As "heterocyclic group optionally having substituent(s)" represented by $R^1$, for example, there are "hydrocarbon group optionally having substituent(s)" represented by $R^5$.

As "amino group optionally having substituent(s)" represented by $R^1$, for example, there are (1) an amino group optionally having 1 or 2 substituent(s) and (2) a cyclic amino group optionally having substituent(s), and the like.

As "substituent(s)" of "amino group optionally having 1 or 2 substituent(s)" of the aforementioned (1), for example, there are a hydrocarbon group optionally having substituent(s), a heterocyclic group optionally having substituent(s), an acyl group, an alkylidene group optionally having substituent(s), and the like. As these "hydrocarbon group optionally having substituent(s)" and "heterocyclic group optionally having substituent(s)", there are the same "hydrocarbon group optionally having substituent(s)" and "heterocyclic group optionally having substituent(s)" as those represented by $R^5$ described above, respectively.

As "alkylidene group" of "alkylidene group optionally having substituent(s)", for example, there are a $C_{1-6}$ alkylidene group (for example, methylidene, ethylidene, propylidene and the like) and the like. As "substituent(s)" of "alkylidene group optionally having substituent(s)", there are 1 to 5, preferably 1 to 3 same substituent(s) as "substituent(s)" of "hydrocarbon group optionally having substituent(s)" represented by $R^5$.

When the number of the aforementioned "substituent(s)" of "amino group optionally having 1 or 2 substituent(s)" is 2, respective substituent(s) may be the same or different.

As "cyclic amino group" of "cyclic amino group optionally having substituent(s)" of the aforementioned (2), there are a 5 to 7 membered non-aromatic cyclic amino group optionally containing 1 to 4 of one or two kinds of heteroatom(s) selected from a nitrogen atom, a sulfur atom and an oxygen atom in addition to one nitrogen atom and carbon atoms. More particularly, examples thereof are pyrrolidin-1-yl, piperidino, piperazin-1-yl, morpholino, thiomorpholino, hexahydroazepin-1-yl, imidazolidin-1-yl, 2,3-dihydro-1-H-imidazol-1-yl, tetrahydro-1(2H)-pyrimidinyl, 3,6-dihydro-1(2H)-pyrlmidinyl, 3,4-dihydro-1(2H)-pyrimidinyl and the like. As "substituent(s)" of "cyclic amino optionally having substituent(s)", there are 1 to 3 same ones as "substituent(s)" of "5 to 7 membered saturated cyclic amino group optionally having substituent(s)" which were described in detail as "substituent(s)" of "hydrocarbon group optionally having substituent(s)" represented by $R^5$.

Examples of the 5 to 7 membered non-aromatic cyclic amino group having one oxo, there are 2-oxoimidazolidin-1-yl, 2-oxo-2,3-dihydro-1-H-imidazol-1-yl, 2-oxotetrahydro-1(2H)-pyrimidinyl, 2-oxo-3,6-dihydro-1(2H)-pyrimidinyl, 2-oxo-3,4-dihydro-1(2H)-pyrimidinyl, 2-oxopyrrolidin-1-yl, 2-oxopiperidino, 2-oxopiperazin-1-yl, 3-oxopiperazin-1-yl, 2-oxo-2,3,4,5,6,7-hexahydroazepin-1-yl and the like.

As $R^1$, an amino group optionally having substituent(s) and an aryl group optionally having substituent(s) are preferable. As further preferable example of the "amino group optionally having substituent(s)" is an amino group optionally having 1 or 2 acyl represented by the formula: —(C=O)—$R^5$, —(C=O)—$OR^5$, —(C=O)—$NR^5R^6$, —(C=S)—$NHR^5$ or —$SO_2R^7$ [wherein respective symbols represent the same meanings as described above].

More preferable example is an amino group optionally having 1 or 2 acyl represented by the formula: —C(C=O)—$R^5$ or —(C=O)—$NR^5R^6$ [wherein respective symbols represent the same meanings as described above].

As the "aryl group optionally having substituent(s)", for example, there is preferably a $C_{6-14}$ aryl group (preferably a phenyl group and the like) optionally having 1 to 5 substituent(s) selected from $C_{1-6}$ alkylthio, $C_{6-14}$ arylthio, $C_{1-6}$ alkylsulfinyl, $C_{6-14}$ arylsulfinyl, $C_{1-6}$ alkylsulfonyl, $C_{6-14}$ arylsulfonyl and carboxy.

Particularly, as $R^1$, there are mentioned
(a) $C_{6-14}$ aryl group (preferably $C_{6-10}$ aryl) optionally having 1 to 5 substituent(s) selected from halogen atom, optionally halogenated $C_{1-6}$ alkyl, carboxy $C_{2-6}$ alkenyl, optionally halogenated $C_{1-6}$ alkoxy, $C_{1-6}$ alkoxy-carbonyl-$C_{1-6}$ alkoxy, hydroxy, amino, mono- or di-$C_{1-6}$ alkylamino, carboxy, $C_{1-6}$ alkoxy-carbonyl, mono- or di-$C_{1-6}$ alkyl-carbamoyl, $C_{6-14}$ aryl-carbonylamino, $C_{1-3}$ alkylenedioxy, $C_{1-6}$ alkylthio, $C_{6-14}$ arylthio, $C_{1-6}$ alkylsulfinyl, $C_{6-14}$ arylsulfinyl, $C_{1-6}$ alkylsulfonyl, $C_{6-14}$ arylsulfonyl, nitro and the like,
(b) $C_{1-8}$ alkyl group optionally having 1 to 5 substituent(s) selected from halogen atom, optionally halogenated $C_{1-6}$ alkyl, carboxy $C_{2-6}$ alkenyl, optionally halogenated $C_{1-6}$ alkoxy, $C_{1-6}$ alkoxy-carbonyl-$C_{1-6}$ alkoxy, hydroxy, amino, mono- or di-$C_{1-6}$ alkylamino, carboxy, $C_{1-6}$ alkoxy-carbonyl, mono- or di-$C_{1-6}$ alkyl-carbamoyl and $C_{6-14}$ aryl-carbonylamino,
(c) $C_{3-6}$ alkcycloalkyl group (e.g., cyclohexyl) optionally having 1 to 5 substituent(s) selected from halogen atom, optionally halogenated $C_{1-6}$ alkyl, carboxy $C_{2-6}$ alkenyl, optionally halogenated $C_{1-6}$ alkoxy, $C_{1-6}$ alkoxycarbonyl-$C_{1-6}$ alkoxy, hydroxy, amino, mono- or di-$C_{1-6}$ alkylamino, carboxy, $C_{1-6}$ alkoxy-carbonyl, mono- or di-$C_{1-6}$ alkyl-carbamoyl and $C_{6-14}$ aryl-carbonylamino, (d) $C_{7-16}$ aralkyl group (e.g., phenyl-$C_{1-6}$ alkyl group), (e) 5 to 10 membered aromatic heterocyclic group containing 1 to 4 of one or two kinds of heteroatom(s) selected from a nitrogen atom, a sulfur atom and an oxygen atom in addition to carbon atoms (e.g., 5 or 6 membered aromatic heterocyclic group such as pyridyl, thienyl and the like), (f) 5 to 10 membered non-aromatic heterocyclic group containing 1 or 2 of one or two kinds of heteroatom(s) selected from a nitrogen atom, a sulfur atom and an oxygen atom in addition to carbon atoms, which may have $C_{6-14}$ aryl (e.g., phenyl), $C_{1-6}$ alkyl-carbonyl or oxo, such as 5 or 6 membered non-aromatic cyclic amino group (e.g., piperidino, piperazino and the like), (g) amino group optionally having 1 or 2 substituent(s) selected from the group consisting of the following (1) to (7) [(1) $C_{1-6}$ alkyl, (2) $C_{6-14}$ aryl, (3) $C_{7-16}$ aralkyl, (4) a 5 or 6 membered heterocyclic group (e.g., pyridyl) containing 1 or 2 heteroatom(s) selected from a nitrogen atom, a sulfur atom and an oxygen atom in addition to carbon atoms, (5) $C_{1-6}$ alkyl-carbonyl, $C_{3-6}$ cycloalkyl-carbonyl, $C_{6-14}$ aryl-carbonyl, $C_{7-16}$ aralkyl-carbonyl, $C_{1-6}$ alkyl-carbamoyl or 5 or 6 membered heterocyclic carbonyl group optionally having 1 to 3 substituent(s) selected from halogen atom, $C_{1-6}$ alkyl, $C_{1-6}$ alkoxy, carboxy, $C_{1-6}$ alkoxy-carbonyl, cyano, tetrazine and the like, (6) $C_{6-14}$ aryl-carbamoyl group optionally having 1 to 3 substituent(s) selected from halogen atom, $C_{1-6}$ alkyl, $C_{1-6}$ alkoxy, carboxy, $C_{1-6}$ alkoxy-carbonyl, cyano, nitro, mono- or di-$C_{1-6}$ alkylamino and the like, (7) di-$C_{1-6}$ alkylamino-$C_{1-6}$ alkylidene], or (h) carboxy group and the like are preferable.

As the "pyridyl group" of the "pyridyl group optionally having substituent(s)" represented by $R^2$, 1-, 2-, 3- or 4-pyridyl group and the like are used.

As the "substituent(s)" of the "pyridyl group optionally having substituent(s)" represented by $R^2$, for example, those similar to the "substituent(s)" of the "hydrocarbon group optionally having substituent(s)" represented by the aforementioned $R^5$ are used.

The "pyridyl group" may have 1 to 5, preferably 1 to 3, substituent(s) such as those mentioned above at substitutable position(s). When the number of substituent is 2 or more, the respective substituent(s) may be the same or different. In addition, the nitrogen atom in the ring of the "pyridyl group" may be N-oxidized.

$R^2$ is preferably a pyridyl group optionally having substituent(s) (e.g., 3-pyridyl group, 4-pyridyl group and the like, preferably 4-pyridyl group).

As $R^2$, pyridyl group optionally having 1 or 2 substituent(s) selected from the group consisting of $C_{1-6}$ alkyl (e.g., methyl), hydroxy and $C_{1-6}$ alkyl-carbonyloxy (e.g., acetyloxy) and the like are preferable.

As the "aromatic group" of "aromatic group optionally having substituent(s)" represented by $R^3$, for example, there are an aromatic hydrocarbon group, an aromatic heterocyclic group and the like.

As the "aromatic hydrocarbon group", examples thereof include a $C_{6-14}$ monocyclic or fused polycyclic (bicyclic or tricyclic) aromatic hydrocarbon group. As examples, there are a $C_{6-14}$ aryl group and the like such as phenyl, 1-naphthyl, 2-naphthyl, 2-biphenylyl, 3-biphenylyl, 4-biphenylyl, 2-anthryl and the like.

As the "aromatic heterocyclic group", there are a 5 to 14 membered (preferably 5 to 10 membered)(monocyclic or bicyclic) aromatic heterocyclic group containing preferably 1 to 4 of one or two kinds of heteroatom(s) selected from a nitrogen atom, a sulfur atom and an oxygen atom in addition to carbon atoms and the like and, more particularly, there are an aromatic heterocyclic group such as 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 3-pyrrolyl, 2-imidazolyl, 3-pyridazinyl, 3-isothiazolyl, 3-isoxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like.

As the "substituent(s)" of the "aromatic group optionally having substituent(s)", there are 1 to 5, preferably 1 to 3 same substituent(s) as "substituent(s)" of "hydrocarbon group optionally having substituent(s)" represented by the aforementioned $R^5$. When the number of substituents is 2 or more, respective substituents may be the same or different. The adjacent two substituents may form a 4 to 7 membered non-aromatic carbon ring. Preferably, it is a 5 membered non-aromatic carbon ring.

$R^3$ is preferably a $C_{6-10}$ aryl group optionally having substituent(s). More preferably, it is-a phenyl group optionally having substituent(s). The substituent of these $C_{6-10}$ aryl group and phenyl group is preferably 1 to 3 substituent(s) selected from halogen atom, $C_{1-3}$ alkylenedioxy, optionally halogenated $C_{1-6}$ alkyl, carboxy $C_{2-6}$ alkenyl, $C_{3-6}$ cycloalkyl, optionally halogenated $C_{1-6}$ alkoxy, hydroxy, $C_{7-16}$ aralkyloxy, $C_{1-6}$ alkyl-carbonyloxy and carboxy. Particularly preferably, it is optionally halogenated $C_{1-6}$ alkyl (e.g., $C_{1-3}$ alkyl such as methyl, ethyl and the like), optionally halogenated $C_{1-8}$ alkoxy (e.g., $C_{1-3}$ alkoxy such as methoxy, ethoxy and the like). The two adjacent alkyl groups as substituents may be bonded to form a 5 membered non-aromatic carbon ring.

When compound (I) or compound (Ia) is used as a TNF-α production inhibitor, the compound (I) or compound (Ia) does not include a compound of the formula

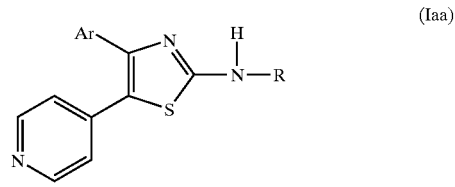

(Iaa)

wherein Ar is an unsubstituted or substituted aryl group bonded to a thiazole ring by a carbon atom of the aromatic ring, and R is a hydrogen atom, acyl group, or a monovalent aromatic group having not more than 10 carbon atoms, which is bonded to a nitrogen atom by a carbon atom of the aromatic ring.

As the compound (I), for example, compound (Ia) is preferable.

As compound (Ia), the following compounds of (A)–(B) and the like are preferable.

(A) A compound (Ia) wherein $R^1$ is (a) an amino group which may have 1 or 2 acyl of the formula: —(C=O)—$R^5$ or —(C=O)—$NR^5R^6$ wherein each symbol is as defined above or (b) a $C_{6-14}$ aryl group optionally having 1 to 5 substituent(s) selected from $C_{1-6}$ alkylthio, $C_{6-14}$ arylthio, $C_{1-6}$ alkylsulfinyl, $C_{6-14}$ arylsulfinyl, $C_{1-6}$ alkylsulfonyl, $C_{6-14}$ arylsulfonyl and carboxy and the like; $R^2$ is pyridyl group optionally having 1 to 5 substituent(s) selected from $C_{1-6}$ alkyl, hydroxy and $C_{1-6}$ alkyl-carbonyloxy; and $R^3$ is a $C_{6-14}$ aryl group optionally having 1 to 5 substituent(s) selected from halogen atom, optionally halogenated $C_{1-6}$ alkyl, optionally halogenated $C_{1-6}$ alkoxy and carboxy.

(B) A compound (Ia) wherein $R^1$ is (i) $C_{1-8}$alkyl, $C_{3-6}$ cycloalkyl or $C_{6-14}$ aryl (preferably $C_{6-10}$ aryl) optionally having 1 to 5 substituent(s) selected from halogen atom, optionally halogenated $C_{1-6}$ alkyl, carboxy $C_{2-6}$ alkenyl, optionally halogenated $C_{1-6}$ alkoxy, $C_{1-6}$ alkoxy-carbonyl-$C_{1-6}$ alkoxy, hydroxy, amino, mono- or di-$C_{1-6}$ alkylamino, carboxy, $C_{1-6}$ alkoxy-carbonyl, mono- or di-$C_{1-6}$ alkyl-carbamoyl and $C_{6-14}$ aryl-carbonylamino, (ii) a 5 membered heterocyclic group, (iii) an amino group optionally having 1 or 2 substituent(s) selected from (1) $C_{1-6}$ alkyl, (2) $C_{6-14}$ aryl, (3) $C_{7-16}$ aralkyl, (4) 6 membered heterocyclic group and (5) $C_{1-6}$ alkyl-carbonyl, $C_{3-6}$ alkcycloalkyl-carbonyl, $C_{6-14}$ aryl-carbonyl, $C_{7-16}$ aralkyl-carbonyl, $C_{1-6}$ alkyl-carbamoyl or 5 or 6 membered heterocyclic carbonyl, each optionally having 1 to 3 substituent(s) selected from halogen atom, $C_{1-6}$ alkyl, $C_{1-6}$ alkoxy, carboxy and $C_{1-6}$ alkoxy-carbonyl, or an amino group optionally having di-$C_{1-6}$ alkylamino-$C_{1-6}$ alkylidene, (iv) a 5 or 6 membered non-aromatic cyclic amino group optionally substituted by $C_{1-6}$ alkyl-carbonyl or oxo, or (v) a carboxy group;

$R^2$ is a pyridyl group optionally having 1 to 3 substituent(s) selected from $C_{1-6}$ alkyl, hydroxy and $C_{1-6}$ alkyl-carbonyloxy;

$R^3$ is a $C_{6-10}$ aryl group optionally having 1 to 3 substituent(s) selected from halogen atom, $C_{1-3}$ alkylenedioxy, optionally halogenated $C_{1-6}$ alkyl, carboxy $C_{2-6}$ alkenyl, optionally halogenated $C_{1-8}$ alkoxy, hydroxy, $C_{7-16}$ aralkyloxy and $C_{1-6}$ alkyl-carbonyloxy (two adjacent alkyl groups as substituents may be bonded to form a 5 membered non-aromatic carbon ring).

Moreover, preferable examples of compound (I) and compound (Ia) include:

[4-(4-methoxyphenyl)-5-(4-pyridyl)-1,3-thiazol-2-yl]amine (Reference Example 13-14),

[4-phenyl-5-(4-pyridyl)-1,3-thiazol-2-yl]amine (Reference Example 13-15),

N-methyl [4-(4-methoxyphenyl)-5-(4-pyridyl)-1,3-thiazol-2-yl]amine (Reference Example 13-16), N-methyl [4-phenyl-5-(4-pyridyl)-1,3-thiazol-2-yl]amine (Reference Example 13-47), N-methyl [4-(4-fluorophenyl)-5-(4-pyridyl)-1,3-thiazol-2-yl]amine (Reference Example 13-69), N-methyl [4-(4-chlorophenyl)-5-(4-pyridyl)-1,3-thiazol-2-yl]amine (Reference Example 13-70), N-methyl [4-(4-bromophenyl)-5-(4-pyridyl)-1,3-thiazol-2-yl]amine (Reference Example 13-71), 2-phenyl-N-[4-phenyl-5-(4-pyridyl)-1,3-thiazol-2-yl]acetamide (Reference Example 23-29), 3-phenyl-N-[4-phenyl-5-(4-pyridyl)-1,3-thiazol-2-yl]propionamide (Reference Example 23-30), N-[4-(3-chlorophenyl)-5-(4-pyridyl)-1,3-thiazol-2-yl]acetamide (Reference Example 23-49), N-[4-(3-chlorophenyl)-5-(4-pyridyl)-1,3-thiazol-2-yl]propionamide (Reference Example 23-50), N-[4-(3-methylphenyl)-5-(4-pyridyl)-1,3-thiazol-2-yl]acetamide (Reference Example 23-51), N-[4-(3-methylphenyl)-5-(4-pyridyl)-1,3-thiazol-2-yl]propionamide (Reference Example 23-52),

[4-(3-chlorophenyl)-5-(4-pyridyl)-1,3-thiazol-2-yl]amine (Reference Example 23-59),

[4-(3-methylphenyl)-5-(4-pyridyl)-1,3-thiazol-2-yl]amine (Reference Example 23-60),

[4-(4-chlorophenyl)-5-(4-pyridyl)-1,3-thiazol-2-yl]amine (Reference Example 23-61),

[4-(4-methylphenyl)-5-(4-pyridyl)-1,3-thiazol-2-yl]amine (Reference Example 23-62), N-[4-phenyl-5-(4-pyridyl)-1,3-thiazol-2-yl]acetamide (Reference Example 23-71), N-phenyl-[4-(4-methoxyphenyl)-5-(4-pyridyl)-1,3-thiazol-2-yl]amine (Reference Example 23-80), N-[4-(4-methoxyphenyl)-5-(4-pyridyl)-1,3-thiazol-2-yl] nicotinamide (Reference Example 23-101), N-[4-(4-methoxyphenyl)-5-(4-pyridyl)-1,3-thiazol-2-yl] isonicotinamide (Reference Example 23-102),

[4-(3,4-dimethylphenyl)-5-(4-pyridyl)-1,3-thiazol-2-yl] amine (Reference Example 23-125), N-[4-(3,5-dinethylphenyl)-5-(4-pyridyl)-1,3-thiazol-2-yl] acetamide (Reference Example 23-128),

[4-(2-naphthyl)-5-(4-pyridyl)-1-3-thiazol-2-yl]amine (Reference Example 23-144), N-ethyl-N'-[4-(4-methoxyphenyl)-5-(4-pyridyl)-1,3-thiazol-2-yl]urea (Reference Example 23-156), N-[4-(3,5-dimethylphenyl)-5-(4-pyridyl)-1,3-thiazol-2-yl] isonicotinamide (Reference Example 23-200), N-ethyl-[4-(4-methoxyphenyl)-5-(4-pyridyl)-1,3-thiazol-2-yl]amine (Reference Example 23-269), N-propyl-[4-(3,5-dimethylphenyl)-5-(4-pyridyl)-1,3-thiazol-2-yl]amine (Reference Example 23-276), N-butyl-[4-(3,5-dimethylphenyl)-5-(4-pyridyl)-1,3-thiazol-2-yl]amine (Reference Example 23-280), N-benzyl-[4-(3,5-dimethylphenyl)-5-(4-pyridyl)-1,3-thiazol-2-yl]amine (Reference Example 23-281), N-propyl-[4-(4-methoxyphenyl)-5-(4-pyridyl)-1,3-thiazol-2-yl]amine (Reference Example 23-290), N-isopropyl-[4-(4-methoxyphenyl)-5-(4-pyridyl)-1,3-thiazol-2-yl]amine (Reference Example 23-291), N-[4-(4-methoxyphenyl)-5-(4-pyridyl)-1,3-thiazol-2-yl]-N'-phenylurea (Reference Example 23-296), 4-[[[4-(4-methoxyphenyl)-5-(4-pyridyl)-1,3-thiazol-2-yl] amino]carbonyl]benzoic acid (Reference Example 23-299), methyl 4-[2-[4-(methylthio)phenyl]-5-(4-pyridyl)-1,3-thiazol-4-yl]phenyl ether (Reference Example 23-300), 4-[4-(3,5-dimethylphenyl)-5-(4-pyridyl)-1,3-thiazol-2-yl] phenylmethylsulfide (Reference Example 23-302), 4-[4-(4-methoxyphenyl)-5-(4-pyridyl)-1,3-thiazol-2-yl] phenylmethylsulfoxide (Reference Example 23-303), 4-[4-(3,5-dimethylphenyl)-5-(4-pyridyl)-1,3-thiazol-2-yl] phenylmethylsulfoxide (Reference Example 23-305), 4-[4-(4-methoxyphenyl)-5-(4-pyridyl)-1,3-thiazol-2-yl] phenylmethylsulfone (Reference Example 23-306), 4-[4-(3,5-dimethylphenyl)-5-(4-pyridyl)-1,3-thiazol-2-yl] phenylmethylsulfone (Reference Example 23-308), 4-[4-(4-fluorophenyl)-5-(4-pyridyl)-1,3-thiazol-2-yl] phenylmethylsulfide (Reference Example 23-309), 4-[4-(4-chlorophenyl)-5-(4-pyridyl)-1,3-thiazol-2-yl] phenylmethylsulfide (Reference Example 23-310), 4-[4-(4-fluorophenyl)-5-(4-pyridyl)-1,3-thiazol-2-yl] phenylmethylsulfoxide (Reference Example 23-311), 4-[4-(4-chlorophenyl)-5-(4-pyridyl)-1,3-thiazol-2-yl] phenylmethylsulfoxide (Reference Example 23-312), 4-[4-(4-fluorophenyl)-5-(4-pyridyl)-1,3-thiazol-2-yl] phenylmethylsulfone (Reference Example 23-313), 4-[4-(4-chlorophenyl)-5-(4-pyridyl)-1,3-thiazol-2-yl] phenylmethylsulfone (Reference Example 23-314), N-[4-(3,5-dimethylphenyl)-5-(4-pyridyl)-1,3-thiazol-2-yl]-N'-phenylurea (Reference Example 23-315),
2-hydroxy-N-[4-(4-methoxyphenyl)-5-(4-pyridyl)-1,3-thiazol-2-yl]propionamide (Reference Example 23-325),
4-[4-(3,4-dimethylphenyl)-5-(4-pyridyl)-1,3-thiazol-2-yl]phenylmethylsulfide (Reference Example 23-326),
4-[4-(3,4-dimethylphenyl)-5-(4-pyridyl)-1,3-thiazol-2-yl]phenylmethylsulfoxide (Reference Example 23-327),
4-[4-(3,4-dimethylphenyl)-5-(4-pyridyl)-1,3-thiazol-2-yl]phenylmethylsulfone (Reference Example 23-328),
2-hyoxy-N-[4-(4-methoxyphenyl)-5-(4-pyridyl)-1,3-thiazol-2-yl]acetamide (Reference Example 23-329),
4-[[[4-(3,5-dimethylphenyl)-5-(4-pyridyl)-1,3-thiazol-2-yl]amino]carbonyl]benzoic acid (Reference Example 23-337),
3-[[[4-(3,5-dimethylphenyl)-5-(4-pyridyl)-1,3-thiazol-2-yl]amino]carbonyl]benzoic acid (Reference Example 23-342), salts thereof and the like.

Preferable examples of compound (I) and compound (Ia) further include 4-(4-fluorophenyl)-2-phenyl-5-(4-pyridyl)-1,3-thiazole (Reference Example 44-1), methyl 4-[4-(3-methylphenyl)-5-(4-pyridyl)-1,3-thiazol-2-yl]phenylsulfide (Reference Example 44-7), methyl 4-[4-(3-methylphenyl)-5-(4-pyridyl)-1,3-thiazol-2-yl]phenylsulfoxide (Reference Example 44-8), methyl 4-[4-(3-methylphenyl)-5-(4-pyridyl)-1,3-thiazol-2-yl]phenylsulfone (Reference Example 44-26) and the like.

Furthermore, as compound (I) and (Ia),
(S)-N-[4-(3-methylphenyl)-5-[2-(1-phenylethylamino)-4-pyridyl]-1,3-thiazol-2-yl]nicotinamide,
(R)-N-[4-(3-methylphenyl)-5-[2-(1-phenylethylamino)-4-pyridyl]-1,3-thiazol-2-yl]nicotinamide,
(S)-N-[4-(3-methylphenyl)-5-[2-(1-phenylethylamino)-4-pyridyl]-1,3-thiazol-2-yl]-2-methylnicotinamide,
(R)-N-[4-(3-methylphenyl)-5-[2-(1-phenylethylamino)-4-pyridyl]-1,3-thiazol-2-yl]-2-methylnicotinamide,
(S)-N-[4-(3-methylphenyl)-5-[2-(1-phenylethylamino)-4-pyridyl]-1,3-thiazol-2-yl]-2-chloronicotinamide,
(R)-N-[4-(3-methylphenyl)-5-[2-(1-phenylethylamino)-4-pyridyl]-1,3-thiazol-2-yl]-2-chloronicotinamide,
(S)-N-[4-(3-methylphenyl)-5-[2-(1-phenylethylamino)-4-pyridyl]-1,3-thiazol-2-yl]-2-methoxynicotinamide,
(R)-N-[4-(3-methylphenyl)-5-[2-(1-phenylethylamino)-4-pyridyl]-1,3-thiazol-2-yl]-2-methoxynicotinamide,
N-[5-(2-benzylamino-4-pyridyl)-4-(3-methylphenyl)-1,3-thiazol-2-yl]nicotinamide,
N-[5-(2-benzylamino-4-pyridyl)-4-(3-methylphenyl)-1,3-thiazol-2-yl]-2-methoxynicotinamide,
N-[5-(2-benzylamino-4-pyridyl)-4-(3-methylphenyl)-1,3-thiazol-2-yl]-2-chloronicotinamide,
N-[5-(2-benzylamino-4-pyridyl)-4-(3-methylphenyl)-1,3-thiazol-2-yl]-2-methylnicotinamide,
N-[5-(2-benzoylamino-4-pyridyl)-4-(3-methylphenyl)-1,3-thiazol-2-yl]nicotinamide,
N-[5-(2-benzoylamino-4-pyridyl)-4-(3-methylphenyl)-1,3-thiazol-2-yl]-2-methylnicotinamide,
N-[5-(2-benzoylamino-4-pyridyl)-4-(3-methylphenyl)-1,3-thiazol-2-yl]-2-chloronicotinamide,
N-[5-(2-benzoylamino-4-pyridyl)-4-(3-methylphenyl)-1,3-thiazol-2-yl]-2-methoxynicotinamide,
(S)-N-(1-phenylethyl)-4-[2-ethyl-4-(3-methylphenyl)-1,3-thiazol-5-yl]-2-pyridylamine,
(R)-N-(1-phenylethyl)-4-[2-ethyl-4-(3-methylphenyl)-1,3-thiazol-5-yl]-2-pyridylamine,
(S)-N-(1-phenylethyl)-4-[4-(3-methylphenyl)-2-propyl-1,3-thiazol-5-yl]-2-pyridylamine,
(R)-N-(1-phenylethyl)-4-[4-(3-methylphenyl)-2-propy-1,3-thiazol-5-yl]-2-pyridylamine,
(S)-N-(1-phenylethyl)-4-[2-butyl-4-(3-methylphenyl)-1,3-thiazol-5-yl]-2-pyridylamine,
(R)-N-(1-phenylethyl)-4-[2-butyl-4-(3-methylphenyl)-1,3-thiazol-5-yl]-2-pyridylamine,
(S)-N-(1-phenylethyl)-4-[4-(3-methylphenyl)-2-(4-methylthiophenyl)-1,3-thiazol-5-yl]-2-pyridylamine,
(R)-N-(1-phenylethyl)-4-[4-(3-methylphenyl)-2-(4-methylthiophenyl)-1,3-thiazol-5-yl]-2-pyridylamine,
(S)-N-(1-phenylethyl)-4-[4-(3-methylphenyl)-2-(4-methylsulfonylphenyl)-1,3-thiazol-5-yl]-2-pyridylamine,
(R)-N-(1-phenylethyl)-4-[4-(3-methylphenyl)-2-(4-methylsulfonylphenyl)-1,3-thiazol-5-yl]-2-pyridylamine,
(S)-N-(1-phenylethyl)-4-[2-(4-fluorophenyl)-4-(3-methylphenyl)-1,3-thiazol-5-yl]-2-pyridylamine,
(R)-N-(1-phenylethyl)-4-[2-(4-fluorophenyl)-4-(3-methylphenyl)-1,3-thiazol-5-yl]-2-pyridylaminer salts thereof and the like are preferable.

As the salt of Compounds (I) and (Ia), for-example, there are a metal salt, ammonium salt, a salt with an organic base, salt with an inorganic acid, a salt with an organic acid, a salt with basic or acidic amino acid and the like. As a suitable metal salt, there are alkali metal salt such as sodium salt, potassium salt and the like; alkaline earth metal salt such as calcium salt, magnesium salt, barium salt and the like; aluminum salt and the like. As a suitable example of a salt with an organic base, for example, there are salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. As a suitable example of a salt with an inorganic acid, for example, there are salts with hydrochloric acid, hydrobromic acid, nitric acid, sulfuric acid, phosphoric acid and the like. As a suitable example of a salt with an organic acid, for example, there are salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. As a suitable example of a salt with a basic amino acid, for example, there are salts with arginine, lysine, ornithine and the like, As a suitable example of a salt with an acidic amino acid, for example, there are salts with aspartic acid, glutamic acid and the like.

Among them, pharmaceutically acceptable salts are preferable. For example, when a compound has an acidic functional group therein, there are inorganic salts such as alkali metal salt (for example, sodium salt, potassium salt and the like), alkaline earth metal salt (for example, calcium salt, magnesium salt, barium salt and the like), ammonium salts and the like and, when a compound has a basic functional group therein, there are salts with inorganic acids such as hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, p-toluenesulfonic acid and the like.

A process for producing Compound (I) including Compound (Ia) will be described below.

Compound (I) can be obtained by a method shown by the following reaction formulas 1 and 2 or a similar method to that, and additionally, for example, it can be obtained according to the methods described in JP-A-60-58981, JP-A-61-10580, JP-T 7-503023, WO 93/15071, DE-A-3601411, JP-A-5-70446 and the like, a method similar to these methods and the like.

Respective symbols in the compounds in the following reaction formulas 1 and 2 have the same meanings as those described above. Compounds in the reaction formulas include salts thereof and, as the salts, for example, those similar to the salts of Compound (I) can be mentioned.

[Reaction formula 1]

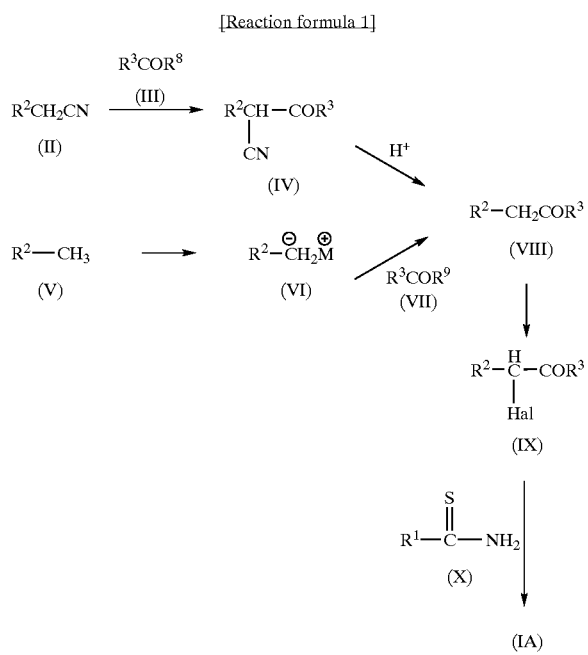

Compounds (II), (III), (V), (VII), (XI), (XIII) and (XIV) can be used as they are when they are commercially s available or can be prepared by a method known per se or according to the similar method to this.

Compound (IV) can be obtained by condensing Compound (II) and Compound (III) in the presence of a base.

In the compound (III), $R^8$ is, for example, (a) $C_{1-6}$ alkoxy (e.g., methoxy, ethoxy and the like), (b) di-$C_{1-6}$ alkylamino (e.g., dimethylamino, diethylamino and the like), (c) N—$C_{6-10}$ aryl-N—$C_{1-6}$ alkylamino (e.g., N-phenyl-N-methylamino and the like), (d) a 3 to 7 membered cyclic amino optionally substituted by $C_{6-10}$ aryl and(or) $C_{1-5}$ alkyl (e.g., pyrrolidino, morpholino, methylaziridin-1-yl and the like) and the like.

An amount of Compound (III) to be used is about 0.5 to about 3.0 moles, preferably about 0.8 to about 2.0 moles relative to 1 mole of Compound (II).

An amount of a base to be used is about 1.0 to about 30 moles, preferably about 1.0 to about 10 moles relative to 1 mole of Compound (II).

As the "base", for example, there are a basic salt such as sodium carbonate, potassium carbonate, cesium carbonate and the like, an inorganic base such as sodium hydroxide, potassium hydroxide and the like, an aromatic amine such as pyridine, lutidine and the like, a tertiary amine such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, an alkali metal hydride such as sodium hydride, potassium hydride and the like, a metal amide such as sodium amide, lithium diisopropylamide, lithium hexamethyldisilazide and the like, a metal alkoxide such as sodium methoxide, sodium ethoxide, potassium tert-butoxide and the like.

It is advantageous that this reaction is conducted without a solvent or in the presence of an inert solvent. Although the solvent is not particularly limited as long as the reaction proceeds, for example, halogenated hydrocarbons, aliphatic hydrocarbons, aromatic hydrocarbons, ethers, amides, alcohols, water or a mixture of two or more of them are used.

A reaction temperature is usually about −5 to about 200° C., preferably about 5 to about 150° C. A reaction time is usually about 5 minutes to about 72 hours, preferably about 0.5 to about 30 hours.

Although the reaction product can be used as the reaction solution itself or as a crude product in the next step, it can be isolated from the reaction mixture according to the conventional method and can be easily purified by a separating means such as recrystallization, distillation, hromatography and the like.

Compound (VIII) can be obtained by treating compound (IV) with an acid.

An amount of an acid to be used is about 1.0 to about 100 moles, preferably about 1.0 to about 30 moles, relative to 1 mole of Compound (IV).

As the "acid", for example, mineral acids such as hydrochloric acid, hydrobromic acid, sulfuric acid and the like are used.

This reaction is conducted in the presence of an inert solvent for a reaction. The solvent is not particularly limited as long as a reaction proceeds but, for example, water, a mixture of water and amides, a mixture of water and alcohols and the like are used.

A reaction temperature is usually about 20 to about 200° C., preferably about 60 to about 150° C. A reaction time is generally about 30 minutes to about 72 hours, preferably about to about 30 hours.

Although the reaction product can be used as the reaction solution itself or as a crude product in the next step, it can be isolated from the reaction mixture according to the conventional method and can be easily purified by a separating means such as recrystallization, distillation, chromatography and the like.

The compound (VIII) can be also obtained by condensing compound (VI) obtained by treating compound (V) with a base, and compound (VII).

In the compound (VI), M represents, for example, an alkali metal such as lithium, sodium, potassium and the like.

In the compound (VII), $R^9$ represents, for example, those similar to the aforementioned $R^8$.

An amount of a base to be used is about 1.0 to about 30 moles, preferably about 1.0 to about 10 moles relative to 1 mole of Compound (V).

As the "base", for example, metal amides such as sodium amide, lithium diisopropylamide, lithium hexamethyldisilazide and the like are used.

It is advantageous that this reaction is conducted without a solvent or in the presence of an inert solvent for a reaction. The solvent is not particularly limited as long as a reaction proceeds but, for example, aliphatic hydrocarbons, aromatic hydrocarbons, ethers or a mixture of two or more of them and the like are used.

A reaction temperature is usually about −78 to about 60° C., preferably about −78 to about 20° C. A reaction time is usually about 5 minutes to about 24 hours, preferably about 0.5 to about 3 hours.

Although a product can be used as the reaction solution itself or as a crude product in the next reaction, it can be isolated from the reaction mixture by the conventional method, and can be easily purified by a separating means such as recrystallization, distillation, chromatography and the like.

Compound (IX) can be obtained by treating Compound (VIII) with halogens. This reaction is performed in the presence of a base or a basic salt if desired.

An amount of halogens to be used is about 1.0 to about 5.0 moles, preferably about 1.0 to about 2.0 moles relative to 1 mole of Compound (VIII).

As the "halogens", there are bromine, chlorine, iodine and the like.

An amount of a base to be used is about 1.0 to about 10.0 moles, preferably about 1.0 to about 3.0 moles relative to 1 mole of Compound (VIII).

As the "base", for example, there are aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like.

An amount of a basic salt to be used is about 1.0 to about 10.0 moles, preferably about 1.0 to about 3.0 moles, relative to 1 mole of Compound (VIII).

As the "basic salt", for example, sodium carbonate, potassium carbonate, cesium carbonate, sodium bicarbonate, sodium acetate, potassium acetate and the like can be used.

It is advantageous that this reaction is performed without a solvent or in the presence of an inert solvent for a reaction. The solvent is not particularly limited as long as a reaction proceeds but, for example, ethers, aromatic hydrocarbons, aliphatic hydrocarbons, amides, halogenated hydrocarbons, nitrites, sulfoxides, organic acids, aromatic amines or a mixture of two or more of them and the like are used.

A reaction temperature is about −20 to about 150° C., preferably about 0 to about 100° C. A reaction time is usually about 5 minutes to about 24 hours, preferably about 10 minutes to about 5 hours.

Although a product can be used as the reaction solution itself or as a crude product in the next reaction, it can be isolated from the reaction mixture by the conventional method, and can be easily purified by a separating means such as recrystallization, distillation, chromatography and the like.

Compound (Ia) can be obtained by condensing Compound (IX) with Compound (X). This reaction is performed in the presence of a base if desired.

In Compound (IX), Hal represents halogens.

When Compound (X) is commercially available, it can be used as it is, or can be obtained by the method known per se or a method according to the known method or further a method shown in the reaction formula 2.

An amount of Compound (X) to be used is about 0.5 to about 3.0 moles, preferably about 0.8 to about 2.0 moles relative to 1 mole of Compound (IX).

An amount of a base to be used is about 1.0 to about 30 moles, preferably about 1.0 to about 10 moles relative to 1 mole of Compound (IX).

As the "base", for example, there are basic salts such as sodium carbonate, potassium carbonate, cesium carbonate, sodium bicarbonate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like.

It is advantageous that this reaction is performed without a solvent or in the presence of an inert solvent for a reaction. The solvent is not particularly limited as long as a reaction proceeds but, for example, halogenated hydrocarbons, aliphatic hydrocarbons, aromatic hydrocarbons, ethers, amides, alcohols, nitrites or a mixture of two or more of them and the like are used.

A reaction temperature is about −5 to about 200° C., preferably about 5 to about 150° C. A reaction time is usually about 5 minutes to about 72 hours, preferably about 0.5 to about 30 hours.

Although a product can be used as the reaction solution itself or as a crude product in the next reaction, it can be isolated from the reaction mixture by the conventional method, and can be easily purified by a separating means such as recrystallization, distillation, chromatography and the like.

[Reaction formula 2]

$$R^{10}CONCS \xrightarrow{R^4H} R^{10}CONH-\overset{S}{\underset{\|}{C}}-R^4$$
(XI) (XII)

$$\downarrow \text{hydrolysis}$$

$$R^1CN$$
(XIII)

$$R^1CONH_2 \xrightarrow[\text{Lawesson's reagent}]{P_4S_{10}} R^1-\overset{O}{\underset{\|}{C}}-NH_2$$
(XIV) (X)

Compound (XII) is obtained by condensing Compound (XI) and amines represented by the formula $R^4H$.

$R^4$ represents "amino group optionally having substituent(s)" represented by the above-mentioned $R^1$.

In Compound (XI), $R^{10}$ represents an alkoxy group. As the "alkoxy group", for example, there are a $C_{1-6}$ alkoxy group such as methoxy, ethoxy, propoxy, isopropoxy, butoxy and the like.

An amount of the "amines" to be used is about 1.0 to about 30 moles, preferably about 1.0 to about 10 moles relative to 1 mole of Compound (XI).

It is advantageous that this reaction is performed without a solvent or in the presence of an inert solvent for a reaction. The solvent is not particularly limited as long as a reaction proceeds but, for example, halogenated hydrocarbons, aliphatic hydrocarbons, aromatic hydrocarbons, ethers, amides, alcohols, nitrites, ketones or a mixture of two or more of them and the like are used.

A reaction temperature is about −5 to about 200° C., preferably about 5 to about 120° C. A reaction time is usually about 5 minutes to about 72 hours, preferably about 0.5 to about 30 hours.

Although a product can be used as the reaction solution itself or as a crude product in the next reaction, it can be isolated from the reaction mixture by the conventional method, and can be easily purified by a separating means such as recrystallization, distillation, chromatography and the like.

Compound (X) is obtained by hydrolysing Compound (XII) using an acid or a base.

An amount of an acid or a base to be used is about 0.1 to about 50 moles, preferably about 1 to about 20 moles relative to 1 mole of Compound (XII), respectively.

As the "acid", for example, mineral acids such as hydrochloric acid, hydrobromic acid, sulfuric acid and the like, Lewis acids such as boron trichloride, boron tribromide and the like, the use of Lewis acid together with thiols or sulfides, organic acids such as trifluoroacetic acid, p-toluenesulfonic acid and the like are used.

As the "base", for example, metal hydroxides such as sodium hydroxide, potassium hydroxide, barium hydroxide and the like, basic salts such as sodium carbonate, potassium carbonate and the like, metal alkoxides such as sodium methoxide, sodium ethoxide, potassium tert-butoxide and the like, organic bases such as triethylamine, imidazole, formamidine and the like are used.

It is advantageous that this reaction is performed without a solvent or in the presence of an inert solvent for a reaction. The solvent is not particularly limited as long as a reaction proceeds but, for example, alcohols, ethers, aromatic hydrocarbons, aliphatic hydrocarbons, halogenated hydrocarbons, sulfoxides, water or a mixture of two or more of them and the like are used.

A reaction time is usually about 10 minutes to about 50 hours, preferably about 30 minutes to about 12 hours. A reaction temperature is about 0 to about 200° C., preferably about 20 to about 120° C.

Compound (X) can be also obtained by treating Compound (XIII) with hydrogen sulfide in the presence of a base.

An amount of hydrogen sulfide is about 1 mole to about 30 moles relative to 1 mole of Compound (XIII).

An amount of a base to be used is about 1.0 to about 30 moles, preferably about 1.0 to about 10 moles relative to 1 mole of Compound (XIII).

As the "base", for example, there are aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like.

It is advantageous that this reaction is performed without a solvent or in the presence of an inert solvent for a reaction. The solvent is not particularly limited as long as a reaction proceeds but, for example, halogenated hydrocarbons, aliphatic hydrocarbons, aromatic hydrocarbons, ethers, aromatic amines or a mixture of two or more of them and the like are used.

This reaction is performed under atmospheric pressure or under pressurized condition. A reaction temperature is usually about −20 to about 80° C., preferably about −10 to about 30° C. A reaction time is usually about 5 minutes to about 72 hours, preferably about 0.5 to about 30 hours.

Although a product can be used as the reaction solution itself or as a crude product in the next reaction, it can be isolated from the reaction mixture by the conventional method, and can be easily purified by a separating means such as recrystallization, distillation, chromatography and the like.

Compound (X) can be also obtained by treating compound (XIII) with O,O-diethyl dithiophosphate in the presence of an acid.

An amount of O,O-diethyl dithiophosphate to be used is about 1 to about 3 moles, preferably about 1 to about 2 moles, relative to 1 mole of Compound (XIII).

An amount of an acid to be used is about 3 to about 10 moles, relative to 1 mole of Compound (XIII).

As the "acid", for example, mineral acids such as hydrogen chloride, hydrogen bromide and the like, and the like are used.

It is advantageous that this reaction is performed without a solvent or in the presence of an inert solvent for a reaction. The solvent is not particularly limited as long as a reaction proceeds but, for example, halogenated hydrocarbons, aliphatic hydrocarbons, aromatic hydrocarbons, ethers, esters, alcohols, water or a mixture of two or more of them and the like are used.

A reaction temperature is generally about −20 to about 80° C., preferably about −10 to about 30° C. A reaction time is generally about 5 minutes to about 72 hours, preferably about 0.5 to about 30 hours.

Although a product can be used as the reaction solution itself or as a crude product in the next reaction, it can be isolated from the reaction mixture by the conventional method, and can be easily purified by a separating means such as recrystallization, distillation, chromatography and the like.

Compound (X) can also be obtained by treating Compound (XIV) with phosphorus pentasulfide or Lawesson's reagent.

An amount of phosphorus pentasulfide or Lawesson's reagent to be used is about 0.5 to about 10 moles, preferably about 0.5 to about 3 moles relative to 1 mole of Compound (XIV).

It is advantageous that this reaction is performed without a solvent or in the presence of an inert solvent for a reaction. The solvent is not particularly limited as long as a reaction proceeds but, for example, ethers, aromatic hydrocarbons, aliphatic hydrocarbons, halogenated hydrocarbons or a mixture of two or more of them and the like are used.

A reaction time is usually 10 minutes to about 50 hours, preferably about 30 minutes to about 12 hours. A reaction temperature is usually about 0 to about 150° C., preferably about 20 to about 120° C.

Although a product (X) can be used as the reaction solution itself or as a crude product in the next reaction, it can be isolated from the reaction mixture by the conventional method, and can be easily purified by a separating means such as recrystallization, distillation, chromatography and the like.

When Compound (Ia) is acylamino compound, an objective compound can be also obtained by subjecting the corresponding amine compound to an acylating reaction known per se.

For example, among Compound (Ia), a compound wherein $R^1$ is acylamino group optionally having substituent(s) is obtained by reacting the corresponding 2-thiazolamine and an acylating agent optionally in the presence of a base or an acid.

An amount of an acylating agent to be used is about 1.0 to about 5.0 moles, preferably about 1.0 to about 2.0 moles relative to 1 mole of the corresponding 2-thiazolamine.

As the "acylating agent", for example, there are carboxylic acids corresponding to an objective acyl group or a reactive derivative thereof (for example, acid halide, acid anhydride, ester and the like) and the like.

An amount of a base or an acid to be used is about 0.8 to about 5.0 moles, preferable about 1.0 to about 2.0 moles relative to 1 mole of the corresponding 2-thiazolamine.

As the "base", for example, there are triethylamine, pyridine, 4-dimethylaminopyridine and the like.

As the "acid", for example, there are methanesulfonic acid, p-toluenesulfonic acid, camphorsulfonic acid and the like.

It is advantageous that this reaction is performed without a solvent or in the presence of an inert solvent for a reaction. The solvent is not particularly limited as long as a reaction proceeds but, for example, ethers, aromatic hydrocarbons, aliphatic hydrocarbons, amides, halogenated hydrocarbons, nitrites, sulfoxides, aromatic amines or a mixture of two or more of them and the like are used.

A reaction temperature is about −20 to about 150° C., preferably about 0 to about 100° C. A reaction time is usually 5 minutes to about 24 hours, preferably about 10 minutes to about 5 hours.

Although a product can be used as the reaction solution itself or as a crude product in the next reaction, it can be isolated from the reaction mixture by the conventional method, and can be easily purified by a separating means such as recrystallization, distillation, chromatography and the like.

When Compound (Ia) is an N-oxide compound, it is obtained by treating the corresponding pyridyl compound with an organic peroxy acid.

An amount of an organic peroxy acid to be used is about 0.8 to about 10 moles, preferable about 1.0 to about 3.0 moles relative to 1 mole of the corresponding pyridyl compound.

As the "organic peroxy acid", for example, there are peracetic acid, trifluoroperacetic acid, m-chloroperbenzoic acid and the like.

It is advantageous that this reaction is performed without a solvent or in the presence of an inert solvent for a reaction. The solvent is not particularly limited as long as a reaction proceeds but, for example, halogenated hydrocarbons, aliphatic hydrocarbons, aromatic hydrocarbons, organic acids, ethers, amides, sulfoxides, alcohols, nitriles, ketones or a mixture of two or more of them and the like are used.

A reaction temperature is about −20 to about 130° C., preferably about 0 to about 100° C. A reaction time is usually 5 minutes to about 72 hours, preferably about 0.5 to about 12 hours.

Alternatively, the N-oxide compound is also obtained by treating the corresponding pyridyl compound with hydrogen peroxide or alkyl hydroperoxide optionally in the presence of a base, an acid or a metal oxide.

An amount of hydrogen peroxide or alkyl hydroperoxide to be used is about 0.8 to about 10 moles, preferably about 1.0 to 3.0 moles relative to 1 mole of the corresponding pyridyl compound.

As the "alkyl hydroperoxide", for example, there are tert-butyl hydroperoxide, cumene hydroperoxide and the like.

An amount of a base, an acid or a metal oxide to be used is about 0.1 to about 30 moles, preferably 0.8 to about 5 moles relative to 1 mole of the corresponding pyridyl compound.

As the "base", for example, there are inorganic bases such as sodium hydroxide, potassium hydroxide and the like, basic salts such as sodium carbonate, potassium carbonate and the like.

As the "acid", for example, there are mineral acids such as hydrochloric acid, sulfuric acid, perchloric acid and the like, Lewis acids such as boron trifluoride, aluminum chloride, titanium tetrachloride and the like, organic acids such as formic acid, acetic acid and the like.

As the "metal oxide", for example, there are vanadium oxide ($V_2O_5$), osmium tetroxide ($OsO_4$), tungsten oxide ($WO_3$), molybdenum oxide ($MoO_3$), selenium dioxide ($SeO_2$), chromium oxide ($CrO_3$) and the like.

It is advantageous that this reaction is performed without a solvent or in the presence of an inert solvent for a reaction. The solvent is not particularly limited as long as a reaction proceeds but, for example, halogenated hydrocarbons, aliphatic hydrocarbons, aromatic hydrocarbons, organic acids, ethers, amides, sulfoxides, alcohols, nitriles, ketones or a mixture of two or more of them and the like are used.

A reaction temperature is about −20 to about 130° C., preferably about 0 to about 100° C. A reaction time is usually 5 minutes to about 72 hours, preferably about 0.5 to about 12 hours.

Although a product can be used as the reaction solution itself or as a crude product in the next reaction, it can be isolated from the reaction mixture by the conventional method, and can be easily purified by a separating means such as recrystallization, distillation, chromatography and the like.

When compound (Ia) is an S-oxide compound, it can be obtained by treating the corresponding sulfide compound with peroxide.

An amount of peroxide to be used is about 0.8 to about 10 moles, preferably about 1.0 to about 3.0 moles, relative to 1 mole of the corresponding sulfide compound.

As the "peroxide", for example, peracetic acid, trifluoroperacetic acid, m-chloroperbenzoic acid, potassium persulfate, metaperiodic acid and the like can be mentioned.

It is advantageous that this reaction is performed without a solvent or in the presence of an inert solvent for a reaction. The solvent is not particularly limited as long as a reaction proceeds but, for example, halogenated hydrocarbons, aliphatic hydrocarbons, aromatic hydrocarbons, organic acids, ethers, amides, sulfoxides, alcohols, nitrites, ketones or a mixture of two or more of them and the like are used.

A reaction temperature is usually about −20 to about 130° C., preferably about 0 to about 100° C. A reaction time is usually about 5 minutes to about 72 hours, preferably about 0.5 to about 12 hours.

In addition, S-oxide compound can be obtained by treating the corresponding sulfide compound with hydrogen peroxide or alkyl hydroperoxide in the presence of a base, acid or metal oxide, if desired.

An amount of hydrogen peroxide or alkyl hydroperoxide to be used is about 0.8 to about 10 moles, preferably about 1.0 to about 3.0 moles, relative to 1 mole of the corresponding sulfide compound.

As the "alkylhydroperoxide", for example, tert-butyl hydroperoxide, cumene hydroperoxide and the like can be mentioned.

An amount of a "base, acid or metal oxide" to be used is about 0.1 to about 30 moles, preferably about 0.8 to about 5 moles, relative to 1 mole of the corresponding sulfide compound.

As the "base", for example, there are inorganic bases such as sodium hydroxide, potassium hydroxide and the like, basic salts such as sodium carbonate, potassium carbonate and the like, and the like.

As the "acid", for example, there are mineral acids such as hydrochloric acid, sulfuric acid, perchloric acid and the like, Lewis acids such as boron trifluoride, aluminum chloride, titanium tetrachloride and the like, organic acids such as formic acid, acetic acid and the like, and the like.

As the "metal oxide", for example, there are vanadium oxide ($V_2O_5$), osmium tetroxide ($OsO_4$), tungsten oxide ($WO_3$), molybdenum oxide ($MoO_3$), selenium dioxide ($SeO_2$), chromium oxide ($CrO_3$) and the like.

It is advantageous that this reaction is performed without a solvent or in the presence of an inert solvent for a reaction. The solvent is not particularly limited as long as a reaction proceeds but, for example, halogenated hydrocarbons, aliphatic hydrocarbons, aromatic hydrocarbons, organic acids, ethers, amides, sulfoxides, alcohols, nitrites, ketones or a mixture of two or more of them and the like are used.

A reaction temperature is usually about −20 to about 130° C., preferably about 0 to about 100° C. A reaction time is usually about 5 minutes to about 72 hours, preferably about 0.5 to about 12 hours.

Although a product can be used as the reaction solution itself or as a crude product in the next reaction, it can be isolated from the reaction mixture by the conventional method, and can be easily purified by a separating means such as recrystallization, distillation, chromatography and the like.

In the above respective reactions, when starting compound s have amino, carboxy, hydroxy as substituents, a protecting groups which are generally used in the peptide chemistry or the like may be introduced into these groups and, after reaction, a desired compound can be obtained by removing protecting groups if needed.

As a protecting group for amino, for example, formyl or $C_{1-6}$ alkyl-carbonyl (for example, acetyl, propionyl and the like), phenylcarbonyl, $C_{1-6}$ alkoxy-carbonyl (for example, methoxycarbonyl, ethoxycarbonyl and the like), phenyloxycarbonyl, $C_{7-10}$ aralkyloxy-carbonyl (for example, benzyloxycarbonyl and the like), trityl, phthaloyl and the like which may have substituent(s), respectively, are used. As these substituent(s), halogen atom(s) (for example, fluorine, chlorine, bromine, iodine and the like), $C_{1-6}$ alkyl-carbonyl (for example, acetyl, propionyl, valeryl and the like), nitro and the like are used and the number of substituents is 1 to 3.

As a protecting group for carboxy, for example, $C_{1-6}$ alkyl (for example, methyl, ethyl, propyl, isopropyl, butyl, tert-butyl and the like), phenyl, trityl, silyl and the like which may have substituent(s), respectively, are used. As these substituent(s), halogen atom(s) (for example, fluorine, chlorine, bromine, iodine and the like), formyl, $C_{1-6}$ alkyl-carbonyl (for example, acetyl, propionyl, butylcarbonyl and the like), nitro, $C_{1-6}$ alkyl (for example, methyl, ethyl, tert-butyl and the like), $C_{6-10}$ aryl (for example, phenyl, naphthyl and the like) and the like are used and the number of substituents is 1 to 3.

As a protecting group for hydroxy, for example, $C_{1-6}$ alkyl (for example, methyl, ethyl, propyl, isopropyl, butyl, tert-butyl and the like), phenyl, $C_{7-11}$ aralkyl (for example, benzyl and the like), forMyl, $C_{1-6}$ alkyl-carbonyl (for example, acetyl, propionyl and the like), phenyloxycarbonyl, $C_{7-11}$ aralkyloxy-carbonyl (for example, benzyloxycarbonyl and the like), tetrahydropyranyl, tetrahydrofuranyl, silyl and the like which may have substituent(s), respectively, are used. As these substituent(s), halogen atom(s) (for example, fluorine, chlorine, bromine, iodine and the like), $C_{1-6}$ alkyl (for example, methyl, ethyl, tert-butyl and the like), $C_{7-11}$ aralkyl (for example, benzyl and the like), $C_{6-10}$ aryl (for example, phenyl, naphthyl and the like), nitro and the like are used and the number of substituents is 1 to 4.

In addition, as a method of removing a protecting group, the method known per se or a method according to this method is used and, for example, method by treating with an acid, a base, the ultraviolet ray, hydrazine, phenylhydrazine, sodium N-methyldithiocarbamate, tetrabutylammonium fluoride, palladium acetate and the like or a method of reduction is used.

In any cases, Compound (I) can be synthesized by further, optionally, performing the known deprotection, acylation, alkylation, hydrogenation, oxidation, reduction, carbon chain extension and substituent exchange reaction alone or in a combination of two or more of them. As these reactions, the reactions described in Shinjikkenkagakukoza 14, vol. 15, 1977 (Maruzen Press) are adopted.

As the above "alcohols", for example, there are methanol, ethanol, propanol, isopropanol, tert-butanol and the like.

As the above "ethers", for example, there are diethyl ether, diisopropyl ether, diphenyl ether, tetrahydrofuran, dioxane, 1,2-dimethoxyethane and the like.

As the above "halogenated hydrocarbons", for example, there are dichloromethane, chloroform, 1,2-dichloroethane, carbon tetrachloride and the like.

As the above "aliphatic hydrocarbons", for example, there are hexane, pentane, cyclohexane and the like.

As the above "aromatic hydrocarbons", for example, there are benzene, toluene, xylene, chlorobenzene and the like.

As the above "aromatic amines", for example, there are pyridine, lutidine, quinoline and the like.

As the above "amides", for example, there are N,N-dimethylformamide, N,N-dimethylacetamide, hexamethylphosphoric triamide and the like.

As the above "ketones", for example, there are acetone, methyl ethyl ketone and the like.

As the above "sulfoxides", for example, there are dimethyl sulfoxide and the like.

As the above "nitriles", for example, there are acetonitrile, propionitrile and the like.

As the above "organic acids", for example, there are acetic acid, propionic acid, trifluoroacetic acid and the like.

As the aforementioned "esters", for example, methyl acetate, ethyl acetate, methyl propionate and the like can be mentioned.

When a desired product is obtained in a free form by the above reaction, it may be converted into a salt according to the conventional method or, when a desired product is obtained as a salt, it can be converted into a free form or another salt according to the conventional method. Compound (I) thus obtained can be isolated and purified from the reaction solution by the known means, for example, transsolvation, concentration, solvent extraction, fractional distillation, crystallization, recrystallization, chromatography and the like.

When Compound (I) is present as a configurational isomer, diastereomer, conformer or the like, each can be optionally isolated by the above separation and purification means. In addition, Compound (I) is in the form of its racemate, they can be separated into S- and R-forms by any conventional optical resolution.

When Compound (I) includes stereoisomers, both the isomers alone and mixtures of each isomers are included in the scope of the present invention.

In addition, Compound (I) may be hydrated or anhydrated.

Compound (I) may be labeled with an isotope (for example, $^3H$, $^{14}C$, $^{35}S$) or the like.

A prodrug of Compound (I) refers to a compound which is converted into Compound (I) by an enzyme, gastric acid or the like under the physiological conditions, that is, a compound which undergoes enzymatic oxidation, reduction, hydrolysis or the like to be converted into Compound (I), and a compound which undergoes hydrolysis or the like by gastric acid or the like to be converted into Compound (I). As a prodrug of Compound (I), there are compounds in which an amino group of Compound (I) is acylated, alkylated or phosphorylated (for example, a compound in which an amino group of Compound (I) is eicosanoylated, alanylated, pentylaminocarbonylated, (5-methyl-2-oxo-1,3-dioxolen-4-yl)methoxycarbonylated, tetrahydrofuranylated, pyrrolidinylmethylated, pivaloyloxymethylated, tert-butylated); a compound in which a hydroxy group of Compound (I) is acylated, alkylated, phosphorylated or boronylated (for example, a compound in which a hydroxy group of Compound (I) is acetylated, palmitoylated, propanoylated, pivaloylated, succinylated, fumarylated, alanylated, dimethylaminomethylcarbonylated); a compound in which a carboxy group of Compound (I) is esterified or amidated (a compound in which a carboxy group of Compound (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3- dioxolen-4-yl)methyl esterified, cyclohexyloxycarbonylethyl esterified, methylamidated); and the like. These compounds can be prepared from Compound (I) by the method known per se.

Alternatively, a prodrug of Compound (I) may be a compound which is converted to Compound (I) under the physiological conditions described in "Iyakuhin no kaihatsu", published by Hirokawashoten in 1990, vol. 7, Melecular Design, pages 163–198.

The Compound (I) of the present invention, a salt thereof and a prodrug thereof (hereinafter to be briefly referred to as compound (I)) have a superior p38 MAP kinase inhibitory activity, a TNF-α inhibitory activity (TNF-α production inhibitory activity, TNF-α action inhibitory activity), phosphodiesterase IV (PDE IV) inhibitory activity and the like, show low toxicity, and cause fewer side effects. Therefore, they are useful as a safe pharmaceutical product, a p38 MAP kinase inhibitor, a TNF-α production inhibitor, a PDE IV inhibitor and the like.

A pharmaceutical composition of the present invention containing Compound (I) shows an excellent p38 MAP kinase inhibitory activity and a TNF-α inhibitory activity and is also excellent in (oral) absorption, (metabolism) stability and the like to a mammal (e.g., mouse, rat, hamster, rabbit, cat, dog, cow, sheep, monkey, human and the like) and, therefore, can be used as an agent for prophylaxis or treatment of p38 MAP kinase related diseases and TNF-α production related diseases, such as asthma, chronic obstructive pulmonary disease (COPD), allergic disease (e.g., allergic dermatitis, allergic rhinitis), atopic dermatitis, inflammation, inflammatory eye disease, Addison's disease, autoimmune hemolytic anemia, systemic lupus erythematosus, Crohn's disease, psoriasis, rheumatism, central nervous disease (e.g., cerebrovascular disease such as cerebral hemorrhage and cerebral infarction, head trauma, spinal cord injury, brain edema, multiple sclerosis and the like), neurodegenerative disease (e.g., Alzheimer's disease, Parkinson's disease, amyotrophic lateral sclerosis (ALS), AIDS encephalopathy), meningitis, diabetes, arthritis (e.g., chronic rheumatoid arthritis, osteoarthritis, rheumatoid-like spondylitis, urarthritis, synovitis), osteoporosis, toxemia (e.g., sepsis, septic shock, endotoxic shocks Gram negative sepsis, toxic shock syndrome), inflammatory bowel disease (e.g., Crohn's disease, ulcerative colitis), inflammatory pulmonary disease (e.g., chronic pneumonia, pulmonary silicosis, pulmonary sarcoidosis, pulmonary tuberculosis) or cachexia (e.g., infectious cachexia, cancerous cachexia, cachexia by acquired immunodeficiency syndrome (AIDS)), arteriosclerosis, Creutzfeldt-Jakob disease, virus infection (e.g., infection with cytomegalovirus, influenzavirus, herpesvirus and the like), angina pectoris, cardiac infarction, congestive heart failure, hepatitis, kidney failure, nephritis, malignant tumor, transplantation, dialysis hypotension, disseminated intravascular coagulation, and the like. Particularly, it can be used for chronic rheumatoid arthritis, osteoarthritis and the like.

The pharmaceutical composition of the present invention containing Compound (I) has a PDE IV inhibitory activity and can be used as a prophylactic or therapeutic agent of diseases caused by inflammation, such as bronchial asthma, chronic obstructive pulmonary disease (COPD), chronic rheumatoid arthritis, autoimmune disease, diabetes, graft versus host disease, multiple sclerosis, sepsis, psoriasis, osteoporosis, depression, central hypergasia after cerebrovascular obstruction, cerebrovascular dementia, Alzheimer's dementia, obesity, cardiac failure and the like.

A pharmaceutical composition of the present invention containing Compound (I) has low toxicity and can be safely administered orally or parenterally (for example, locally, rectally, intravenously or the like) as it is or by mixing Compound (I) with a pharmacologically acceptable carrier into, for example, pharmaceutical preparations such as tablet (including dragee, film coated-tablet and the like), powders, granules, capsules (including soft capsules), solutions, injections, suppositories, sustained releasing preparations and the like according to the method known per se normally used in preparation of pharmaceutical preparations.

A content of Compound (I) or a salt thereof in a pharmaceutical composition of the present invention is about 0.01 to about 100% by weight relative to the whole preparation.

A content of the component other than Compound (I) or a salt thereof in a pharmaceutical composition of the present invention is about 10 to about 99.9% by weight relative to the whole preparation.

The dose is different depending upon an administration subject, route of administration, diseases, condition and the like and the preparation may be orally administered, as a prophylactic or therapeutic agent for p38 MAP kinase related diseases, for example, to a patient with arthritis (body weight about 60 kg), about 0.01 to about 100 mg active ingredient (Compound (I))/kg body weight per day, preferably about 0.01 to about 30 mg/kg body weight per day, more preferably about 1 to about 20 mg/kg body weight per day, which is given once or divided into several doses a day.

As a pharmacologically acceptable carrier which may be used for preparing a preparation of the present invention, there are the conventional various organic or inorganic carriers as a pharmaceutical material, for example, excipient, lubricant, binder and disintegrating agent in solid preparations, or solvent, solubilizing agent, suspending agent, isotonizing agent, buffer and soothing agent in liquid preparations. Further, if needed, additives such as the conventional preservative, antioxidant, colorant, sweetening agent, adsorbing agent, wetting agent and the like can be appropriately used at an appropriate amount.

As an excipient, for example, there are lactose, saccharose, D-mannitol, starch, corn starch, crystalline cellulose, light silicic acid anhydride and the like.

As a lubricant, for example, there are magnesium stearate, calcium stearate, talc, colloidal silica and the like.

As a binder, for example, there are crystalline cellulose, saccharose, D-mannitol, dextrin, hydroxypropylcellulose, hydroxypropylmethylcellulose, polyvinylpyrrolidone, starch, sucrose, gelatin, methylcellulose, sodium carboxymethylcellulose and the like.

As a disintegrating agent, for example, there are starch, carboxymethyl cellulose, calcium carboxymethyl cellulose, sodium carboxymethyl starch, L-hydroxypropylcellulose and the like.

As a solvent, for example, there are water for injection, alcohol, propylene glycol, macrogol, sesame oil, corn oil, olive oil and the like.

As a solubilizing agent, for example, there are polyethylene glycol, propylene glycol, D-mannitol, benzyl benzoate, ethanol, tris-aminomethane, cholesterol, triethanolamine, sodium carbonate, sodium citrate and the like.

As a suspending agent, for example, there are surfactants such as stearyl triethenolamine, sodium lauryl sulfate, lauryl aminopropionate, lecithin, benzalkonium chloride, benzethonium chloride, glyceryl monostearate and the like; hydrophilic polymers such as polyvinyl alcohol, polyvinylpyrrolidone, sodium carboxymethyl cellulose, methylcellulose, hydroxymethylcellulose, hydroxyethylcellulose, hydoxypropylcellulose and the like.

As an isotonizing agent, for example, there are glucose, D-sorbitol, sodium chloride, glycerin, D-mannitol and the like.

As a buffer, for example, there are buffering solutions such as phosphate, acetate, carbonate, citrate and the like.

As a soothing agent, for example, there are benzyl alcohol and the like.

As a preservative, for example, there are p-oxybenzoates, chlorobutanol, benzyl alcohol, phenethyl alcohol, dehydroacetic acid, sorbic acid and the like.

As an antioxidant, for example, there are sulfites, ascorbic acid, α-tocopherol and the like.

The present invention is explained in detail by way of the following Reference Example, Examples, Preparation Examples and Test Examples but these are mere examples and do not limit the present invention and can be varied without departing the scope of the present invention.

"Room temperature" in the following Reference Example and Examples indicates normally about 10° C. to about 35° C. "%" indicates percentage by weight unless otherwise indicated, provided that yield represents mol/mol %.

Abbreviations used elsewhere indicate the following meanings:
s: singlet
d: doublet
t: triplet
q: quartet
dd: double doublet
ddd: double double doublet
dt: double triplet
br: broad
J: coupling constant
Hz: Hertz
CDCl$_3$: deuterated chloroform
$^1$H-NMR: proton nuclear magnetic resonance
Me: methyl The numbers of the sequence in the Sequence Listing in the present specification show the following sequences.
[Sequence No.: 1]
The base sequence of primer P38-U used in Experimental Example 1.
[Sequence No.: 2]
The base sequence of primer PAG-L used in Experimental Example 1.
[Sequence No.: 3]
The base sequence of primer MKK-U used in Experimental Example 1.
[sequence No.: 4]
The base sequence of primer MKK-L used in Experimental Example 1.
[Sequence No.: 5]
The base sequence of primer SER-U used in Experimental Example 1.
[sequence No.: 6]
The base sequence of primer SER-L used in Experimental Example 1.

EXAMPLES

Reference Example 1

1-(4-methoxyphenyl)-2-(3-pyridyl)ethanone

A solution of diisopropylamine (33.2 mL) in anhydrous tetrahydrofuran (300 mL) was cooled to −78° C. and a 1.6 M n-butyllithium/hexane solution (148 mL) was added dropwise with stirring. After completion of dropwise addition, the mixture was stirred for 10 min at the same temperature, and then β-picoline (20 g) was added dropwise. The temperature was raised to −10–0° C., and after stirring for 20 min, a solution of ethyl p-anisate (19.4 g) in anhydrous tetrahydrofuran (40 mL) was added dropwise. After completion of dropwise addition, the mixture was stirred at room temperature for 1 h, and water (100 mL) was added. The organic solvent was evaporated under reduced pressure and an oily product was extracted with ethyl acetate. The extract was washed with water, and after drying, the solvent was evaporated. The remaining crude crystals were recrystallized from ethyl acetate-isopropyl ether to give the title compound (20.8 g, yield 85%). melting point: 71–72° C.

Reference Example 2

In accordance with the above-mentioned Reference Example 1 and respectively using, instead of ethyl p-anisate, ethyl benzoate, ethyl 3,4-dimethoxybenzoate, ethyl 3,4,5-trimethoxybenzoate, ethyl 4-(methoxymethoxy)benzoate, ethyl 4-fluorobenzoate, ethyl 4-ethylbenzoate, ethyl 3,4-methylenedioxybenzoate, methyl 5-indanylcarboxylate, methyl 5,6,7,8-tetrahydro-2-naphthoate, methyl 1,4-benzodioxane-6-carboxylate and methyl 2-naphthoate, the following Reference Example compounds 2-1 to 2-11 were synthesized.

Reference Example compound 2-1: 1-phenyl-2-(3-pyridyl)ethanone
melting point: 44.5-45.5° C.
Reference Example compound 2-2: 1-(3,4-dimethoxyphenyl)-2-(3-pyridyl)ethanone melting point: 114–115° C.
Reference Example compound 2-3:2-(3-pyridyl)-1-(3,4,5-trimethoxyphenyl)ethanone melting point: 104–105° C.
Reference Example compound 2-4: 1-(4-methoxymethoxyphenyl)-2-(3-pyridyl)ethanone melting point: 43–44° C.
Reference Example compound 2-5: 1-(4-fluorophenyl)-2-(3-pyridyl)ethanone oil.
Reference Example compound 2-6: 1-(4-ethylphenyl)-2-(3-pyridyl)ethanone melting point: 80–81° C.
Reference Example compound 2-7: 1-(3,4-methylenedioxyphenyl)-2-(3-pyridyl)ethanone melting point: 98–99° C.
Reference Example compound 2-8: 1-(5-indanyl)-2-(3-pyridyl)ethanone melting point: 55–56° C.
Reference Example compound 2-9: 2-(3-pyridyl)-1-(5,6,7,8-tetrahydro-2-naphthyl)ethanone melting point: 65–66° C.
Reference Example compound 2-10: 1-(1,4-benzodioxan-6-yl)-2-(3-pyridyl)ethanone melting point: 89–90° C.
Reference Example compound 2-11: 1-(2-naphthyl)-2-(3-pyridyl)ethanone melting point: 69–70° C.

Reference Example 3

In accordance with the above-mentioned Reference Example 2 and respectively using α-picoline, γ-picoline and 3,5-lutidine instead of β-picoline, the following Reference Example compounds 3-1 to 3-3 were synthesized.

Reference Example compound 3-1: 1-phenyl-2-(2-pyridyl)ethanone
melting point: 59–60° C.
Reference Example compound 3-2: 1-(4-methoxyphenyl)-2-(2-pyridyl)ethanone melting point: 77–78° C.
Reference Example compound 3-3: 1-phenyl-2-(4-pyridyl)ethanone
melting point: 109–110° C.

Reference Example 4

1-(4-methoxyphenyl)-2-(4-pyridyl)ethanone

A solution of diisopropylamine (33.2 mL) in anhydrous tetrahydrofuran (300 mL) was cooled to −78° C. and 1.6 M n-butyllithium-hexane solution (148 mL) was added dropwise with stirring. After completion of dropwise addition, the mixture was stirred for 10 min at the same temperature, then γ-picoline (20 g) was added dropwise. The temperature was raised to −10–0° C., and after stirring for 20 min, a solution of ethyl p-anisate (19.4 g) in anhydrous tetrahydrofuran (40 mL) was added dropwise. After completion of dropwise addition, the mixture was stirred at room temperature for 1 h, and water (100 mL) was added. The organic solvent was evaporated under reduced pressure and an oily product was extracted with ethyl acetate. The extract was washed with water, and after drying, the solvent was evaporated. the remaining crude crystals were recrystallized from ethyl acetate-isopropyl ether to give the title compound (16.2 g, yield 66%).

melting point: 103–104° C.

Reference Example 5

2-(5-methyl-3-pyridyl)-1-phenylethanone

A solution of diisopropylamine (20.2 mL) in anhydrous tetrahydrofuran (180 mL) was cooled to −78° C., and a 1.6 M n-butyllithium-hexane solution (90 mL) was added dropwise with stirring. After completion of dropwise addition, the mixture was stirred for 10 min at the same temperature, and then 3,5-lutidine (14 g) was added dropwise. The temperature was raised to −10–0° C., and after stirring for 20 min, a solution of ethyl benzoate (9.8 g) in anhydrous tetrahydrofuran (20 mL) was added dropwise. After completion of dropwise addition, the mixture was stirred at room temperature for 1 h, and water (100 mL) was added. The organic solvent was evaporated under reduced pressure and an oily product was extracted with ethyl acetate. The extract was washed with water, and after drying, the solvent was evaporated. The remaining crude crystals were recrystallized from ethyl acetate-isopropyl ether to give the title compound (10 g, yield 70%).

melting point: 53–54° C.

Reference Example 6

2-bromo-1-(4-methoxyphenyl)-2-(3-pyridyl)ethanone hydrobromide 1-(4-Methoxyphenyl)-2-(3-pyridyl)ethanone (6.9 g) was dissolved in acetic acid (36 mL), bromine (1.7 mL) was added, and the mixture was stirred at 80° C. for 3 h. The reaction mixture was cooled with iced water and the precipitated crude crystals were collected by filtration. The crude crystals were recrystallized from ethanol-ethyl ether to give the title compound (10 g, yield 89%).

melting point: 188–95° C.

Reference Example 7

In accordance with the above-mentioned Reference Example 6, 1-phenyl-2-(3-pyridyl)ethanone, 1-(3,4-dimethoxyphenyl)-2-(3-pyridyl)ethanone, 2-(3-pyridyl)-1-(3,4,5-trimethoxyphenyl)ethanone, 1-(4-methoxymethoxyphenyl)-2-(3-pyridyl)ethanone, 1-(4-fluorophenyl)-2-(3-pyridyl)ethanone, 1-phenyl-2-(2-pyridyl)ethanone, 1-(4-methoxyphenyl)-2-(2-pyridyl)ethanone, 1-phenyl-2-(4-pyridyl)ethanone, 1-(4-methoxyphenyl)-2-(4-pyridyl)ethanone, 2-(5-methyl-3-pyridyl)-1-phenylethanone, 1-(4-ethylphenyl)-2-(3-pyridyl)ethanone, 1-(3,4-methylenedioxyphenyl)-2-(3-pyridyl)ethanone, 1-(5-indanyl)-2-(3-pyridyl)ethanone, 2-(3-pyridyl)-1-(5,6,7,8-tetrahydro-2-naphthyl)ethanone, 1-(1,4-benzodioxan-6-yl)-2-(3-pyridyl)ethanone, 1-(2-naphthyl)-2-(3-pyridyl)ethanone and 1-(4-methoxyphenyl)-2-(2-pyridyl)etbanone were respectively used instead of 1-(4-methoxyphenyl)-2-(3-pyridyl)ethanone, the following Reference Example compounds 7-1 to 7-17 were synthesized.

Reference Example compound 7-1: 2-bromo-1-phenyl-2-(3-pyridyl)ethanonehydrobromide melting point: 208–215° C.

Reference Example compound 7-2: 2-bromo-1-(3,4-dimethoxyphenyl)-2-(3-pyridyl)ethanonehydrobromide melting point: 191–193° C.

Reference Example compound 7-3: 2-bromo-2-(3-pyridyl)-1-(3,4,5-trimethoxyphenyl)ethanone hydrobromide melting point: 184–186° C.

Reference Example compound 7-4: 2-bromo-1-(4-hydroxyphenyl)-2-(3-pyridyl)ethanone hydrobromide Used in the next reaction without purification.

Reference Example compound 7-5: 2-bromo-1-(4-fluorophenyl)-2-(3-pyridyl)ethanone hydrobromide melting point: 189–191° C.

Reference Example compound 7-6: 2-bromo-1-phenyl-2-(2-pyridyl)ethanone hydrobromide melting point: 180–181° C.

Reference Example compound 7-7: 2-bromo-1-(4-methoxyphenyl)-2-(2-pyridyl)ethanone hydrobromide melting point: 170–171° C.

Reference Example compound 7-8: 2-bromo-1-phenyl-2-(4-pyridyl)ethanone hydrobromide melting point: 230–232° C.

Reference Example compound 7-9: 2-bromo-1-(4-methoxyphenyl)-2-(4-pyridyl)ethanone hydrobromide melting point: 207–209° C.

Reference Example compound 7-10: 2-bromo-2-(5-methyl-3-pyridyl)-1-phenylethanone hydrobromide melting point: 189–193° C.

Reference Example compound 7-11: 2-bromo-1-(4-ethylphenyl)-2-(3-pyridyl)ethanone hydrobromide melting point: 145–146° C.

Reference Example compound 7-12: 2-bromo-1-(3,4-methylenedioxyphenyl)-2-(3-pyridyl)ethanone hydrobromide melting point: 174–175° C.

Reference Example compound 7-13: 2-bromo-1-(5-indanyl)-2-(3-pyridyl)ethanone hydrobromide melting point: 177–178° C.

Reference Example compound 7-14: 2-bromo-2-(3-pyridyl)-1-(5,6,7,8-tetrahydro-2-naphthyl)ethanone hydrobromide melting point: 160–162° C.

Reference Example compound 7-15: 1-(1,4-benzodioxan-6-yl)-2-bromo-2-(3-pyridyl)ethanone hydrobromide oil.

Reference Example compound 7-16: 2-bromo-1-(2-naphthyl)-2-(3-pyridyl)ethanone hydrobromide melting point: 197–199° C.

Reference Example compound 7-17: 2-bromo-1-(4-methoxyphenyl)-2-(2-pyridyl)ethanone hydrobromide melting point: 170–171° C.

Reference Example 8

[4-(4-methoxyphenyl)-5-(3-pyridyl)-1,3-thiazol-2-yl]amine

To a suspension of thiourea (0.52 g) in acetonitrile (40 mL) was added 2-bromo-1-(4-methoxyphenyl)-2-(3-pyridyl)ethanone hydrobromide (2.5 g) and triethylamine (0.95 mL) was slowly added dropwise with stirring. After completion of dropwise addition, the mixture was stirred at a refluxing temperature for 3 h, and after allowing to cool, the precipitated crystals were collected by filtration. The crystals were washed successively with saturated sodium hydrogencarbonate solution, water, ethanol and ethyl ether and dried. The obtained crude crystals were recrystallized from tetrahydrofuran to give the title compound (1.5 g, yield 90%).

melting point: 265–266° C.

Reference Example 9

N-methyl [4-(4-methoxyphenyl)-5-(3-pyridyl)-1,3-thiazol-2-yl]amine

To a suspension of N-methylthiourea (0.24 g) in acetonitrile (18 mL) was added 2-bromo-1-(4-methoxyphenyl)-2-(3-pyridyl)ethanone hydrobromide (1.0 g) and triethylamine (0.4 mL) was slowly added dropwise with stirring. After completion of dropwise addition, the mixture was stirred at a refluxing temperature for 3 h, and the solvent was evaporated. To the residue was added saturated aqueous sodium hydrogencarbonate and the mixture was extracted with ethyl acetate, and the extract was washed with water and dried, and the solvent was evaporated. The remaining crude crystals were recrystallized from ethyl acetate-isopropyl ether to give the title compound (0.65 g, yield 85%).

melting point: 158–159° C.

Reference Example 10

N-[4-(4-methoxyphenyl)-5-(3-pyridyl)-1,3-thiazol-2-yl]acetamide

Using [(4-methoxyphenyl)-5-(3-pyridyl)-1,3-thiazol-2-yl]amine as a starting compound and according to a method similar to Reference Example 23–128 to be mentioned below, the title compound was obtained (yield 82%).

melting point: 208–210° C.

Reference Example 11

2-(4-acetylpiperazin-1-yl)-4-(4-methoxyphenyl)-5-(3-pyridyl)-1,3-thiazole

In a solution of 1-piperazinecarbothioamide (0.39 g) in acetonitrile (15 mL) was suspended 2-bromo-1-(4-methoxyphenyl)-2-(3-pyridyl)ethanone hydrobromide (1.0 g) and triethylamine (0.4 mL) was slowly added dropwise with stirring. After completion of dropwise addition, the mixture was stirred at a refluxing temperature for 3 h, and the solvent was evaporated. To the residue was added saturated aqueous sodium hydrogencarbonate and the mixture was extracted with ethyl acetate, and the extract was washed with water and dried, and the solvent was evaporated. The residue was dissolved in pyridine (2 mL) and cooled with ice. Acetyl chloride (0.3 mL) was added, and the mixture was left standing at room temperature for 1 h. The reaction mixture was poured into iced water, and the resulting product was extracted with ethyl acetate. The extract was washed with water, and after drying, the solvent was evaporated. The residue was purified by silica gel column chromatography (ethyl acetate-methanol=9:1) to give the title compound (0.30 g, yield 28%). oil.

Reference Example 12

[4-(4-methoxyphenyl)-5-(3-pyridyl)-1,3-thiazol-2-yl]amine hydrochloride

[4-(4-Methoxyphenyl)-5-(3-pyridyl)-1,3-thiazol-2-yl]amine (200 mg) was dissolved in 1% hydrochloric acid-methanol (3.2 mL) and the solvent was evaporated. The obtained crude crystals were recrystallized from methanol-ethyl acetate to give the title compound (180 mg, yield 80%).

melting point: 145–150° C.

The chemical structural formulas of the compounds obtained in Reference Examples 8 to 12 are shown in the following Table 1.

TABLE 1

| Reference Example Compound | $R_a$ | $R_b$ | $R_c$ | additives |
|---|---|---|---|---|
| 8 | —NH$_2$ | 3-pyridyl | 4-MeO-phenyl | |
| 9 | —NHMe | 3-pyridyl | 4-MeO-phenyl | |
| 10 | —NHCOMe | 3-pyridyl | 4-MeO-phenyl | |
| 11 | —N(piperazinyl)-COMe | 3-pyridyl | 4-MeO-phenyl | |

TABLE 1-continued

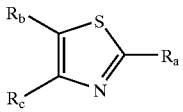

| Reference Example Compound | $R_a$ | $R_b$ | $R_c$ | additives |
|---|---|---|---|---|
| 12 | —NH$_2$ | 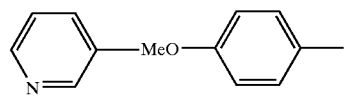 | 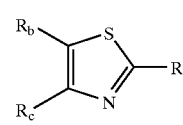—MeO—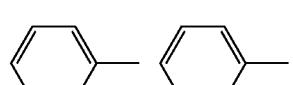 | HCl |

Reference Examaple 13

Reference Example compounds 13-1 to 13-102 shown in the following Tables 2-7 were synthesized in accordance with the methods described in Reference Example 8-12, JP-A-61-10580 and U.S. Pat. No. 4,612,321.

TABLE 2

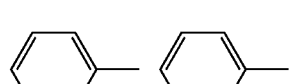

| Reference Example Compound | $R_a$ | $R_b$ | $R_c$ | m.p./° C. |
|---|---|---|---|---|
| 13-1 | —NHMe | 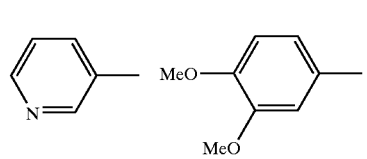 | 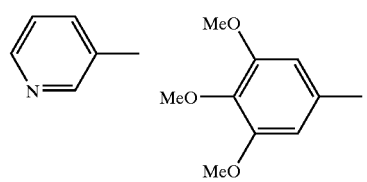 | 168–169 |
| 13-2 | —NH$_2$ | (pyridyl) | (phenyl) | 253–254 |
| 13-3 | —NH$_2$ | (pyridyl) | MeO-substituted phenyl (2,3-diMeO) | 240–241 |
| 13-4 | —NH$_2$ | (pyridyl) | triMeO-substituted phenyl | 168–169 |
| 13-5 | —NHMe | (pyridyl) | F—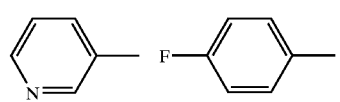 | 157–158 |

TABLE 2-continued
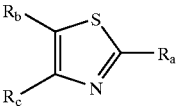
| Reference Example Compound | $R_a$ | $R_b$ | $R_c$ | m.p./° C. |
|---|---|---|---|---|
| 13-6 | —NHMe | 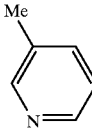 | 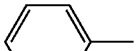 | 205–208 |
| 13-7 | —NH$_2$ |  | 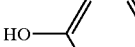 | 266–268 |
| 13-8 | —NHCOCH$_2$COOCH$_2$Me |  | 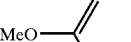 | 201–202 |
| 13-9 | —NHCOCH$_2$COOMe |  | 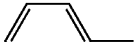 | 185–186 |
| 13-10 | —NH$_2$ |  | 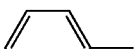 | 236–237 |
| 13-11 | —NHMe |  | 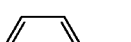 | 215–216 |
| 13-12 | —NHMe |  |  | 214–215 |
| 13-13 | —NH$_2$ |  |  | 217–218 |
| 13-14 | —NH$_2$ |  |  | 282–284 |
| 13-15 | —NH$_2$ |  | 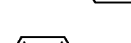 | 248–250 |
| 13-16 | —NHMe |  |  | 177–178 |
| 13-17 | 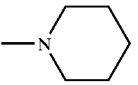 |  |  | 130–131 |
| 13-18 | 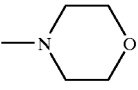 |  | 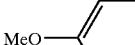 | 134–135 |

TABLE 3

[Thiazole core structure: Rb at position 5, Ra at position 2, Rc at position 4]

| Reference Example Compound | R$_a$ | R$_b$ | R$_c$ | m.p./° C. |
|---|---|---|---|---|
| 13-19 | —CH$_2$Me | 3-pyridyl | 3,4,5-trimethoxyphenyl | 84–84.5 |
| 13-20 | —CH$_2$Me | 3-pyridyl | 4-methoxyphenyl | 59–60 |
| 13-21 | —CH$_2$Me | 3-pyridyl | 4-hydroxyphenyl | 174–175 |
| 13-22 | —Me | 3-pyridyl | 4-methoxyphenyl | 113–114 |
| 13-23 | —CH$_2$Me | 4-pyridyl | phenyl | 83–84 |
| 13-24 | phenyl | 3-pyridyl | phenyl | 135–136 |
| 13-25 | phenyl | 3-pyridyl | 4-methoxyphenyl | 104–105 |
| 13-26 | phenyl | 3-pyridyl | 3,4-dimethoxyphenyl | 96–98 |
| 13-27 | —NH-phenyl | 3-pyridyl | 4-methoxyphenyl | 195–196 |
| 13-28 | —NH-phenyl | 3-pyridyl | 3,4,5-trimethoxyphenyl | 211–213 |
| 13-29 | —NH-phenyl | 3-pyridyl | 4-hydroxyphenyl | 280–282 |

TABLE 3-continued
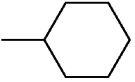
| Reference Example Compound | $R_a$ | $R_b$ | $R_c$ | m.p./° C. |
|---|---|---|---|---|
| 13-30 | 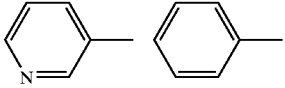 |  | 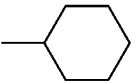 | 100–101 |
| 13-31 | 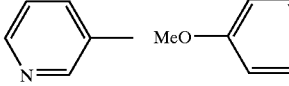 | 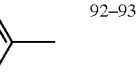 | 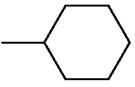 | 92–93 |
| 13-32 | 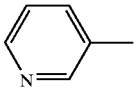 | 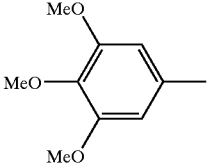 | 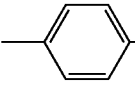 | 111–112 |
| 13-33 | 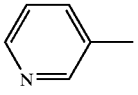 | 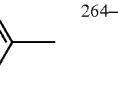 | 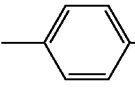 | 264–265 |
| 13-34 | 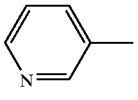 | 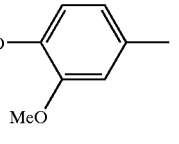 | 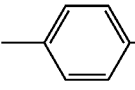 | 245–246 |
| 13-35 | 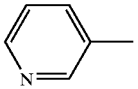 | 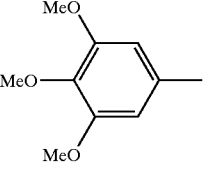 | 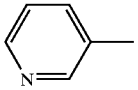 | 247–248 |
TABLE 4
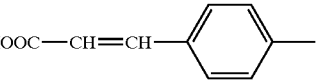
| Reference Example Compound | $R_a$ | $R_b$ | $R_c$ | m.p./° C. |
|---|---|---|---|---|
| 13-36 | —Me | 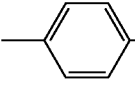 | 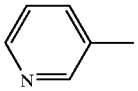 | 208–209 |
| 13-37 | 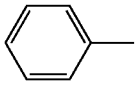 | | | 255–256 |

TABLE 4-continued

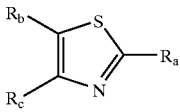

| Reference Example Compound | R$_a$ | R$_b$ | R$_c$ | m.p./° C. |
|---|---|---|---|---|
| 13-38 | 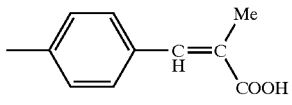 | 3-pyridyl | 3,4-dimethoxyphenyl | 225–226 |
| 13-39 | —(CH$_2$)$_3$COOH | 3-pyridyl | phenyl | 143–144 |
| 13-40 | —(CH$_2$)$_3$COOH | 3-pyridyl | 4-MeO-phenyl | 163–164 |
| 13-41 | —(CH$_2$)$_3$COOH | 5-Me-3-pyridyl | phenyl | 134–135 |
| 13-42 | —(CH$_2$)$_8$COOH | 3-pyridyl | phenyl | 112–113 |
| 13-43 | —(CH$_2$)$_4$OH | 3-pyridyl | phenyl | 51–52 |
| 13-44 | —NHCH$_2$Me | 3-pyridyl | 4-MeO-phenyl | 154–155 |
| 13-45 | —NHMe | 3-pyridyl | 3,4-methylenedioxyphenyl | 187–188 |
| 13-46 | —NHMe | 3-pyridyl | 4-Et-phenyl | 124–125 |
| 13-47 | —NHMe | 4-pyridyl | phenyl | 191–192 |
| 13-48 | —N(CH$_2$Me)$_2$ | 3-pyridyl | 4-MeO-phenyl | oil |
| 13-49 | —NMe$_2$ | 3-pyridyl | 4-MeO-phenyl | oil |

TABLE 4-continued
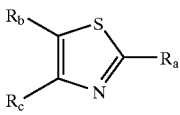
| Reference Example Compound | $R_a$ | $R_b$ | $R_c$ | m.p./° C. |
|---|---|---|---|---|
| 13-50 | —CH$_2$Me | 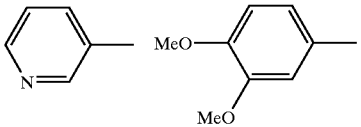 |  | oil |
| 13-51 | —CH$_2$Me | 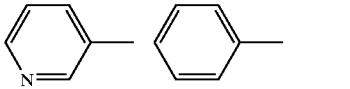 |  | oil |
| 13-52 | —(CH$_2$)$_3$Me | 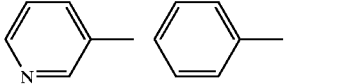 |  | oil |
| 13-53 | —CH$_2$Me | 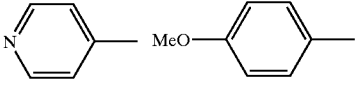 |  | oil |
TABLE 5
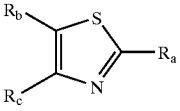
| Reference Example Compound | $R_a$ | $R_b$ | $R_c$ | m.p./° C. |
|---|---|---|---|---|
| 13-54 | 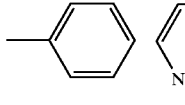 | 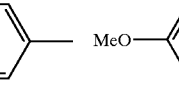 | 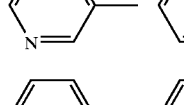 | 104–105 |
| 13-55 | —CH$_2$COOH |  | 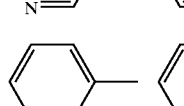 | oil |
| 13-56 | —(CH$_2$)$_3$COOMe |  | 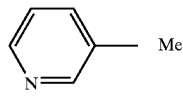 | oil |
| 13-57 | —(CH$_2$)$_5$COOH | 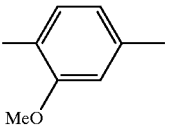 |  | oil |
| 13-58 | —(CH$_2$)$_5$COOH |  |  | oil |

TABLE 5-continued

| Reference Example Compound | R$_a$ | R$_b$ | R$_c$ | m.p./° C. |
|---|---|---|---|---|
| 13-59 | —(CH$_2$)$_4$OH | 3-pyridyl | 4-MeO-phenyl | oil |
| 13-60 | —(CH$_2$)$_6$OH | 3-pyridyl | 4-MeO-phenyl | oil |
| 13-61 | —(CH$_2$)$_2$Me | 3-pyridyl | 4-MeO-phenyl | oil |
| 13-62 | —CHMe$_2$ | 3-pyridyl | 4-MeO-phenyl | oil |
| 13-63 | —NMe$_2$ | 3-pyridyl | 3,4-methylenedioxyphenyl | 76–77 |
| 13-64 | —N(CH$_2$Me)$_2$ | 3-pyridyl | 3,4-methylenedioxyphenyl | 97–98 |
| 13-65 | —NHMe | 4-pyridyl | 3,4-methylenedioxyphenyl | 234–235 |
| 13-66 | —NMe$_2$ | 4-pyridyl | 3,4-methylenedioxyphenyl | 144–145 |
| 13-67 | —NHMe | 3-pyridyl | 3-MeO-phenyl | 146–147 |
| 13-68 | —NHMe | 3-pyridyl | 2-MeO-phenyl | 153–154 |
| 13-69 | —NHMe | 4-pyridyl | 4-F-phenyl | 205–206 |

TABLE 5-continued

[Thiazole structure with Rb at 5-position, Ra at 2-position, Rc at 4-position]

| Reference Example Compound | Ra | Rb | Rc | m.p./° C. |
|---|---|---|---|---|
| 13-70 | —NHMe | 4-pyridyl | 4-Cl-phenyl | 224–225 |
| 13-71 | —NHMe | 4-pyridyl | 4-Br-phenyl | 206–207 |

TABLE 6

[Thiazole structure with Rb at 5-position, Ra at 2-position, Rc at 4-position]

| Reference Example Compound | Ra | Rb | Rc | additives | m.p./° C. |
|---|---|---|---|---|---|
| 13-72 | —NHMe | 4-pyridyl | phenyl | | 191–192 |
| 13-73 | —NHMe | 3-pyridyl | phenyl | | 168–169 |
| 13-74 | —NHMe | 3-pyridyl | indanyl | | 172–173 |
| 13-75 | NHCH₂CH₂-phenyl | 3-pyridyl | 4-MeO-phenyl | | 126–127 |
| 13-76 | —NH-(3-pyridyl) | 3-pyridyl | 4-MeO-phenyl | | 222–223 |
| 13-77 | 2-thienyl | 3-pyridyl | 4-MeO-phenyl | | 132–133 |
| 13-78 | 2-furyl | 3-pyridyl | 4-MeO-phenyl | | 90–91 |
| 13-79 | 4-Cl-phenyl | 3-pyridyl | 4-MeO-phenyl | | 148–149 |

TABLE 6-continued $$\underset{R_c}{\overset{R_b}{\diagup}}\underset{N}{\overset{S}{\diagdown}}R_a$$

| Reference Example Compound | R<sub>a</sub> | R<sub>b</sub> | R<sub>c</sub> | additives | m.p./° C. |
|---|---|---|---|---|---|
| 13-80 | 2,6-di-tert-butyl-4-yl-phenyl OCOMe | 3-pyridyl | 4-MeO-phenyl | | 180–181 |
| 13-81 | 4-COOH-phenyl | 3-pyridyl | 4-F-phenyl | | 240–241 |
| 13-82 | 4-COOH-phenyl | 3-pyridyl | benzo[1,3]dioxol-5-yl | | 258–259 |
| 13-83 | —NMe<sub>2</sub> | 3-pyridyl | indan-5-yl | | 85–86 |
| 13-84 | —N(CH<sub>2</sub>Me)<sub>2</sub> | 3-pyridyl | indan-5-yl | | 56–57 |
| 13-85 | —CH<sub>2</sub>NH<sub>2</sub> | 3-pyridyl | 4-MeO-phenyl | | oil |
| 13-86 | —CH<sub>2</sub>NHMe | 3-pyridyl | 4-MeO-phenyl | | oil |
| 13-87 | —NHCOMe | 3-pyridyl | 4-MeO-phenyl | HCl | 214–217 |
| 13-88 | —NHCOMe | 2-pyridyl | 4-MeO-phenyl | | 228–231 |
| 13-89 | —NHCOMe | 4-pyridyl | 4-MeO-phenyl | HCl | 275–278 |
| 13-90 | —NHCOCH<sub>2</sub>Me | 3-pyridyl | phenyl | HCl | 248–251 |

TABLE 7

![thiazole structure with Rb at 5-position, Ra at 2-position, Rc at 4-position]

| Reference Example Compound | Ra | Rb | Rc | m.p./° C. |
|---|---|---|---|---|
| 13-91 | —NHCOCH₂Me | pyridin-3-yl | 4-MeO-phenyl | 196–199 |
| 13-92 | —NHCOCHMe₂ | pyridin-3-yl | 4-MeO-phenyl | 213–216 |
| 13-93 | —NH₂ | pyridin-3-yl | 4-Me(CH₂)₃O-phenyl | 212–215 |
| 13-94 | —NHCOMe | pyridin-3-yl | 4-Me(CH₂)₃O-phenyl | 230–233 |
| 13-95 | —NH₂ | pyridin-3-yl | 4-(PhCH₂O)-phenyl | 186–189 |
| 13-96 | —NHCOMe | pyridin-3-yl | 4-MeOCO-phenyl | 230–234 |
| 13-97 | —NHCOPh | pyridin-3-yl | 4-MeO-phenyl | 275–278 |
| 13-98 | —NHCOMe | pyridin-3-yl | 4-HO-phenyl | 287–292 |
| 13-99 | —NMeCOMe | pyridin-4-yl | 4-MeO-phenyl | 169–172 |
| 13-100 | —NHCOMe | pyridin-3-yl | phenyl | 222–224 |
| 13-101 | —NHCOMe | pyridin-3-yl | 4-F-phenyl | 175–178 |
| 13-102 | —N=CHNMe₂ | pyridin-3-yl | phenyl | 118–120 |

Reference Example 14

N-(4-chlorobenzoyl)propyleneimine

A solution of propyleneimine (12.3 mL) in tetrahydrofuran (160 mL) was added to 1N aqueous sodium hydroxide solution. To this mixture was added dropwise 4-chlorobenzoyl chloride (25 g) at 0C. After completion of dropwise addition, the mixture was stirred for further 30 min. The reaction mixture was extracted with ethyl acetate. The extract was dried, and the solvent was evaporated to give the title compound (24.9 g, yield 89%). oil.

$^1$H-NMR (CDCl$_3$) δ: 1.39 (3H, d, J=5.5 Hz), 2.15 (1H, d, J=2.9 Hz), 2.51–2.66 (2H, m), 7.39–7.47 (2H, m), 7.93–8.01 (2H, m).

Reference Example 15

In accordance with Reference Example 14, 3-chlorobenzoyl chloride, 2-chlorobenzoyl chloride, 2-methylbenzoyl chloride, 3-methylbenzoyl chloride, 4-methylbenzoyl chloride, 2-methoxybenzoyl chloride, 3-methoxybenzoyl chloride, 4-ethylbenzoyl chloride, 4-(1-methylethyl)benzoyl chloride, 4-(1,1-dimethylethyl)benzoyl chloride, 4-propylbenzoyl chloride, 4-butylbenzoyl chloride, 4-hexylbenzoyl chloride, 4-trifluoromethoxybenzoyl chloride, 4-trifluoromethylbenzoyl chloride, 3,4-dimethoxybenzoyl chloride, 3,4-dimethylbenzoyl chloride, 3,5-dimethylbenzoyl chloride, 3,4-methylenedioxybenzoyl chloride, 2-naphthoyl chloride, 4-fluorobenzoyl chloride and 3-cyclopentyloxy-4-methoxybenzoyl chloride were respectively used instead of 4-chlorobenzoyl chloride, the following Reference Example compounds 15–1 to 15–22 were synthesized.

Reference Example compound 15-1; N-(3-chlorobenzoyl)propyleneimine oil.

$^1$H-NMR (CDCl$_3$) δ: 1.40 (3H, d, J=5.1 Hz), 2.17 (1H, d, J=3.3 Hz), 2.53–2.68 (2H, m), 7.40 (1H, dd, J=8.1, 7.7 Hz), 7.53 (1H, ddd, J=8.1, 2.2, 1.5 Hz), 7.90 (1H, dt, J=7.7, 1.5 Hz), 8.00 (1H, dd, J=2.2, 1.5 Hz).

Reference Example Compound 15-2: N-(2-chlorobenzoyl)propyleneimine oil.

1H-NMR (CDCl$_3$) δ: 1.30 (3H, d, J=5.1 Hz), 2.12 (1H, d, J=3.3 Hz), 2.53 (1H, d, J=5.5 Hz), 2.56–2.68 (1H, m), 7.28–7.48 (3H, m), 7.75–7.81 (1H, m).

Reference Example Compound 15-3: N-(2-methylbenzoyl)propyleneimine oil.

$^1$H-NMR (CDCl$_3$) δ: 1.30 (3H, d, J=5.5 Hz), 2.08 (1H, d, J=3.3 Hz), 2.43–2.57 (5H, m), 7.20–7.31 (2H, m), 7.33–7.43 (1H, m), 7.89 (1H, d, J=7.7 Hz).

Reference Example Compound 15-4: N-(3-methylbenzoyl)propyleneimine oil.

$^1$H-NMR (CDCl$_3$) δ: 1.39 (3H, d, J=5.5 Hz), 2.14 (1H, d, J=3.3 Hz), 2.41 (3H, s), 2.51–2.66 (2H, m), 7.32–7.39 (2H, m), 7.79–7.87 (2H, m).

Reference Example Compound 15-5: N-(4-methylbenzoyl)propyleneimine oil.

$^1$H-NMR (CDCl$_3$) δ: 1.39 (3H, d, J=5.5 Hz), 2.12 (1H, d, J=2.9 HZ), 2.42 (3H, s), 2.50–2.62 (2H, m), 7.25 (2H, d, J=8.1 Hz), 7.92 (2H, d, J=8.1 Hz).

Reference Example Compound 15-6: N-(2-methoxybenzoyl)propyleneimine oil.

$^1$H-NMR (CDCl$_3$) δ: 1.30 (3H, d, J=5.5 Hz), 2.10 (1H, d, J=3.3 Hz), 2.50 (1H, d, J=5.9 Hz), 2.53–2.65 (1H, m), 3.90 (3H, s), 6.95–7.05 (2H, m), 7.41–7.52 (1H, m), 7.81–7.88 (1H, m).

Reference Example Compound 15-7: N-(3-methoxybenzoyl)propyleneimine oil.

$^1$H-NMR (CDCl$_3$) δ: 1.40 (3H, d, J=5.9 Hz), 2.14 (1H, d, J=2.9 Hz), 2.52–2.65 (2H, m), 3.86 (3H, s), 7.10 (1H, ddd, J=8.4, 2.6, 1.1 Hz), 7.37 (1H, dd, J=8.4, 7.3 Hz), 7.55 (1H, dd, J=2.6, 1.5 Hz), 7.63 (1H, ddd, J=7.3, 1.5, 1.1 Hz).

Reference Example Compound 15-8: N-(4-ethylbenzoyl)propyleneimine oil.

$^1$H-NMR (CDCl$_3$) δ: 1.27 (3H, t, J=7.6 Hz), 1.39 (3H, d, J=5.5 Hz), 2.13 (1H, d, J=3.3 Hz), 2.50–2.61 (2H, m), 2.71 (2H, q, J=7.6 Hz), 7.28 (2H, d, J=7.7 Hz), 7.95 (2H, d, J=7.7 Hz).

Reference Example Compound 15-9: N-[4-(1-methylethyl)benzoyl]propyleneimine oil.

$^1$H-NMR (CDCl$_3$) δ: 1.28 (6H, d, J=7.0 Hz), 1.40 (3H, d, J=5.5 Hz), 2.13 (1H, d, J=3.3 Hz), 2.50–2.64 (2H, m), 2.90–3.05 (1H, m), 7.31 (2H, d, J=8.2 Hz), 7.96 (2H, d, J=8.2 Hz).

Reference Example Compound 15-10: N-[4-(1,1-dimethylethyl)benzoyl]propyleneimine A solution of propyleneimine (11 mL, 0.14 mol) in tetrahydrofuran (160 mL) was added to 2N aqueous sodium hydroxide solution (70 mL). To this mixture was added dropwise 4-(1,1-dimethylethyl)benzoyl chloride (25 g, 0.13 mol) at 0° C. After completion of dropwise addition, the mixture was stirred further for 30 min. The reaction mixture was extracted with ethyl acetate. The extract was dried, and the solvent was evaporated to give the title compound (27 g, 0.13 mol, yield 99%). oil.

$^1$H-NMR (CDCl$_3$)δ: 1.35 (9H, s), 1.41 (3H, d, J=5.5 Hz), 2.12 (1H, d, J=2.9 Hz), 2.51–2.64 (2H, m), 7.47 (2H, d, J=8.8 Hz), 7.96 (2H, d, J=8.8 Hz).

Reference Example Compound 15-11: N-(4-propylbenzoyl)propyleneinine oil.

$^1$H-NMR (CDCl$_3$) δ: 0.96 (3H, t, J=7.3 Hz), 1.39 (3H, d, J=5.5 Hz), 1.57–1.75 (2H, m), 2.12 (1H, d, J=3.3 Hz), 2.50–2.59 (2H, m), 2.65 (2H, t, J=7.7 Hz), 7.26 (2H, d, J=8.1 Hz), 7.94 (2H, d, J=8.1 Hz).

Reference Example Compound 15-12: N-(4-butylbenzoyl)propyleneimine oil.

$^1$H-NMR (CDCl$_3$) δ: 0.94 (3H, t, J=7.1 Hz), 1.26–1.47 (5H, m), 1.54–1.73 (2H, m), 2.12 (1H, d, J=2.9 Hz), 2.51–2.62 (2H, m), 2.67 (2H, t, J=7.7 Hz), 7.26 (2H, d, J=8.1 Hz), 7.94 (2H, d, J=8.1 Hz).

Reference Example Compound 15-13: N-(4-hexylbenzoyl)propyleneimine oil.

$^1$H-NMR (CDCl$_3$) δ: 0.89 (3H, t, J=6.6 Hz), 1.24–1.38 (6H, m), 1.39 (3H, d, J=5.5 Hz), 1.56–1.68 (2H, m), 2.12 (1H, d, J=3.3 Hz), 2.51–2.61 (2H, m), 2.66 (2H, t, J=7.7 Hz), 7.26 (2H, d, J=8.1 Hz), 7.94 (2H, d, J=8.1 Hz).

Reference Example Compound 15-14: N-(4-trifluoromethoxybenzoyl)propyleneimine oil.

$^1$H-NMR (CDCl$_3$) δ: 1.40 (3H, d, J=5.5 Hz), 2.16 (1H, d, J=3.3 Hz), 2.53–2.68 (2H, m), 7.29 (2H, d, J=9.0 Hz), 8.08 (2H, d, J=9.0 Hz).

Reference Example Compound 15-15: N-(4-trifluoromethylbenzoyl)propyleneimine oil.

$^1$H-NMR (CDCl$_3$) δ:1.40 (3H, d, J=5.5 Hz), 2.19 (1H, d, J=3.7 Hz), 2.54–2.70 (2H, m), 7.73 (2H, d, J=8.0 Hz), 8.13 (2H, d, J=8.0 Hz).

Reference Example Compound 15-16: N-(3,4-dimethoxybenzoyl)propyleneimine oil.

$^1$H-NMR (CDCl$_3$) δ: 1.41 (3H, d, J=5.5 Hz), 2.12 (1H, d, J=3.3 Hz), 2.51–2.63 (2H, m), 3.94 (3H, s), 3.95 (3H, s), 6.92 (1H, d, J=8.5 Hz), 7.56 (1H, d, J=2.2 Hz), 7.69 (1H, dd, J=8.5, 2.2 Hz).

Reference Example Compound 15-17: N-(3,4-dimethylbenzoyl)propyleneimine oil.

$^1$H-NMR (CDCl$_3$) δ: 1.39 (3H, d, J=5.5 Hz), 2.12 (1H, d, J=3.3 Hz), 2.32 (6H, s), 2.49–2.61 (2H, m), 7.21 (1H, d, J=7.7 Hz), 7.77 (1H, dd, J=7.7, 1.8 Hz), 7.80 (1H, d, J=1.8 Hz).

Reference Example Compound 15-18: N-(3,5-dimethylbenzoyl)propyleneimine 3,5-Dimethylbenzoic acid (25 g, 0.17 mol) and dimethylformamide (0.1 mL) were added to thionyl chloride (50 mL) at 0° C. The mixture was refluxed under heating for 2 h. The excess thionyl chloride was evaporated under reduced pressure and to the residue was added toluene (50 mL). Toluene was evaporated under reduced pressure to give oily 3,5-dimethylbenzoyl chloride. A solution of propyleneimine (14 mL, 0.18 mol) in tetrahydrofuran (160 mL) was added to 1N aqueous sodium hydroxide solution (180 mL). 3,5-Dimethylbenzoyl chloride was added dropwise to this mixture at 0° C. After completion of dropwise addition, the mixture was stirred further for 30 min. The reaction mixture was extracted with ethyl acetate. The extract was dried, and the solvent was evaporated to give the title compound (31 g, 0.16 mol, yield 99%). oil.

$^1$H-NMR (CDCl$_3$)δ: 1.39 (3H, d, J=5.5 Hz), 2.13 (1H, d, J=3.7 Hz), 2.37 (6H, s), 2.47–2.62 (2H, m), 7.19 (1H, s), 7.64 (2H, s).

Reference Example Compound 15-19: N-(3,4-methylenedioxybenzoyl)propyleneimine oil.

$^1$H-NMR (CDCl$_3$) δ: 1.38 (3H, d, J=4.9 Hz), 2.11 (1H, d, J=3.1 Hz), 2.48–2.64 (2H, m), 6.05 (2H, s), 6.86 (1H, d, J=8.2 Hz), 7.48 (1H, d, J=1.7 Hz), 7.65 (1H, dd, J=8.2, 1.7 Hz).

Reference Example Compound 15-20: N-(2-naphthoyl)propyleneimine oil.

$^1$H-NMR (CDCl$_3$) δ: 1.44 (3H, d, J=5.5 Hz), 2.22 (1H, d, J=3.3 Hz), 2.57–2.84 (2H, m), 7.50–7.65 (2H, m), 7.85–8.00 (3H, m), 8.06 (1H, dd, J=8.6, 1.5 Hz), 8.59 (1H, s).

Reference Example Compound 15-21: N-(4-fluorobenzoyl)propyleneimine oil.

$^1$H-NMR (CDCl$_3$) δ: 1.39 (3H, d, J=5.2 Hz), 2.14–2.15 (1H, m), 2.52–2.63 (2H, m), 7.08–7.19 (2H, m), 8.00–8.10 (2H, m).

Reference Example Compound 15-22: N-(3-cyclopentyloxy-4-methoxybenzoyl)propyleneimine oil.

$^1$H-NMR (CDCl$_3$) δ: 1.40 (3H, d, J=5.1 Hz), 1.54–1.68 (2H, m), 1.73–2.06 (6H, m), 2.11 (1H, d, J=3.3 Hz), 2.51–2.63 (2H, m), 3.91 (3H, s), 4.79–4.90 (1H, m), 6.90 (1H, d, J=8.4 Hz), 7.55 (1H, d, J=1.8 Hz), 7.65 (1H, dd, J=8.4, 1.8 Hz).

Reference Example 16

1-(2-chlorophenyl)-2-(4-pyridyl)ethanone

A solution of diisopropylamine (15 mL) in anhydrous tetrahydrofuran (100 mL) was cooled at −50° C. and 1.6 M n-butyllithium/hexane solution (69 mL) was added dropwise with stirring. After completion of dropwise addition, the mixture was stirred for 10 min and a solution of γ-picoline (20 g) in anhydrous tetrahydrofuran (10 mL) was added dropwise at −30° C. The mixture was stirred for 1 h and a solution of N-(2-chlorobenzoyl)propyleneimine (20 g) in anhydrous tetrahydrofuran (10 mL) was added dropwise at −10° C. After completion of dropwise addition, the mixture was stirred for at room temperature for 2 h. To the reaction mixture was added water (100 mL) and the mixture was extracted with ethyl acetate. The extract was washed with water, and after drying, the solvent was evaporated. The residue was purified by silica gel column chromatography (hexane-ethyl acetate=1:1) to give the title compound (16 g, yield 71%). oil.

$^1$H-NMR (CDCl$_3$) δ: 4.28 (2H, s), 7.20 (2H, d, J=6.2 Hz), 7.28–7.39 (1H, m), 7.41–7.48 (3H, m), 8.56 (2H, d, J=6.2 Hz).

Reference Example 17

In accordance with Reference Example 16, N-(3-chlorobenzoyl)propyleneimine, N-(4-chlorobenzoyl)propyleneimine, N-(2-methylbenzoyl)propyleneimine, N-(3-methylbenzoyl)propyleneimine, N-(4-methylbenzoyl)propyleneimine, N-(2-methoxybenzoyl)propyleneimine, N-(3-methoxybenzoyl)propyleneimine, N-(4-ethylbenzoyl)propyleneimine, N-[4-(1-methylethyl)benzoyl]propyleneimine, N-[4-(1,1-dimethylethyl)benzoyl]propyleneimine, N-(4-propylbenzoyl)propyleneimine, N-(4-butylbenzoyl)propyleneimine, N-(4-hexylbenzoyl)propyleneimine, N-(4-trifluoromethoxybenzoyl)propyleneimine, N-(4-trifluoromethylbenzoyl)propyleneimine, N-(3,4-dimethoxybenzoyl)propyleneimine, N-(3,4-dimethylbenzoyl)propyleneimine, N-(3,5-dimethylbenzoyl)propyleneimine, N-(3,4-methylenedioxybenzoyl)propyleneimine, N-(2-naphthoyl)propyleneimine and N-(3-cyclopentyloxy-4-methoxybenzoyl)propyleneimine, instead of N-(2-chlorobenzoyl)propyleneimine, the following Reference Example compounds 17-1 to 17-21 were synthesized.

Reference Example Compound 17-1: 1-(3-chlorophenyl)-2-(4-pyridyl)ethanone
melting point: 79–80° C.

Reference Example Compound 17-2: 1-(4-chlorophenyl)-2-(4-pyridyl)ethanone
melting point: 93–94° C.

Reference Example Compound 17-3: 1-(2-methylphenyl)-2-(4-pyridyl)ethanone oil.

$^1$H-NMR (CDCl$_3$) δ: 2.48 (3H, s), 4.23 (2H, s), 7.19 (2H, d, J=6.2 Hz), 7.24–7.47 (3H, m), 7.73 (1H, d, J=7.7 Hz), 8.56 (2H, d, J=6.2 Hz).

Reference Example Compound 17-4: 1-(3-methylphenyl)-2-(4-pyridyl)ethanone
melting point: 115–116° C.

Reference Example Compound 17-5: 1-(4-methylphenyl)-2-(4-pyridyl)ethanone
melting point: 110–111° C.

Reference Example Compound 17-6: 1-(2-methoxyphenyl)-2-(4-pyridyl)ethanone oil.

$^1$H-NMR (CDCl$_3$) δ: 3.92 (3H, s), 4.30 (2H, s), 6.95–7.07 (2H, m), 7.17 (2H, d, J=5.9 Hz), 7.50 (1H, ddd, J=8.4, 7.3, 1.8 Hz), 7.73 (1H, dd, J=7.7, 1.8 Hz), 8.53 (2H, d, J=5.9 Hz).

Reference Example Compound 17-7: 1-(3-methoxyphenyl)-2-(4-pyridyl)ethanone oil.

$^1$H-NMR (CDCl$_3$) δ: 3.86 (3H, s), 4.28 (2H, s), 7.14 (1H, ddd, J=8.1, 2.6, 1.1 Hz), 7.20 (2H, d, J=6.2 Hz), 7.36 (1H, dd, J=8.1, 7.7 Hz), 7.51 (1H, dd, J=2.6, 1.5 Hz), 7.58 (1H, ddd, J=7.7, 1.5, 1.1 Hz), 8.57 (2H, d, J=6.2 Hz).

Reference Example Compound 17-8: 1-(4-ethylphenyl)-2-(4-pyridyl)ethanone
melting point: 87–89° C.

Reference Example Compound 17-9: 1-[4-(1-methylethyl)phenyl]-2-(4-pyridyl)ethanone.
melting point: 86–88° C.

Reference Example Compound 17-10: 1-[4-(1,1-dimethylethyl)phenyl]-2-(4-pyridyl)ethanone A solution of diisopropylamine (15 mL, 0.11 mol) in anhydrous tetrahydrofuran (100 mL) was cooled to −50° C., 1.6 M n-butyllithium-hexane solution (69 mL, 0.11 mol) was added dropwise with stirring. After completion of dropwise addition, the mixture was stirred for 10 min, and then a solution of γ-picoline (9.3 g, 0.10 mol) in anhydrous tetrahydrofuran (10 mL) was added dropwise at −30° C. The mixture was stirred for 1 h, a solution of N-[4-(1,1-dimethylethyl)benzoyl]propyleneimine (22 g, 0.10 mol) in anhydrous tetrahydrofuran (10 mL) was added dropwise at -30° C. After completion of dropwise addition, the temperature of the mixture was increased gradually to room temperature and the mixture was stirred for 2 h. To the reaction mixture was added water (100 mL), the mixture was extracted with ethyl acetate. The extract was washed with water, and after drying, the solvent was evaporated. The residue was purified by silica gel column chromatography (hexane-ethyl acetate, 1:1) and recrystallized from diisopropyl ether-hexane to give the title compound (11 g, yield 43%).

melting point: 75–76° C.
Reference Example Compound 17-11: 1-(4-propylphenyl)-2-(4-pyridyl)ethanone
melting point: 71–72° C.
Reference Example Compound 17-12: 1-(4-butylphenyl)-2-(4-pyridyl)ethanone
melting point: 41–43° C.
Reference Example Compound 17-13: 1-(4-hexylphenyl)-2-(4-pyridyl)ethanone
melting point: 57–58° C.
Reference Example Compound 17-14: 2-(4-pyridyl)-1-(4-trifluoromethoxyphenyl)ethanone
melting point: 65–66° C.
Reference Example Compound 17-15: 2-(4-pyridyl)-1-(4-trifluoromethylphenyl)ethanone
melting point: 94–95° C.
Reference Example Compound 17-16: 1-(3,4-dimethoxyphenyl)-2-(4-pyridyl)ethanone
melting point: 110–111° C.
Reference Example Compound 17-17: 1-(3,4-dimethylphenyl)-2-(4-pyridyl)ethanone
melting point: 81–83° C.
Reference Example Compound 17-18

1-(3,5-dimethylphenyl)-2-(4-pyridyl)ethanone

A solution of diisopropylamine (15 mL, 0.11 mol) in anhydrous tetrahydrofuran (100 mL) was cooled to –50° C., 1.6 M n-butyllithium-hexane solution (69 mL, 0.11 mol) was added dropwise with stirring. After completion of dropwise addition, the mixture was stirred for 10 min, and a solution of γ-picoline (9.3 g, 0.10 mol) in anhydrous tetrahydrofuran (10 mL) was added dropwise at –30° C. The mixture was stirred for 1 h, a solution of N-(3,5-dimethylbenzoyl)propyleneimine (19 g, 0.10 mol) in anhydrous tetrahydrofuran (10 mL) was added dropwise at –30° C. After completion of dropwise addition, the temperature of the mixture was gradually raised to room temperature and the mixture was stirred for 2 h. To the reaction mixture was added water (100 mL) and the mixture was extracted with ethyl acetate. The extract was washed with water, and after drying, the solvent was evaporated. The residue was crystallized from diisopropyl ether-hexane to give the title compound (13 g, yield 58%).

melting point: 90–91° C.
Reference Example Compound 17-19: 1-(3,4-methylenedioxyphenyl)-2-(4-pyridyl)ethanone
melting point: 126–127° C.
Reference Example Compound 17-20: 1-(2-naphthyl)-2-(4-pyridyl)ethanone
melting point: 114–115° C.
Reference Example Compound 17-21: 1-(3-cyclopentyloxy-4-methoxyphenyl)-2-(4-pyridyl)ethanone
melting point: 87–89° C.

Reference Example 18

In accordance with Reference Example 17, the following Reference Example compound 18-1–18-9 were synthesized using γ-picoline instead of β-picoline.

Reference Example Compound 18-1: 1-(2-chlorophenyl)-2-(3-pyridyl)ethanone oil.
$^1$H-NMR (CDCl$_3$) δ: 4.28 (2H, s), 7.18–7.49 (5H, m), 7.59–7.67 (1H, m), 8.47–8.56 (2H, m).
Reference Example Compound 18-2: 1-(3-chlorophenyl)-2-(3-pyridyl)ethanone oil.
$^1$H-NMR (CDCl$_3$) δ: 4.29 (2H, s), 7.25–7.34 (1H, m), 7.44 (1H, t, J=7.7 Hz), 7.54–7.63 (2H, m), 7.90 (1H, dt, J=7.7, 1.5 Hz), 8.00 (1H, dd, J=1.8, 1.5 Hz), 8.49–8.57 (2H, m).
Reference Example Compound 18-3: 1-(4-chlorophenyl)-2-(3-pyridyl)ethanone
$^1$H-NMR (CDCl$_3$) δ: 4.27 (2H, s), 7.24–7.31 (1H, m), 7.47 (2H, d, J=8.8 Hz), 7.55–7.63 (1H, m), 7.96 (2H, d, J=8.8 Hz), 8.46–8.53 (2H, m).
Reference Example Compound 18-4: 1-(2-methylphenyl)-2-(3-pyridyl)ethanone oil.
$^1$H-NMR (CDCl$_3$) δ: 2.47 (3H, s), 4.23 (2H, s), 7.18–7.47 (5H, m), 7.73 (1H, d, J=7.7 Hz), 8.47–8.56 (2H, m).
Reference Example Compound 18-5: 1-(3-methylphenyl)-2-(3-pyridyl)ethanone oil.
$^1$H-NMR (CDCl$_3$) δ: 2.43 (3H, s), 4.29 (2H, s), 7.17–7.36 (1H, m), 7.36–7.46 (2H, m), 7.58–7.65 (1H, m), 7.78–7.86 (2H, m), 8.50–8.56 (2H, m).
Reference Example Compound 18-6: 1-(4-methylphenyl)-2-(3-pyridyl)ethanone
melting point: 72–74° C.
Reference Example Compound 18-7: 1-(3-methoxyphenyl)-2-(3-pyridyl)ethanone oil.
$^1$H-NMR (CDCl$_3$) δ: 3.86 (3H, s), 4.29 (2H, s), 7.14 (1H, ddd, J=8.1, 2.6, 1.8 Hz), 7.28 (1H, dd, J=7.3, 4.8 Hz), 7.40 (1H, dd, J=8.1, 7.7 Hz), 7.53 (1H, dd, J=2.6, 1.8 Hz), 7.58–7.65 (2H, m), 8.50–8.55 (2H, m).
Reference Example Compound 18-8: 1-[4-(1,1-dimethylethyl)phenyl]-2-(3-pyridyl)ethanone oil.
$^1$H-NMR (CDCl$_3$) δ: 1.34 (9H, s), 4.28 (2H, s), 7.22–7.31 (1H, m), 7.50 (2H, d, J=8.4 Hz), 7.56–7.65 (1H, m), 7.96 (2H, d, J=8.4 Hz), 8.48–8.55 (2H, m).
Reference Example Compound 18-9: 1-(3,5-dimethylphenyl)-2-(3-pyridyl)ethanone oil.
$^1$H-NMR (CDCl$_3$) δ: 2.38 (6H, s), 4.27 (2H, s), 7.24–7.30 (2H, m), 7.58–7.63 (3H, m), 8.50–8.52 (2H, m).

Reference Example 19

In accordance with Reference Example 1, the following Reference Example compound 19 was synthesized using ethyl 4-dimethylaminobenzoate instead of ethyl p-anisate.
Reference Example Compound 19: 1-(4-dimethylaminophenyl)-2-(4-pyridyl)ethanone
melting point: 189–192° C.

Reference Example 20

1-(4-fluorophenyl)-2-(4-pyridyl)ethanone

A solution of diisopropylamine (29 mL) in anhydrous tetrahydrofuran (300 mL) was cooled to –78° C., and 1.6 M n-butyllithium/hexane solution (140 mL) was added dropwise with stirring. After completion of dropwise addition, the mixture was stirred for 10 min, and then a solution of γ-picoline (21 g) in anhydrous tetrahydrofuran (50 mL) was added. The reaction mixture was stirred at –10° C. for 30 min. The reaction solution was cooled to –78° C. and a solution of N-(4-fluorobenzoyl)propyleneimine (36 g) in anhydrous tetrahydrofuran (50 mL) was added dropwise. After completion of dropwise addition, the mixture was stirred at room temperature for 3 h. To the reaction mixture was added water (100 mL) and extracted with ethyl acetate.

The extract was washed with water, and after drying, the solvent was evaporated. The residue was crystallized from diisopropyl ether to give the title compound (28 g, yield 66%).

melting point: 90–91° C.

Reference Example 21

4-(methylthio)thiobenzamide

4-Methylthiobenzonitrile (12 g) was dissolved in a solution (130 mL) of 4N hydrogen chloride in ethyl acetate. To this solution was added O,O-diethyl dithiophosphate (15 mL) and the mixture was stirred at room temperature for 22 h. To the reaction mixture was added water (100 mL), and the mixture was extracted with ethyl acetate. The insoluble material was filtered off and the filtrate was washed with saturated brine, dried and the solvent was evaporated. The residue was recrystallized from ethyl acetate to give the title compound (10 g, yield 67%).

melting point: 176–178° C.

Reference Example 22

In accordance with Reference Example 6 and respectively using 1-(2-chlorophenyl)-2-(3-pyridyl)ethanone, 1-(3-chlorophenyl)-2-(3-pyridyl)ethanone, 1-(4-chlorophenyl)-2-(3-pyridyl)ethanone, 1-(2-methylphenyl)-2-(3-pyridyl)ethanone, 1-(3-methylphenyl)-2-(3-pyridyl)ethanone, 1-(4-methylphenyl)-2-(3-pyridyl)ethanone, 1-(3-methoxyphenyl)-2-(3-pyridyl)ethanone, 1-[4-(1,1-dimethylethyl)phenyl]-2-(3-pyridyl)ethanone, 1-(3,5-dimethylphenyl)-2-(3-pyridyl)ethanone, 1-(2-chlorophenyl)-2-(4-pyridyl)ethanone, 1-(3-chlorophenyl)-2-(4-pyridyl)ethanone, 1-(4-chlorophenyl)-2-(4-pyridyl)ethanone, 1-(2-methylphenyl)-2-(4-pyridyl)ethanone, 1-(3-methylphenyl)-2-(4-pyridyl)ethanone, 1-(4-methylphenyl)-2-(4-pyridyl)ethanone, 1-(2-methoxyphenyl)-2-(4-pyridyl)ethanone, 1-(3-methoxyphenyl)-2-(4-pyridyl)ethanone, 1-(4-ethylphenyl)-2-(4-pyridyl)ethanone, 1-[4-(1-methylethyl)phenyl]-2-(4-pyridyl)ethanone, 1-[4-(1,1-dimethylethyl)phenyl]-2-(4-pyridyl)ethanone, 1-(4-propylphenyl)-2-(4-pyridyl)ethanone, 1-(4-butylphenyl)-2-(4-pyridyl)ethanone, 1-(4-hexylphenyl)-2-(4-pyridyl)ethanone, 2-(4-pyridyl)-1-(4-trifluoromethoxyphenyl)ethanone, 2-(4-pyridyl)-1-(4-trifluoromethylphenyl)ethanone, 1-(4-dimethylaminophenyl)-2-(4-pyridyl)ethanone hydrobrbmide, 1-(3,4-dimethoxyphenyl)-2-(4-pyridyl)ethanone, 1-(3,4-dimethylphenyl)-2-(4-pyridyl)ethanone, 1-(3,5-dimethylphenyl)-2-(4-pyridyl)ethanone, 1-(3,4-methylenedioxyphenyl)-2-(4-pyridyl)ethanone, 1-(2-naphthyl)-2-(4-pyridyl)ethanone, 1-(4-fluorophenyl)-2-(4-pyridyl)ethanone and 1-(3-cyclopentyloxy-4-methoxyphenyl)-2-(4-pyridyl)ethanone instead of 1-(4-methoxyphenyl)-2-(3-pyridyl)ethanone, the following Reference Example compounds 22-1 to 22-33 were synthesized.

Reference Example Compound 22-1: 2-bromo-1-(2-chlorophenyl)-2-(3-pyridyl)ethanone hydrobromide
melting point: 88–90° C.

Reference Example Compound 22-2: 2-bromo-1-(3-chlorophenyl)-2-(3-pyridyl)ethanone hydrobromide
melting point: 164–166° C.

Reference Example Compound 22-3: 2-bromo-1-(4-chlorophenyl)-2-(3-pyridyl)ethanone hydrobromide
Used in the next reaction without purification.

Reference Example Compound 22-4: 2-bromo-1-(2-methylphenyl)-2-(3-pyridyl)ethanone hydrobromide
Used in the next reaction without purification.

Reference Example Compound 22-5: 2-bromo-1-(3-methylphenyl)-2-(3-pyridyl)ethanone hydrobromide
Used in the next reaction without purification.

Reference Example Compound 22-6: 2-bromo-1-(4-methylphenyl)-2-(3-pyridyl)ethanone hydrobromide
melting point: 96–98° C.

Reference Example Compound 22-7: 2-bromo-1-(3-methoxyphenyl)-2-(3-pyridyl)ethanone hydrobromide
Used in the next reaction without purification.

Reference Example Compound 22-9: 2-bromo-1-[4-(1,1-dimethylethyl)phenyl]-2-(3-pyridyl)ethanone hydrobromide
melting point: 190–194° C.

Reference Example Compound 22-9: 2-bromo-1-(3,5-dimethylphenyl)-2-(3-pyridyl)ethanone hydrobromide
melting point: 195–197° C.

Reference Example Compound 22-10: 2-bromo-1-(2-chlorophenyl)-2-(4-pyridyl)ethanone hydrobromide
melting point: 157–159° C.

Reference Example Compound 22-11: 2-bromo-1-(3-chlorophenyl)-2-(4-pyridyl)ethanone hydrobromide
melting point: 178–181° C.

Reference Example Compound 22-12: 2-bromo-1-(4-chlorophenyl)-2-(4-pyridyl)ethanone hydrobromide
melting point: 189–193° C.

Reference Example Compound 22-13: 2-bromo-1-(2-methylphenyl)-2-(4-pyridyl)ethanone hydrobromide
melting point: 183–186° C.

Reference Example Compound 22-14: 2-bromo-1-(3-methylphenyl)-2-(4-pyridyl)ethanone hydrobromide
Used in the next reaction without purification.

Reference Example Compound 22-15: 2-bromo-1-(4-methylphenyl)-2-(4-pyridyl)ethanone hydrobromide
melting point: 111–113° C.

Reference Example Compound 22-16: 2-bromo-1-(2-methoxyphenyl)-2-(4-pyridyl)ethanone hydrobromide
melting point: 168–171° C.

Reference Example Compound 22-17: 2-bromo-1-(3-methoxyphenyl)-2-(4-pyridyl)ethanone hydrobromide
Used in the next reaction without purification.

Reference Example Compound 22-18: 2-bromo-1-(4-ethylphenyl)-2-(4-pyridyl)ethanone hydrobromide
melting point: 170–173° C.

Reference Example Compound 22-19: 2-bromo-1-[4-(1-methylethyl)phenyl]-2-(4-pyridyl)ethanone hydrobromide
melting point: 185–188° C.

Reference Example Compound 22-20: 2-bromo-1-[4-(1,1-dimethylethyl)phenyl]-2-(4-pyridyl)ethanone hydrobromide
1-[4-(1,1-Dimethylethyl)phenyl]-2-(4-pyridyl)ethanone (10 g, 39 mmol) was dissolved in acetic acid (40 mL) and bromine (2.0 mL, 39 mmol) was added. The mixture was stirred at 80° C. for 3 h. The reaction mixture was cooled with iced water and the precipitated crude crystals were collected by filtration. The crude crystals were washed with ethyl acetate to give the title compound (9.6 g, yield 81%).
melting point: 209–212° C.

Reference Example Compound 22-21: 2-bromo-1-(4-propylphenyl)-2-(4-pyridyl)ethanone hydrobromide
melting point: 167–170° C.

Reference Example Compound 22-22: 2-bromo-1-(4-butylphenyl)-2-(4-pyridyl)ethanone hydrobromide
melting point: 158–161° C.

Reference Example Compound 22-23: 2-bromo-1-(4-hexylphenyl)-2-(4-pyridyl)ethanone hydrobromide
melting point; 153–155° C.

Reference Example Compound 22-24: 2-bromo-2-(4-pyridyl)-1-(4-trifluoromethoxyphenyl)ethanone hydrobromide Used in the next reaction without purification.

Reference Example Compound 22-25: 2-bromo-2-(4-pyridyl)-1-(4-trifluoromethylphenyl)ethanone hydrobromide
melting point: 190–194° C.

Reference Example Compound 22-26: 2-bromo-1-(4-dimethylaminophenyl)-2-(4-pyridyl)ethanone dihydrobromide
melting point: 163–167° C.

Reference Example Compound 22-27: 2-bromo-1-(3,4-dimethoxyphenyl)-2-(4-pyridyl)ethanone hydrobromide
melting point: 174–175° C.

Reference Example Compound 22-28: 2-bromo-1-(3,4-dimethylphenyl)-2-(4-pyridyl)ethanone hydrobromide
melting point: 196–199° C.

Reference Example Compound 22-29: 2-bromo-1-(3,5-dimethylphenyl)-2-(4-pyridyl)ethanone hydrobromide 1-(3,5-Dimethylphenyl)-2-(4-pyridyl)ethanone (7.0 g, 31 mmol) was dissolved in acetic acid (35 mL) and bromine (1.6 mL, 31 mmol) was added. The mixture was stirred at 80° C. for 3 h. Ethyl acetate was added to the residue and the precipitated crude crystals were collected by filtration. The crude crystals were washed with ethyl acetate to give the title compound (16 g, yield 96%).

melting point: 216–219° C.

Reference Example Compound 22-30: 2-bromo-1-(3,4-methylenedioxyphenyl)-2-(4-pyridyl)ethanone hydrobromide
melting point: 211–214° C.

Reference Example Compound 22-31: 2-bromo-1-(2-naphthyl)-2-(4-pyridyl)ethanone hydrobromide
melting point: 149–152° C.

Reference Example Compound 22-32: 2-bromo-1-(4-fluorophenyl)-2-(4-pyridyl)ethanone hydrobromide
melting point: 185–189° C.

Reference Example Compound 22-33: 2-bromo-1-(3-cyclopentyloxy-4-methoxyphenyl)-2-(4-pyridyl)ethanone hydrobromide
melting point: 168–170° C.

Reference Example 23

In accordance with the method described in Reference Examples 8–12, JP-A-61-10580 and U.S. Pat. No. 4,612,321, Reference Example compounds 23-1 to 23-294 and 23-295 to 23-349 shown in the following Tables 8 to 31 were synthesized.

TABLE 8

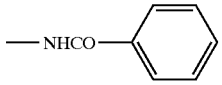

| Reference Example Compound | $R_a$ | $R_b$ | $R_c$ | additives | m.p./° C. |
|---|---|---|---|---|---|
| 23-1 | 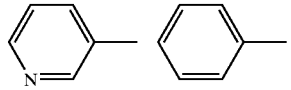 |  | 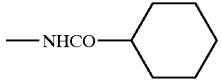 | HCl | 260 |
| 23-2 | 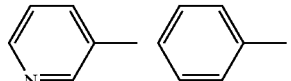 |  | 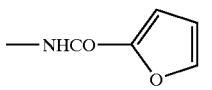 | HCl | 244–246 |
| 23-3 | 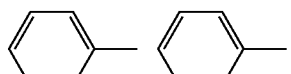 |  | 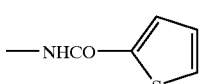 | HCl | 255–256 |
| 23-4 | 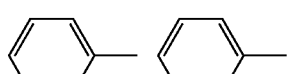 |  | 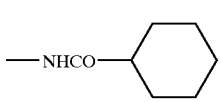 | HCl | 275 |
| 23-5 | 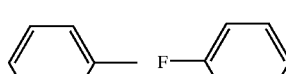 |  | 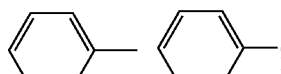 | | 233 |
| 23-6 | —NHCOMe |  |  | | 218–220 |
| 23-7 | —NHCOMe | 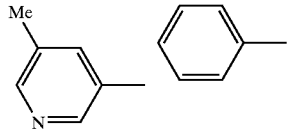 |  | | 218–220 |

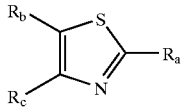

TABLE 9

| Reference Example Compound | Rₐ | R_b | R_c | additives | m.p./° C. |
|---|---|---|---|---|---|
| 23-18 | —NHCO-(2-thienyl) | 3-pyridyl | 4-MeO-phenyl | HCl | 237–239 |
| 23-19 | —NHCO-cyclohexyl | 3-pyridyl | 4-MeO-phenyl | HCl | 220–223 |
| 23-20 | —NHCOCH₂-phenyl | 3-pyridyl | 4-MeO-phenyl |  | 184–185 |
| 23-21 | —NHCO(CH₂)₂-phenyl | 3-pyridyl | 4-MeO-phenyl |  | 214–216 |
| 23-22 | —NHCO(CH₂)₂Me | 3-pyridyl | 4-MeO-phenyl |  | 197–198 |
| 23-23 | —NHCO(CH₂)₃Me | 3-pyridyl | 4-MeO-phenyl |  | 188–190 |
| 23-24 | —NHCO(CH₂)₄Me | 3-pyridyl | 4-MeO-phenyl |  | 167–169 |
| 23-25 | —NHCOCMe₃ | 3-pyridyl | 4-MeO-phenyl |  | 245–246 |
| 23-26 | —NHCO-phenyl | 4-pyrimidinyl | phenyl |  | 237–238 |
| 23-27 | —NHCO-(2-furyl) | 4-pyridyl | phenyl |  | 240 |
| 23-28 | —NHCO-(2-thienyl) | 4-pyridyl | phenyl |  | 240 |
| 23-29 | —NHCOCH₂-phenyl | 4-pyridyl | phenyl |  | 233–234 |
| 23-30 | —NHCO(CH₂)₂-phenyl | 4-pyridyl | phenyl |  | 214–216 |

TABLE 9-continued

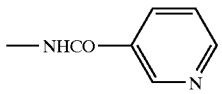

| Reference Example Compound | $R_a$ | $R_b$ | $R_c$ | additives | m.p./° C. |
|---|---|---|---|---|---|
| 23-31 | —NHCOCMe₃ | 4-pyridyl | phenyl | | 206–208 |
| 23-32 | —NHCO-(3-pyridyl) | 4-pyridyl | phenyl | | 247 |
| 23-33 | —NHCO(CH₂)₂Me | 4-pyridyl | phenyl | | 212–214 |
| 23-34 | —NHCO(CH₂)₃Me | 4-pyridyl | phenyl | | 232–234 |
| 23-35 | —NHCO(CH₂)₄Me | 4-pyridyl | phenyl | | 245–246 |

TABLE 10

| Reference Example Compound | $R_a$ | $R_b$ | $R_c$ | m.p./° C. |
|---|---|---|---|---|
| 23-36 | —NHCO-cyclohexyl | 4-pyridyl | phenyl | 219–220 |
| 23-37 | —NHCOCH₂Me | 4-pyridyl | 4-MeO-phenyl | 254–256 |
| 23-38 | —NHCO-phenyl | 4-pyridyl | 4-MeO-phenyl | 255–257 |
| 23-39 | —NH₂ | 3-pyridyl | 4-Cl-phenyl | 278–280 |
| 23-40 | —NHCOMe | 3-pyridyl | 4-Cl-phenyl | 266–268 |

TABLE 10-continued
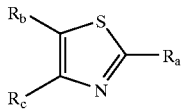
| Reference Example Compound | R$_a$ | R$_b$ | R$_c$ | m.p./° C. |
|---|---|---|---|---|
| 23-41 | —NHCOCH$_2$Me | 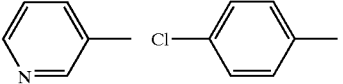 |  | 241–242 |
| 23-42 | —NH$_2$ | 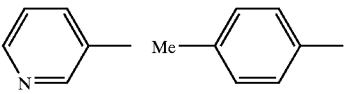 |  | 286–288 |
| 23-43 | —NHCOMe | 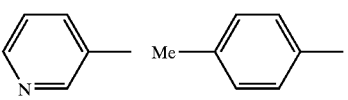 |  | 260–261 |
| 23-44 | —NHCOCH$_2$Me | 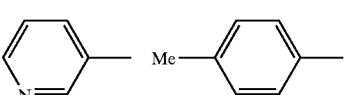 |  | 226–227 |
| 23-45 | —NHCOMe | 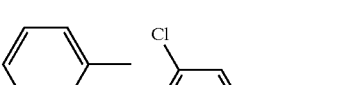 |  | 217–219 |
| 23-46 | —NHCOCH$_2$Me | 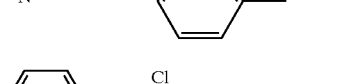 |  | 228–229 |
| 23-47 | —NHCOMe | 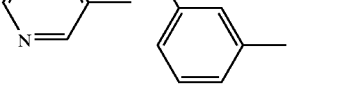 |  | 235–236 |
| 23-48 | —NHCOCH$_2$Me | 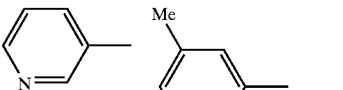 |  | 239–241 |
| 23-49 | —NHCOMe | 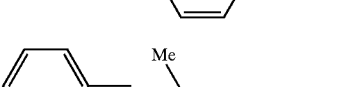 |  | 290–293 |
| 23-50 | —NHCOCH$_2$Me | 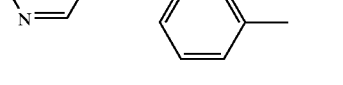 |  | 289–290 |
| 23-51 | —NHCOMe | 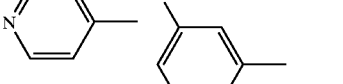 |  | 287–289 |

TABLE 11

| Reference Example Compound | Rₐ | R_b | R_c | m.p./° C. |
|---|---|---|---|---|
| 23-52 | —NHCOCH₂Me | 4-pyridyl | 3-methylphenyl | 258–260 |
| 23-53 | —NHCOMe | 4-pyridyl | 4-chlorophenyl | 317–320 |
| 23-54 | —NHCOCH₂Me | 4-pyridyl | 4-chlorophenyl | 257–259 |
| 23-55 | —NHCOMe | 4-pyridyl | 4-methylphenyl | 308–309 |
| 23-56 | —NHCOCH₂Me | 4-pyridyl | 4-methylphenyl | 249–250 |
| 23-57 | —NH₂ | 3-pyridyl | 3-chlorophenyl | 228–230 |
| 23-58 | —NH₂ | 3-pyridyl | 3-methylphenyl | 231–232 |
| 23-59 | —NH₂ | pyrimidinyl | 3-chlorophenyl | 256–258 |
| 23-60 | —NH₂ | 4-pyridyl | 3-methylphenyl | 255–258 |
| 23-61 | —NH₂ | 4-pyridyl | 4-chlorophenyl | >300 |
| 23-62 | —NH₂ | 4-pyridyl | 4-methylphenyl | 296–298 |

TABLE 11-continued
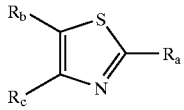
| Reference Example Compound | Rₐ | Rᵦ | R_c | m.p./° C. |
|---|---|---|---|---|
| 23-63 | —N=C(Me)NMe₂ | 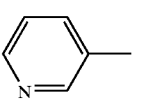 | 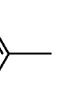 | 129–131 |
| 23-64 | —NHCOMe | 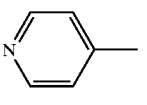 | 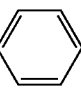 | 282–284 |
| 23-65 | —NHCOMe | 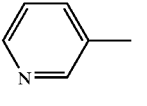 | 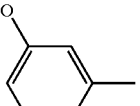 | 236–239 |
| 23-66 | —NHCOCH₂Me | 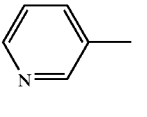 | 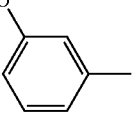 | 222–224 |
| 23-67 | 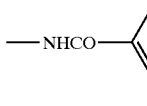 | 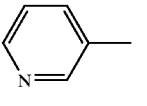 | 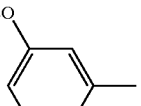 | 236–239 |
TABLE 12
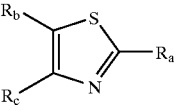
| Reference Example Compound | Rₐ | Rᵦ | R_c | m.p./° C. |
|---|---|---|---|---|
| 23-68 | —NHCOMe | 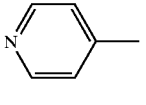 | 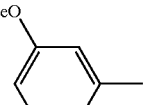 | 234–236 |
| 23-69 | —NHCOCH₂Me | 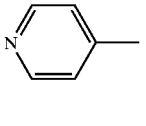 | 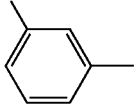 | 237–239 |
| 23-70 | 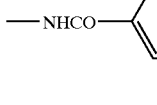 | 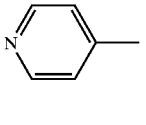 | 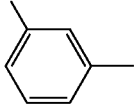 | 220–222 |

TABLE 12-continued
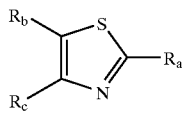
| Reference Example Compound | $R_a$ | $R_b$ | $R_c$ | m.p./° C. |
|---|---|---|---|---|
| 23-71 | —NHCOMe | 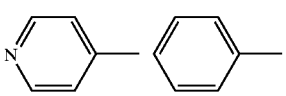 | 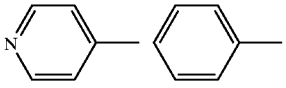 | 294–297 |
| 23-72 | —NHCOCH$_2$Me | 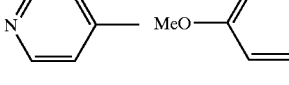 | 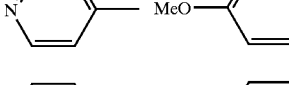 | 267–269 |
| 23-73 | —N(CH$_2$Me)COMe | 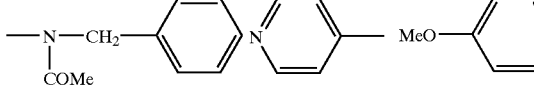 | 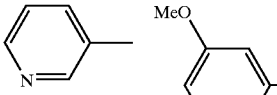 | 143–144 |
| 23-74 | —N((CH$_2$)$_4$Me)COMe | 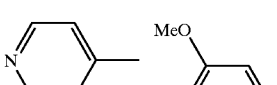 | 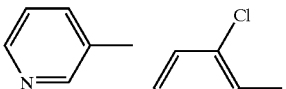 | 111–113 |
| 23-75 | 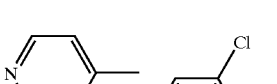 | 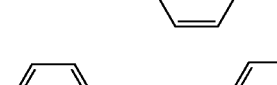 |  | 162–164 |
| 23-76 | —NH$_2$ | | | 206–209 |
| 23-77 | —NH$_2$ | | | 232–234 |
| 23-78 | —NH$_2$ | | | 236–239 |
| 23-79 | —NH$_2$ | | | 232–235 |
| 23-80 | | | | 287–289 |
| 23-81 | | | | 330–333 |

TABLE 12-continued
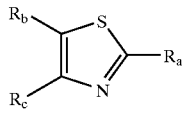
| Reference Example Compound | $R_a$ | $R_b$ | $R_c$ | m.p./° C. |
|---|---|---|---|---|
| 23-82 | 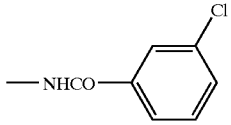 | 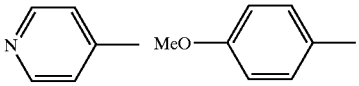 |  | 292–294 |
TABLE 13
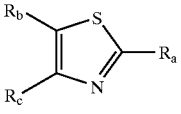
| Reference Example Compound | $R_a$ | $R_b$ | $R_c$ | m.p./° C. |
|---|---|---|---|---|
| 23-83 | 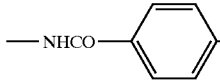 | 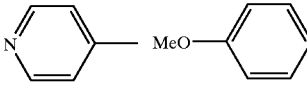 |  | 346–348 |
| 23-84 | 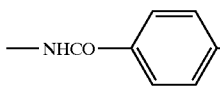 | 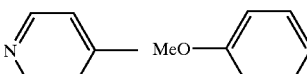 |  | 308–310 |
| 23-85 | —NH$_2$ |  | 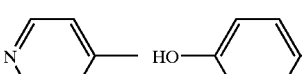 | 323–326 |
| 23-86 | —NHCOMe |  |  | 259–261 |
| 23-87 | —NHCOMe | 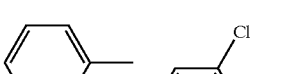 |  | 292–293 |
| 23-88 |  | 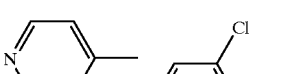 |  | 161–163 |
| 23-89 | —NH$_2$ | 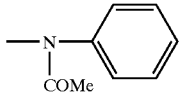 | 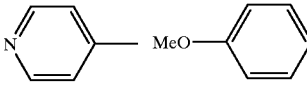 | 235–237 |

TABLE 13-continued
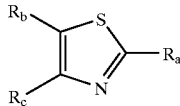
| Reference Example Compound | $R_a$ | $R_b$ | $R_c$ | m.p./° C. |
|---|---|---|---|---|
| 23-90 | —NHCOMe | 4-pyridyl | 4-(MeCOO)C₆H₄— | 254–257 |
| 23-91 | —NHCOCH₂Ph | 4-pyridyl | 4-(MeO)C₆H₄— | 274–277 |
| 23-92 | —NHCOMe | 3-pyridyl | 2-MeC₆H₄— | 237–239 |
| 23-93 | —NHCOMe | 4-pyridyl | 4-(HO)C₆H₄— | 285–287 |
| 23-94 | —NH₂ | 4-pyridyl | 2-MeC₆H₄— | 235–238 |
| 23-95 | —NHCOMe | 4-pyridyl | 2-MeC₆H₄— | 272–274 |
| 23-96 | —NH₂ | 4-pyridyl | 2-(MeO)C₆H₄— | 213–215 |
| 23-97 | —NHCOMe | 4-pyridyl | 2-(MeO)C₆H₄— | 259–261 |
| 23-98 | —NHCO(CH₂)₄Cl | 4-pyridyl | 4-(MeO)C₆H₄— | 228–229 |

TABLE 14

[Structure: thiazole with Rb at 5-position, Ra at 2-position, Rc at 4-position]

| Reference Example Compound | Rₐ | Rᵦ | R_c | m.p./° C. |
|---|---|---|---|---|
| 23-99 | —NHCOMe | 4-pyridyl | —C₆H₄—CH₂—O—C₆H₄— | 254–257 |
| 23-100 | N-(2-oxopiperidinyl) | 4-pyridyl | MeO—C₆H₄— | 159–160 |
| 23-101 | —NHCO-(3-pyridyl) | 4-pyridyl | MeO—C₆H₄— | 278–281 |
| 23-102 | —NHCO-(4-pyridyl) | 4-pyridyl | MeO—C₆H₄— | 295–297 |
| 23-103 | —NHCO-(2-thienyl) | 4-pyridyl | MeO—C₆H₄— | 262–264 |
| 23-104 | —NHCO-(2-furyl) | 4-pyridyl | MeO—C₆H₄— | 266–269 |
| 23-105 | —NHCOCHMe₂ | 4-pyridyl | MeO—C₆H₄— | 227–230 |
| 23-106 | —NHCOCMe₃ | 4-pyridyl | MeO—C₆H₄— | 254–256 |
| 23-107 | —NHCOCH₂CHMe₂ | 4-pyridyl | MeO—C₆H₄— | 261–262 |
| 23-108 | —NHCONH(CH₂)₂Me | 4-pyridyl | MeO—C₆H₄— | 215–219 |
| 23-109 | —NH₂ | 4-pyridyl | MeCH₂—C₆H₄— | 285–288 |
| 23-110 | —NHCOMe | 4-pyridyl | MeCH₂—C₆H₄— | 294–295 |
| 23-111 | —NHCOMe | 4-pyridyl | MeCH₂O—C₆H₄— | 206–209 |

TABLE 14-continued

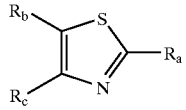

| Reference Example Compound | $R_a$ | $R_b$ | $R_c$ | m.p./° C. |
|---|---|---|---|---|
| 23-112 | —NHCOMe | 4-pyridyl | 4-Me(CH$_2$)$_3$O-phenyl | 201–203 |
| 23-113 | —NHCOMe | 4-pyridyl | 4-Me(CH$_2$)$_5$O-phenyl | 210–212 |
| 23-114 | —NHCO(CH$_2$)$_3$Cl | 4-pyridyl | 4-MeO-phenyl | 191–194 |

TABLE 15

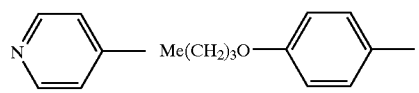

| Reference Example Compound | $R_a$ | $R_b$ | $R_c$ | m.p./° C. |
|---|---|---|---|---|
| 23-115 | N-methyl-2-pyrrolidinonyl | 4-pyridyl | 4-MeO-phenyl | 133–135 |
| 23-116 | —NHCO(CH$_2$)$_5$Cl | 4-pyridyl | 4-MeO-phenyl | 223–225 |
| 23-117 | —NHCO-(2,6-diMe-phenyl) | 4-pyridyl | 4-MeO-phenyl | 351–352 |
| 23-118 | —NHCOMe | 4-pyridyl | 2,3-diMeO-phenyl | 265–267 |
| 23-119 | —NHCOMe | 4-pyridyl | 2,3-diMe-phenyl | 248–250 |

TABLE 15-continued
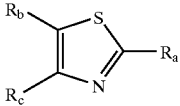
| Reference Example Compound | Rₐ | Rᵦ | R_c | m.p./° C. |
|---|---|---|---|---|
| 23-120 | —NHCOMe | 4-pyridyl | 4-(Me₂CH)C₆H₄— | 295–297 |
| 23-121 | —NHCO(CH₂)₂COOCH₂Me | 4-pyridyl | 4-MeOC₆H₄— | 261–264 |
| 23-122 | —NHCO(CH₂)₂COOH | 4-pyridyl | 4-MeOC₆H₄— | 334–336 |
| 23-123 | —NH₂ | 4-pyridyl | 4-(Me₂CH)C₆H₄— | 267–269 |
| 23-124 | —NH₂ | 4-pyridyl | 2,3-(MeO)₂C₆H₃— | 218–219 |
| 23-125 | —NH₂ | 4-pyridyl | 2,3-Me₂C₆H₃— | 248–250 |
| 23-126 | —NH₂ | 4-pyridyl | 3,4-methylenedioxyphenyl | 273–275 |
| 23-127 | —NHCOMe | 4-pyridyl | 3,4-methylenedioxyphenyl | 295–296 |
| 23-128 | —NHCOMe | 4-pyridyl | 3,5-Me₂C₆H₃— | 284–286 |
| 23-129 | —NHCOMe | 4-pyridyl | 4-(Me₂N)C₆H₄— | 289–291 |

TABLE 16

| Reference Example Compound | R_a | R_b | R_c | additives | m.p./° C. |
|---|---|---|---|---|---|
| 23-130 | —NHCOCHMe$_2$ | 4-pyridyl | 4-(Me$_2$CH)-C$_6$H$_4$— | | 284–285 |
| 23-131 | —NHCOCMe$_3$ | 4-pyridyl | 4-(Me$_2$CH)-C$_6$H$_4$— | | 293–295 |
| 23-132 | —NHCONH(CH$_2$)$_2$Me | 4-pyridyl | 4-(Me$_2$CH)-C$_6$H$_4$— | | 287–288 |
| 23-133 | —NH$_2$ | 4-pyridyl | 3,5-Me$_2$-C$_6$H$_3$— | | 242–244 |
| 23-134 | —NH$_2$ | 4-pyridyl | 4-(Me$_2$N)-C$_6$H$_4$— | | 309–311 |
| 23-135 | —CH$_2$COOCH$_2$Me | 4-pyridyl | 4-MeO-C$_6$H$_4$— | HCl | 150–152 |
| 23-136 | —CH$_2$NHCO-C$_6$H$_5$ | 4-pyridyl | 4-MeO-C$_6$H$_4$— | | 150–151 |
| 23-137 | —NHCOMe | 4-pyridyl | 4-(Me$_3$C)-C$_6$H$_4$— | | 280–281 |
| 23-138 | —NHCOCHMe$_2$ | 4-pyridyl | 4-(Me$_3$C)-C$_6$H$_4$— | | 303–304 |
| 23-139 | —NHCOCMe$_3$ | 4-pyridyl | 4-(Me$_3$C)-C$_6$H$_4$— | | 317–319 |
| 23-140 | —NHCOMe | 4-pyridyl | 6-naphthyl | | 342–345 |
| 23-141 | —NHCOCHMe$_2$ | 4-pyridyl | 6-naphthyl | | 297–298 |

TABLE 16-continued

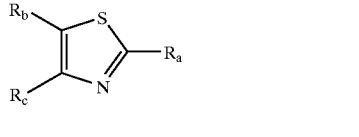

| Reference Example Compound | $R_a$ | $R_b$ | $R_c$ | additives | m.p./° C. |
|---|---|---|---|---|---|
| 23-142 | —NHCOCMe₃ | 4-pyridyl | 6-(2-naphthyl) | | 313–315 |
| 23-143 | —NH₂ | 4-pyridyl | 4-(tert-butyl)phenyl | | 254–257 |
| 23-144 | —NH₂ | 4-pyridyl | 6-(2-naphthyl) | | 261–264 |
| 23-145 | —CH₂COOH | 4-pyridyl | 4-MeO-phenyl | | 135–137 |
| 23-146 | —CH₂CONHMe | 4-pyridyl | 4-MeO-phenyl | | 129–130 |

TABLE 17

| Reference Example Compound | $R_a$ | $R_b$ | $R_c$ | m.p./° C. |
|---|---|---|---|---|
| 23-147 | —Me | 4-pyridyl | 4-MeO-phenyl | 132–133 |
| 23-148 | —NHCOMe | 4-pyridyl | 4-Me(CH₂)₂-phenyl | 256–258 |
| 23-149 | —NHCOCHMe₂ | 4-pyridyl | 4-Me(CH₂)₂-phenyl | 269–272 |
| 23-150 | —NHCO-phenyl | 4-pyridyl | 4-Me(CH₂)₂-phenyl | 240–242 |
| 23-151 | —NHCOMe | 4-pyridyl | 4-Me(CH₂)₃-phenyl | 259–261 |

TABLE 17-continued

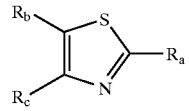

| Reference Example Compound | $R_a$ | $R_b$ | $R_c$ | m.p./° C. |
|---|---|---|---|---|
| 23-152 | —NHCOMe | 4-pyridyl | Me(CH$_2$)$_5$—C$_6$H$_4$— | 237–239 |
| 23-153 | —NHCOMe | 4-pyridyl | CF$_3$O—C$_6$H$_4$— | 296–298 |
| 23-154 | —NHCOCHMe$_2$ | 4-pyridyl | CF$_3$O—C$_6$H$_4$— | 285–286 |
| 23-155 | —NHCOCF$_3$ | 4-pyridyl | MeO—C$_6$H$_4$— | 260–262 |
| 23-156 | —NHCONHCH$_2$Me | 4-pyridyl | MeO—C$_6$H$_4$— | 224–226 |
| 23-157 | —NHCONHCH$_2$Me | 4-pyridyl | Me$_2$CH—C$_6$H$_4$— | 181–183 |
| 23-158 | —NH$_2$ | 4-pyridyl | Me(CH$_2$)$_2$—C$_6$H$_4$— | 240–242 |
| 23-159 | —NH$_2$ | 4-pyridyl | Me(CH$_2$)$_3$—C$_6$H$_4$— | 204–206 |
| 23-160 | —NH$_2$ | 4-pyridyl | Me(CH$_2$)$_5$—C$_6$H$_4$— | 178–179 |
| 23-161 | —NH$_2$ | 4-pyridyl | CF$_3$O—C$_6$H$_4$— | 262–264 |
| 23-162 | —COOH | 4-pyridyl | MeO—C$_6$H$_4$— | 141–143 |
| 23-163 | —NHCOCH$_2$Me | 4-pyridyl | Me$_3$C—C$_6$H$_4$— | 295–297 |
| 23-164 | —NHCO—C$_6$H$_5$ | 4-pyridyl | Me$_3$C—C$_6$H$_4$— | 292–294 |
| 23-165 | —NHCO-(3-pyridyl) | 4-pyridyl | Me$_3$C—C$_6$H$_4$— | 326–328 |

TABLE 18

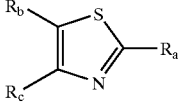

| Reference Example Compound | $R_a$ | $R_b$ | $R_c$ | m.p./° C. |
|---|---|---|---|---|
| 23-166 | —NHCO-(4-pyridyl) | 4-pyridyl | Me₃C-C₆H₄- | 326–329 |
| 23-167 | —NHCOCH₂-phenyl | 4-pyridyl | Me₃C-C₆H₄- | 277–279 |
| 23-168 | —NHCO-cyclopentyl | 4-pyridyl | Me₃C-C₆H₄- | 309–311 |
| 23-169 | —NHCONHCH₂Me | 4-pyridyl | Me₃C-C₆H₄- | 289–292 |
| 23-170 | —NHCONH(CH₂)₂Me | 4-pyridyl | Me₃C-C₆H₄- | 212–214 |
| 23-171 | —NHCOCH₂OMe | 4-pyridyl | Me₃C-C₆H₄- | 248–249 |
| 23-172 | —NHCOMe | 3-pyridyl | Me₃C-C₆H₄- | 228–230 |
| 23-173 | —NHCOCH₂Me | 3-pyridyl | Me₃C-C₆H₄- | 244–246 |
| 23-174 | —NHCOCHMe₂ | 3-pyridyl | Me₃C-C₆H₄- | 228–229 |
| 23-175 | —NHCOCH₂-phenyl | 3-pyridyl | Me₃C-C₆H₄- | 204–206 |
| 23-176 | —NHCO-(3-pyridyl) | 3-pyridyl | Me₃C-C₆H₄- | 216–218 |
| 23-177 | —NHCO-cyclopentyl | 3-pyridyl | Me₃C-C₆H₄- | 218–220 |
| 23-178 | —NHCO-(3-pyridyl) | 3-pyridyl | Me₃C-C₆H₄- | 251–253 |

TABLE 18-continued
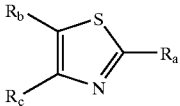
| Reference Example Compound | $R_a$ | $R_b$ | $R_c$ | m.p./° C. |
|---|---|---|---|---|
| 23-179 | —NHCO—  |  | Me$_3$C—  | 271–273 |
| 23-180 | —NHCONHCH$_2$Me |  | Me$_3$C—  | 302–305 |
| 23-181 | —NHCONH(CH$_2$)$_2$Me |  | Me$_3$C—  | 190–192 |
| 23-182 | —NH$_2$ |  | Me$_3$C—  | 239–241 |
| 23-183 | —NH$_2$ |  | CF$_3$—  | 304–306 |
TABLE 19
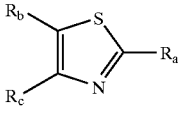
| Reference Example Compound | $R_a$ | $R_b$ | $R_c$ | m.p./° C. |
|---|---|---|---|---|
| 23-184 | —NHCOMe |  | CF$_3$—  | 328–330 |
| 23-185 | —NHCOCH$_2$Me |  | CF$_3$—  | 284–286 |
| 23-186 | —NHCOCHMe$_2$ |  | CF$_3$—  | 274–275 |
| 23-187 | —NHCOCH$_2$—  |  | CF$_3$—  | 295–296 |
| 23-188 | —NHCO—  |  | CF$_3$—  | 254–255 |

TABLE 19-continued

![structure: Rb-S, Ra on thiazole, Rc-N]

| Reference Example Compound | Ra | Rb | Rc | m.p./° C. |
|---|---|---|---|---|
| 23-189 | —NHCO-cyclopentyl | 4-pyridyl | 4-CF₃-phenyl | 272–273 |
| 23-190 | —NHCO-(3-pyridyl) | 4-pyridyl | 4-CF₃-phenyl | 262–264 |
| 23-191 | —NHCO-(4-pyridyl) | 4-pyridyl | 4-CF₃-phenyl | 263–264 |
| 23-192 | —NHCONHCH₂Me | 4-pyridyl | 4-CF₃-phenyl | 206–207 |
| 23-193 | —NHCONH(CH₂)₂Me | 4-pyridyl | 4-CF₃-phenyl | 208–210 |
| 23-194 | —NHCOCH₂Me | 4-pyridyl | 3,5-diMe-phenyl | 291–293 |
| 23-195 | —NHCOCHMe₂ | 4-pyridyl | 3,5-diMe-phenyl | 270–272 |
| 23-196 | —NHCOCH₂-phenyl | 4-pyridyl | 3,5-diMe-phenyl | 226–229 |
| 23-197 | —NHCO-phenyl | 4-pyridyl | 3,5-diMe-phenyl | 285–286 |
| 23-198 | —NHCO-cyclopentyl | 4-pyridyl | 3,5-diMe-phenyl | 275–278 |

TABLE 20

| Reference Example Compound | Ra | Rb | Rc | m.p./° C. |
|---|---|---|---|---|
| 23-199 | —NHCO-(3-pyridyl) | 4-pyridyl | 3,5-dimethylphenyl | 267–270 |
| 23-200 | —NHCO-(4-pyridyl) | 4-pyridyl | 3,5-dimethylphenyl | 302–304 |
| 23-201 | —NHCONHCH₂Me | 4-pyridyl | 3,5-dimethylphenyl | 202–203 |
| 23-202 | —NHCONH(CH₂)₂Me | 4-pyridyl | 3,5-dimethylphenyl | 128–130 |
| 23-203 | —NHCOCH₂OMe | 4-pyridyl | 3,5-dimethylphenyl | 220–222 |
| 23-204 | —NH₂ | 3-pyridyl | 3,5-dimethylphenyl | 237–240 |
| 23-205 | —NHCOMe | 3-pyridyl | 3,5-dimethylphenyl | 288–289 |

TABLE 20-continued
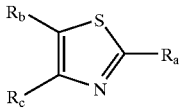
| Reference Example Compound | R$_a$ | R$_b$ | R$_c$ | m.p./° C. |
|---|---|---|---|---|
| 23-206 | —NHCOCH$_2$Me | 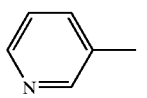 | 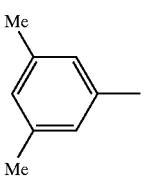 | 292–293 |
| 23-207 | —NHCOCHMe$_2$ | 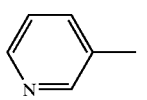 | 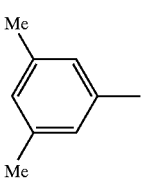 | 253–254 |
| 23-208 | —NHCOCH$_2$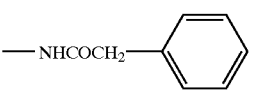 | 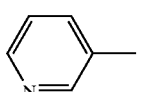 | 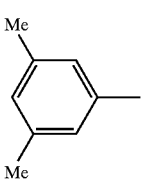 | 235–238 |
TABLE 21
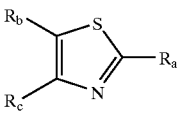
| Reference Example Compound | R$_a$ | R$_b$ | R$_c$ | additives | m.p./° C. |
|---|---|---|---|---|---|
| 23-209 | —NHCO | 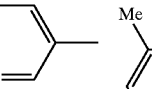 | 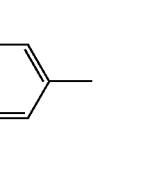 | | 300–301 |
| 23-210 | —NHCO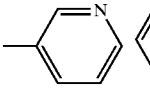 | 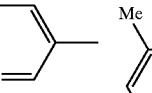 | 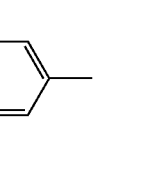 | | 277–278 |

TABLE 21-continued

[Thiazole structure with $R_b$ at position 5, $R_a$ at position 2, $R_c$ at position 4]

| Reference Example Compound | $R_a$ | $R_b$ | $R_c$ | additives | m.p./° C. |
|---|---|---|---|---|---|
| 23-211 | —NHCO—[pyridine] | [pyridazine] | 3,5-dimethylphenyl | | 278–280 |
| 23-212 | —NHCONHCH$_2$Me | [3-pyridyl] | 3,5-dimethylphenyl | | 220–224 |
| 23-213 | —NHCONH(CH$_2$)$_2$Me | [3-pyridyl] | 3,5-dimethylphenyl | | 204–206 |
| 23-214 | —COOCH$_2$Me | [4-pyridyl] | 4-MeO-phenyl | | 149–150 |
| 23-215 | —NHCOCH$_2$NMe$_2$ | [4-pyridyl] | 4-Me$_3$C-phenyl | | 230–231 |
| 23-216 | —NH$_2$ | [3-pyridyl] | 4-(MeCH$_2$OCOCH$_2$O)-phenyl | | 167–169 |
| 23-217 | —NHCOMe | [3-pyridyl] | 4-(MeCH$_2$OCOCH$_2$O)-phenyl | | 195–197 |
| 23-218 | —NHCOMe | [3-pyridyl] | 4-(HOCOCH$_2$O)-phenyl | | 266–270 |
| 23-219 | —NH$_2$ | [4-pyridyl] | 4-(MeCH$_2$OCOCH$_2$O)-phenyl | | 181–185 |
| 23-220 | —NHCOMe | [4-pyridyl] | 4-(MeCH$_2$OCOCH$_2$O)-phenyl | | 239–244 |
| 23-221 | —NHCOMe | [4-pyridyl] | 4-(HOCOCH$_2$O)-phenyl | HCl | 237–242 |

TABLE 21-continued
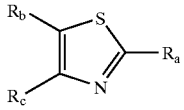
| Reference Example Compound | R_a | R_b | R_c | additives | m.p./° C. |
|---|---|---|---|---|---|
| 23-222 | 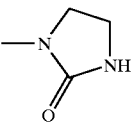 | 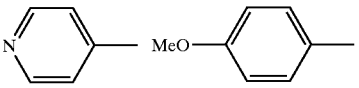 | | | 248–250 |
TABLE 22
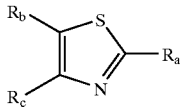
| Reference Example Compound | R_a | R_b | R_c | additives | m.p./° C. |
|---|---|---|---|---|---|
| 23-223 | —NHCOCH$_2$OH | 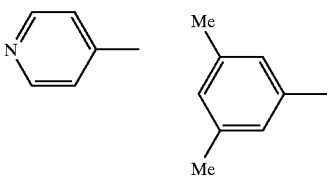 | 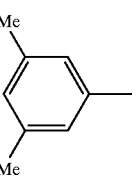 | | 243–245 |
| 23-224 | —NHCOMe | 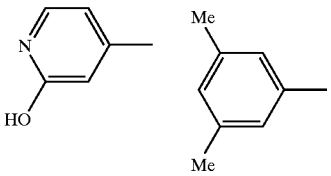 | 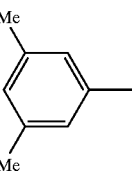 | | 371–373 |
| 23-225 | —NHCOMe | 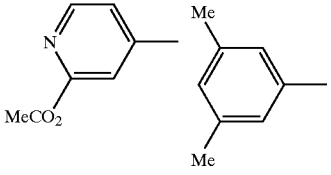 | 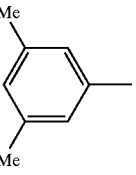 | | 350–351 |
| 23-226 | 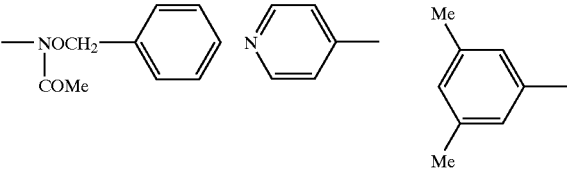 | 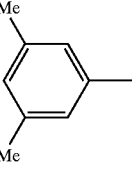 | | | 156–157 |
| 23-227 | 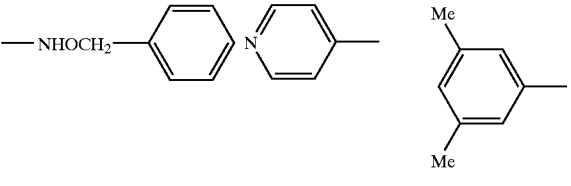 | 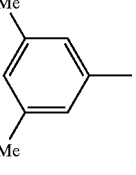 | Me (3,5-dimethylphenyl) | | 171–172 |

TABLE 22-continued

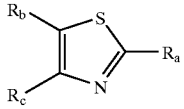

| Reference Example Compound | $R_a$ | $R_b$ | $R_c$ | additives | m.p./° C. |
|---|---|---|---|---|---|
| 23-228 | —NHCO-(3-pyridyl) | 4-pyridyl | Me-(4-phenyl) | | 276–278 |
| 23-229 | —NHCO-(3-pyridyl) | 4-pyridyl | MeCH$_2$-(4-phenyl) | | 276–277 |
| 23-230 | —NHCO-(3-pyridyl) | 4-pyridyl | Me(CH$_2$)$_2$-(4-phenyl) | | 250–251 |
| 23-231 | —NHCO-(3-pyridyl) | 4-pyridyl | Me(CH$_2$)$_3$-(4-phenyl) | | 241–242 |
| 23-232 | —NMeCOMe | 4-pyridyl | MeO-(4-phenyl) | HCl | 219–222 |
| 23-233 | —NHMe | 4-pyridyl | 3,5-diMe-phenyl | | 226–227 |

TABLE 23

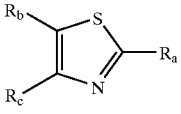

| Reference Example Compound | $R_a$ | $R_b$ | $R_c$ | additives | m.p./° C. |
|---|---|---|---|---|---|
| 23-234 | —NMeCOMe | 4-pyridyl | 3,5-diMe-phenyl | | 171–174 |
| 23-235 | —NMeCOMe | 4-pyridyl | 3,5-diMe-phenyl | HCl | 189–193 |

TABLE 23-continued
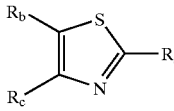
| Reference Example Compound | $R_a$ | $R_b$ | $R_c$ | additives | m.p./° C. |
|---|---|---|---|---|---|
| 23-236 | 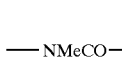 | 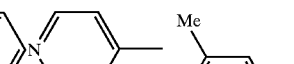 | 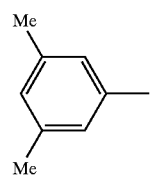 | | 210–214 |
| 23-237 |  | 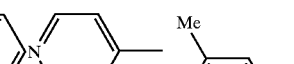 | 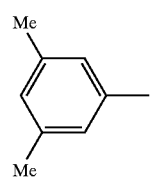 | HCl | 210–214 |
| 23-238 | 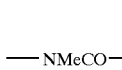 | 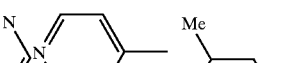 | 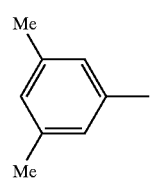 | | 212–214 |
| 23-239 | 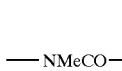 | 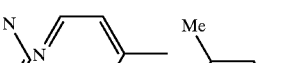 | 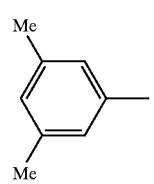 | 2HCl | 206–210 |
| 23-240 |  | 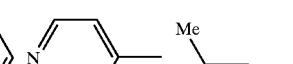 | 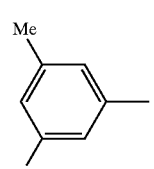 | HCl | 285–287 |
| 23-241 |  | 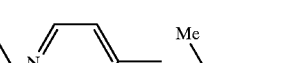 | 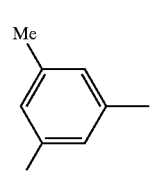 | 2HCl | 264–269 |
| 23-242 | —NHCH$_2$Me |  |  | | 179–182 |
| 23-243 | 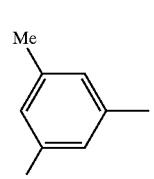 |  |  | 2HCl | 327–329 |

TABLE 23-continued

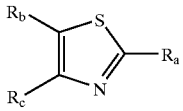

| Reference Example Compound | R$_a$ | R$_b$ | R$_c$ | additives | m.p./° C. |
|---|---|---|---|---|---|
| 23-244 | —NHCO-[3-pyridyl] | [4-pyridyl]- | [1-(4-methylphenyl)ethyl, CH(Me)(Me)] | | 293–295 |

TABLE 24

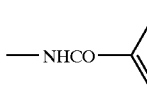

| Reference Example Compound | R$_a$ | R$_b$ | R$_c$ | additives | m.p./° C. |
|---|---|---|---|---|---|
| 23-245 | —NHCO-[2-pyrazinyl] | [4-pyridyl]- | Me$_3$C-[phenyl]- | | 245–247 |
| 23-246 | —NHCO-[2-pyrazinyl] | [4-pyridyl]- | [3,5-dimethylphenyl] | | 269–270 |
| 23-247 | —NHCO-[2-pyridyl] | [4-pyridyl]- | Me$_3$C-[phenyl]- | | 171–173 |
| 23-248 | —NMeCO-[4-pyridyl] | [4-pyridyl]- | MeO-[phenyl]- | | 141–142 |
| 23-249 | —NMeCO-[4-pyridyl] | [4-pyridyl]- | MeO-[phenyl]- | HCl | 194–196 |
| 23-250 | —NMeCO-[pyridazinyl] | [4-pyridyl]- | MeO-[phenyl]- | | 144–145 |
| 23-251 | —NMeCO-[pyridazinyl] | [4-pyridyl]- | MeO-[phenyl]- | 2HCl | 175–178 |
| 23-252 | —N(COMe)(CH$_2$Me) | [4-pyridyl]- | MeO-[phenyl]- | HCl | 184–187 |

TABLE 24-continued
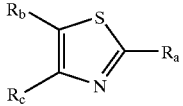
| Reference Example Compound | R$_a$ | R$_b$ | R$_c$ | additives | m.p./° C. |
|---|---|---|---|---|---|
| 23-253 | 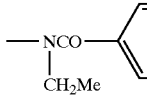 | 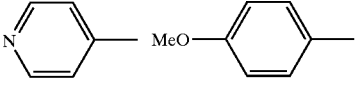 |  | | 128–130 |
| 23-254 | 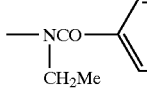 | 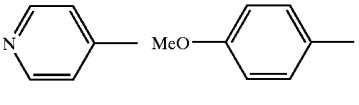 |  | HCl | 149–151 |
| 23-255 |  |  |  | | 144–145 |
| 23-256 | 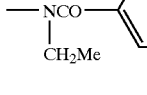 | 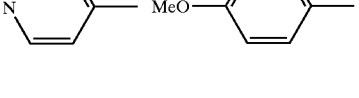 |  | 2HCl | 151–154 |
| 23-257 | —NMeCOMe |  | 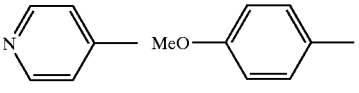 | | 186–188 |
TABLE 25
| Reference Example Compound | R$_a$ | R$_b$ | R$_c$ | additives | m.p./° C. |
|---|---|---|---|---|---|
| 23-258 | —NMeCOMe | 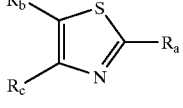 |  | HCl | 189–191 |
| 23-259 | —NMeCO—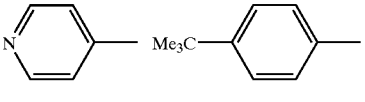 |  | 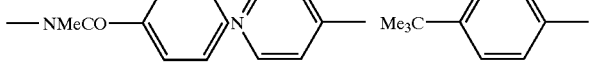 | | 204–206 |
| 23-260 | —NMeCO— | 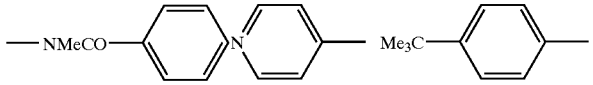 |  | HCl | 202–203 |
| 23-261 | —NMeCO—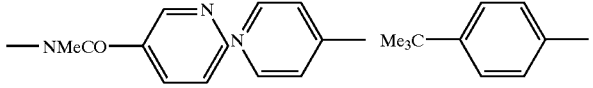 | |  | | 136–138 |

TABLE 25-continued
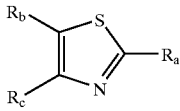
| Reference Example Compound | Ra | Rb | Rc | additives | m.p./° C. |
|---|---|---|---|---|---|
| 23-262 | —NMeCO— 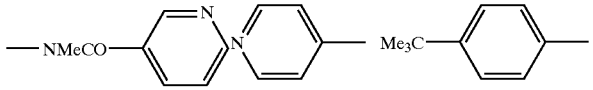 | 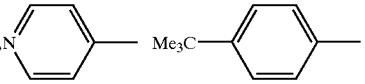 | Me₃C—  | 2HCl | 169–171 |
| 23-263 | —NCOMe<br>\|<br>CH₂Me | 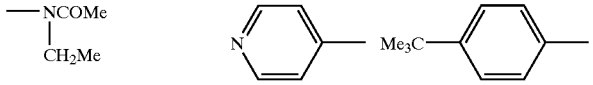 | Me₃C— 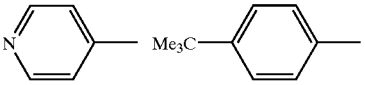 |  | 182–183 |
| 23-264 | —NCOMe<br>\|<br>CH₂Me | 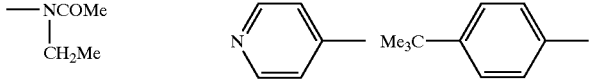 | Me₃C— 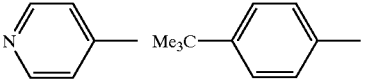 | HCl | 184–185 |
| 23-265 | —NCO— 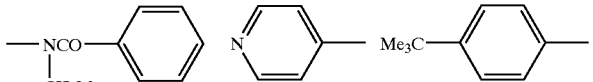<br>\|<br>CH₂Me | 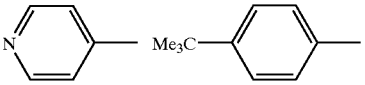 | Me₃C— 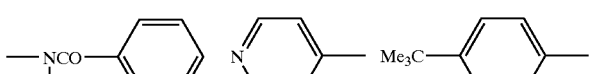 |  | 222–224 |
| 23-266 | —NCO— 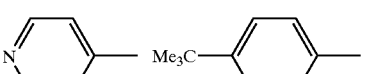<br>\|<br>CH₂Me |  | Me₃C—  | HCl | 219–222 |
| 23-267 | —NCO— 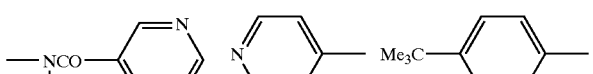<br>\|<br>CH₂Me | 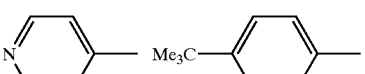 | Me₃C— 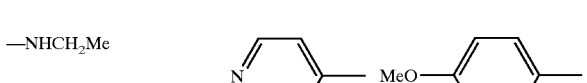 |  | 159–160 |
| 23-268 | —NCO— <br>\|<br>CH₂Me | 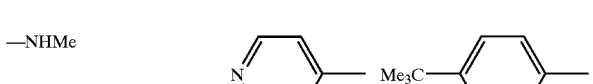 | Me₃C—  | 2HCl | 159–191 |
| 23-269 | —NHCH₂Me |  | MeO— 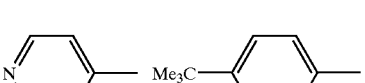 |  | 175–176 |
| 23-270 | —NHMe |  | Me₃C—  |  | 286–289 |
| 23-271 | —NHCH₂Me |  | Me₃C—  |  | 223–225 |

TABLE 26
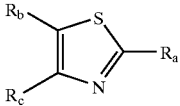
| Reference Example Compound | R$_a$ | R$_b$ | R$_c$ | additives | m.p./° C. |
|---|---|---|---|---|---|
| 23-272 | —NCOMe<br>\|<br>CH$_2$Me | 4-pyridyl | 3,5-dimethylphenyl | | 159–161 |
| 23-273 | —NCOMe<br>\|<br>CH$_2$Me | 4-pyridyl | 3,5-dimethylphenyl | HCl | 179–184 |
| 23-274 | —NCO-Ph<br>\|<br>CH$_2$Me | 4-pyridyl | 3,5-dimethylphenyl | | 178–182 |
| 23-275 | —NCO-(3-pyridyl)<br>\|<br>CH$_2$Me | 4-pyridyl | 3,5-dimethylphenyl | | 174–178 |
| 23-276 | —NH(CH$_2$)$_2$Me | 4-pyrimidyl | 3,5-dimethylphenyl | | 177–180 |
| 23-277 | —NCOMe<br>\|<br>(CH$_2$)$_2$Me | 4-pyridyl | 3,5-dimethylphenyl | | 130–132 |

TABLE 26-continued
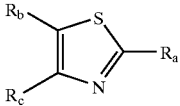

TABLE 27
| Reference Example Compound | $R_a$ | $R_b$ | $R_c$ | m.p./° C. |
|---|---|---|---|---|
| 23-284 | 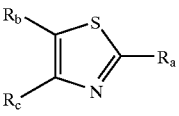 | 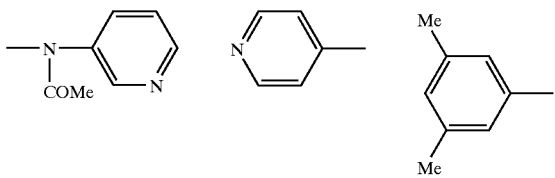 | 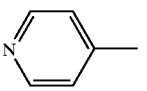 | 183–187 |
| 23-285 | —NCOMe<br>\|<br>(CH$_2$)$_2$Me | 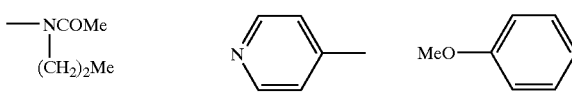 | 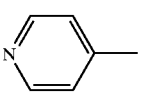 | 137–138 |
| 23-286 | —NCO—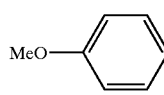<br>\|<br>(CH$_2$)$_2$Me | 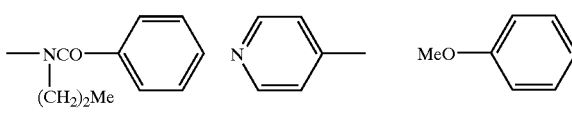 | 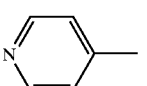 | 144–146 |
| 23-287 | —NCO—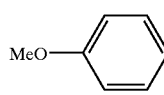<br>\|<br>(CH$_2$)$_2$Me | 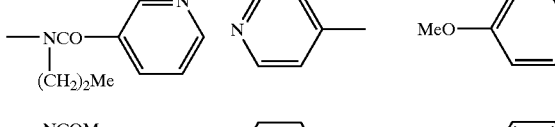 | 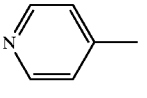 | 131–132 |
| 23-288 | —NCOMe<br>\|<br>CHMe$_2$ | 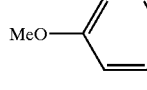 | 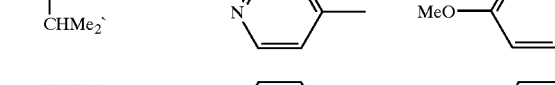 | 122–124 |
| 23-289 | —NCOMe<br>\|<br>(CH$_2$)$_2$Me | 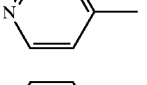 | Me$_3$C—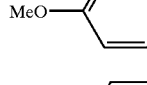 | 142–144 |
| 23-290 | —NH(CH$_2$)$_2$Me | 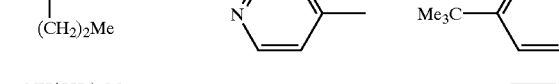 | 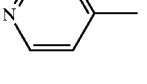 | 141–142 |
| 23-291 | —NHCHMe$_2$ | 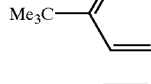 | 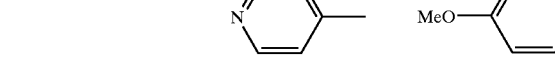 | 161–163 |
| 23-292 | —NH(CH$_2$)$_2$Me | 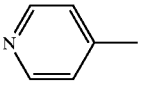 | Me$_3$C—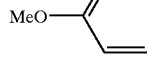 | 188–191 |
| 23-293 | —NHCO—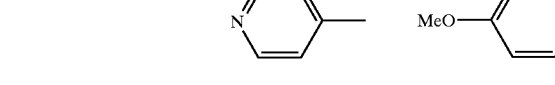 | 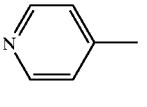 | 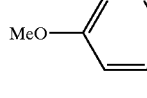 | 131–132 |
| 23-294 | —NHCOMe | 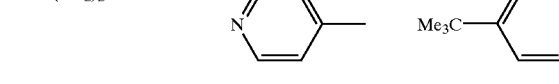 | 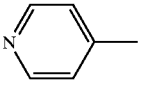 | 332–334 |

TABLE 28

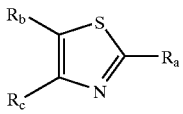

| Reference Example Compound | $R_a$ | $R_b$ | $R_c$ | m.p./° C. |
|---|---|---|---|---|
| 23-295 | —NCOCH=CH$_2$ | 4-pyridyl | 4-MeO-C$_6$H$_4$— | 236–238 |
| 23-296 | —NHCONH—C$_6$H$_5$ | 4-pyridyl | 4-MeO-C$_6$H$_4$— | 217–219 |
| 23-297 | —NHCONH—C$_6$H$_5$ | 4-pyridyl | 4-Me$_3$C-C$_6$H$_4$— | 296–298 |
| 23-298 | —NHCO-C$_6$H$_4$-CO$_2$Me | 4-pyridyl | 4-MeO-C$_6$H$_4$— | 304–306 |
| 23-299 | —NHCO-C$_6$H$_4$-CO$_2$H | 4-pyridyl | 4-MeO-C$_6$H$_4$— | 332–335 |
| 23-300 | 4-MeS-C$_6$H$_4$— | 4-pyridyl | 4-MeO-C$_6$H$_4$— | 127–128 |
| 23-301 | 4-MeS-C$_6$H$_4$— | 4-pyridyl | 4-Me$_3$C-C$_6$H$_4$— | 125–126 |
| 23-302 | 4-MeS-C$_6$H$_4$— | 4-pyridyl | 3,5-Me$_2$-C$_6$H$_3$— | 142–144 |
| 23-303 | 4-MeSO-C$_6$H$_4$— | 4-pyridyl | 4-MeO-C$_6$H$_4$— | 169–170 |
| 23-304 | 4-MeSO-C$_6$H$_4$— | 4-pyridyl | 4-Me$_3$C-C$_6$H$_4$— | 184–185 |
| 23-305 | 4-MeSO-C$_6$H$_4$— | 4-pyridyl | 3,5-Me$_2$-C$_6$H$_3$— | 199–201 |
| 23-306 | 4-MeSO$_2$-C$_6$H$_4$— | 4-pyridyl | 4-MeO-C$_6$H$_4$— | 211–212 |

TABLE 28-continued

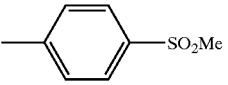

| Reference Example Compound | R$_a$ | R$_b$ | R$_c$ | m.p./° C. |
|---|---|---|---|---|
| 23-307 | -C$_6$H$_4$-SO$_2$Me | 4-pyridyl | 4-Me$_3$C-C$_6$H$_4$- | 215–217 |
| 23-308 | -C$_6$H$_4$-SO$_2$Me | 4-pyridyl | 3,5-Me$_2$-C$_6$H$_3$- | 205–207 |
| 23-309 | -C$_6$H$_4$-SMe | 4-pyridyl | 4-F-C$_6$H$_4$- | 115–118 |
| 23-310 | -C$_6$H$_4$-SMe | 4-pyridyl | 4-Cl-C$_6$H$_4$- | 147–149 |
| 23-311 | -C$_6$H$_4$-SOMe | 4-pyridyl | 4-F-C$_6$H$_4$- | 186–188 |
| 23-312 | -C$_6$H$_4$-SOMe | 4-pyridyl | 4-Cl-C$_6$H$_4$- | 187–189 |

TABLE 29

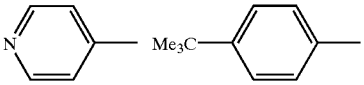

| Reference Example Compound | R$_a$ | R$_b$ | R$_c$ | additives | m.p./° C. |
|---|---|---|---|---|---|
| 23-313 | -C$_6$H$_4$-S(O$_2$)Me | 4-pyridyl | 4-F-C$_6$H$_4$- | | 191–194 |
| 23-314 | -C$_6$H$_4$-S(O$_2$)Me | 4-pyridyl | 4-Cl-C$_6$H$_4$- | | 202–204 |
| 23-315 | -NHCONH-C$_6$H$_4$- | 4-pyridyl | 3,5-Me$_2$-C$_6$H$_3$- | | 167–169 |

TABLE 29-continued

| Reference Example Compound | $R_a$ | $R_b$ | $R_c$ | additives | m.p./°C. |
|---|---|---|---|---|---|
| 23-316 | —NHCOCH₂Cl | 4-pyridyl | 4-(Me₃C)C₆H₄— | HCl | 267–269 |
| 23-317 | —NH₂ | 4-pyridyl | 4-MeO-3-(cyclopentyloxy)C₆H₃— | | 227–229 |
| 23-318 | —NHMe | 4-pyridyl | 4-MeO-3-(cyclopentyloxy)C₆H₃— | | 185–187 |
| 23-319 | —NHCOMe | 4-pyridyl | 4-MeO-3-(cyclopentyloxy)C₆H₃— | | 247–250 |
| 23-320 | —NHCH₂Ph | 4-pyridyl | 4-MeO-3-(cyclopentyloxy)C₆H₃— | | 179–183 |
| 23-321 | —NHCOCH(Cl)(C₆H₄)— | 4-pyridyl | 4-MeO-C₆H₄— | HCl | 232–236 |
| 23-322 | —NHCOCH₂-(pyrrolidin-1-yl) | 4-pyridyl | 4-(Me₃C)C₆H₄— | | 234–235 |
| 23-323 | —NHCOCH(NMe₂)(C₆H₄)— | 4-pyridyl | 4-MeO-C₆H₄— | | 233–234 |

TABLE 29-continued

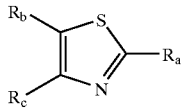

| Reference Example Compound | $R_a$ | $R_b$ | $R_c$ | additives | m.p./° C. |
|---|---|---|---|---|---|
| 23-324 | —NHCOCH(C₆H₄)(N-pyrrolidinyl) | 4-pyridyl | 4-MeO-C₆H₄ | | 175–176 |
| 23-325 | —NHCOCHMe(OH) | 4-pyridyl | 4-MeO-C₆H₄ | | 221–222 |

TABLE 30

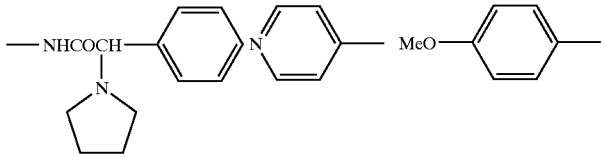

| Reference Example Compound | $R_a$ | $R_b$ | $R_c$ | m.p./° C. |
|---|---|---|---|---|
| 23-326 | 4-MeS-C₆H₄ | 4-pyridyl | 2,4-Me₂-C₆H₃ | 159–161 |
| 23-327 | 4-MeSO-C₆H₄ | 4-pyridyl | 2,4-Me₂-C₆H₃ | 161–164 |
| 23-328 | 4-MeSO₂-C₆H₄ | 4-pyridyl | 2,4-Me₂-C₆H₃ | 194–196 |
| 23-329 | —NHCOCH₂OH | 4-pyridyl | 4-MeO-C₆H₄ | 228–230 |
| 23-330 | —NHCOCH₂OH | 4-pyridyl | 4-Me₃C-C₆H₄ | 261–263 |
| 23-331 | —NHCO-C₆H₄-4-CO₂Na | 4-pyridyl | 4-MeO-C₆H₄ | 386–389 |

TABLE 30-continued
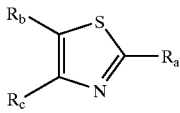
| Reference Example Compound | R_a | R_b | R_c | m.p./° C. |
|---|---|---|---|---|
| 23-332 | —NHCO—C6H4—CO2Me | 4-pyridyl | 3,5-dimethylphenyl | 300–303 |
| 23-333 | —NHCO—C6H4—CO2Na | 4-pyridyl | 3,5-dimethylphenyl | 393–395 |
| 23-334 | —N(CO-Ph)(CH2)2CO2CH2Me | 4-pyridyl | 3,5-dimethylphenyl | 123–125 |
| 23-335 | —N(CO-(3-pyridyl))(CH2)2CO2CH2Me | 4-pyridyl | 3,5-dimethylphenyl | 161–163 |
| 23-336 | —NH(CH2)2CO2CH2Me | 4-pyridyl | 3,5-dimethylphenyl | 161–162 |
| 23-337 | —NHCO—C6H4—CO2H | 4-pyridyl | 3,5-dimethylphenyl | 347–349 |
| 23-338 | —N(CO-Ph)(CH2CO2CH2Me) | 4-pyridyl | 3,5-dimethylphenyl | 166–167 |

TABLE 31
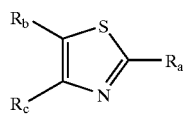
| Reference Example Compound | $R_a$ | $R_b$ | $R_c$ | m.p./° C. |
|---|---|---|---|---|
| 23-339 | —N(CO-3-pyridyl)CH₂CO₂CH₂Me | 4-pyridyl | 3,5-dimethylphenyl | 146–147 |
| 23-340 | —NHCH₂CO₂CH₂Me | 4-pyridyl | 3,5-dimethylphenyl | 142–143 |
| 23-341 | —NHCO-(3-CO₂Me-phenyl) | 4-pyridyl | 3,5-dimethylphenyl | 253–256 |
| 23-342 | —NHCO-(3-CO₂H-phenyl) | 4-pyridyl | 3,5-dimethylphenyl | 350–353 |
| 23-343 | —NHCO-(3-CO₂Na-phenyl) | 4-pyridyl | 3,5-dimethylphenyl | 257–261 |
| 23-344 | —NHCO-(4-Cl-phenyl) | 4-pyridyl | 3,5-dimethylphenyl | 276–279 |
| 23-345 | —NHCO-(2-HO-phenyl) | 4-pyridyl | 3,5-dimethylphenyl | 303–304 |

TABLE 31-continued

| Reference Example Compound | $R_a$ | $R_b$ | $R_c$ | m.p./° C. |
|---|---|---|---|---|
| 23-346 | —NH(CH$_2$)$_2$CO$_2$CH$_2$—  | 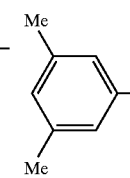 |  | 149–150 |
| 23-347 | —NHCONH—  | 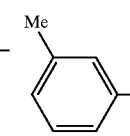 |  | 175–177 |
| 23-348 | —NHCO—  —CO$_2$Me | 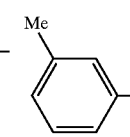 |  | 272–274 |
| 23-349 | —NHCO—  —CO$_2$H | 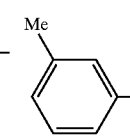 |  | 341–343 |

Reference Example 23–128

N-[4-(3,5-dimethylphenyl)-5-(4-pyridyl)-1,3-thiazol-2-yl]acetamide

To a solution of [4-(3,5-dimethylphenyl)-5-(4-pyridyl)-1,3-thiazol-2-yl]amine (0.50 g, 1.78 mmol) and 4-dimethylaminopyridine (0.06 g, 0.51 mmol) in N,N-dimethylacetamide (5 mL) was added acetyl chloride (0.21 g, 2.67 mmol) and the mixture was stirred at 80° C. for 14 h. To the reaction mixture was poured aqueous sodium hydrogencarbonate. The precipitated solid was collected by filtration. The obtained solid was washed with water and dried. The crude crystals were recrystallized from ethanol to give the title compound (0.17 g, yield 29%).

melting point: 284–286° C.

Reference Example 23–133

[4-(3,5-dimethylphenyl)-5-(4-pyridyl)-1,3-thiazol-2-yl]amine

To a solution of 2-bromo-1-(3,5-dimethylphenyl)-2-(4-pyridyl)ethanone hydrobromide (5.0 g, 13 mmol) and thiourea (1.0 g, 14 mmol) in acetonitrile (60 mL) was added dropwise triethylamine (1.9 ml, 14 mmol) and the mixture was stirred at room temperature for 3 h. The solvent was concentrated under reduced pressure and a saturated aqueous sodium hydrogencarbonate solution was added to the residue. The mixture was extracted with ethyl acetate. The organic layer was washed with water and the solvent was evaporated. The obtained crude crystals were recrystallized from ethyl acetate to give the title compound (2.0 g, 7.2 mmol, yield 55%).

melting point: 242–244° C.

Reference Example 23–137

N-[4-[4-(1,1-dimethylethyl)phenyl]-5-(4-pyridyl)-1,3-thiazol-2-yl]acetamide

To a solution of [4-[4-(1,1-dimethylethyl)phenyl]-5-(4-pyridyl)-1,3-thiazol-2-yl]amine (0.40 g, 1.29 mmol) and 4-dimethylaminopyridine (0.05 g, 0.39 mmol) in N,N-dimethylacetamide (4 mL) was added acetyl chloride (0.15 g, 1.94 mmol) and the mixture was stirred at 80° C. for 14 h. To the reaction mixture was poured aqueous sodium hydrogencarbonate and the precipitated solid was collected by filtration. The obtained solid was washed with water and dried. Crude crystals were recrystallized from ethanol to give the title compound (0.23 g, yield 50%).

melting point: 280–281° C.

Reference Example 23–143

[4-[4-(1,1-dimethylethyl)phenyl]-5-(4-pyridyl)-1,3-thiazol-2-yl]amine

To a solution of 2-bromo-1-[4-(1,1-dimethylethyl)phenyl]-2-(4-pyridyl)ethanone hydrobromide (5.0 g, 12 mmol) and thiourea (0.95 g, 13 mmol) in acetonitrile (60 mL) was added dropwise triethylamine (1.8 ml, 13 mmol) and the mixture was refluxed for 3 h. The solvent was evaporated under reduced pressure and saturated aqueous sodium hydrogencarbonate solution was added to the residue. The precipitated solid was collected by filtration. The obtained crude crystal was recrystallized from ethanol to give the title compound (2.6 g, 8.4 mmol, yield 69%).

melting point: 254–257° C.

Reference Example 23–164

N-[4-[4-(1,1-dimethylethyl)phenyl]-5-(4-pyridyl)-1,3-thiazol-2-yl]benzamide

To a solution of [4-[4-(1,1-Dimethylethyl)phenyl]-5-(4-pyridyl)-1,3-thiazol-2-yl]amine (0.50 g, 1.62 mmol) and 4-dimethylaminopyridine (0.05 g, 0.39 mmol) in N,N-dimethylacetamide (5 mL) was added benzoyl chloride (0.15 g, 1.94 mmol), and the mixture was stirred at 80° C. for 14 h. To the reaction mixture was poured an aqueous sodium hydrogencarbonate and the precipitated solid was collected by filtration. The obtained solid was washed with water and dried. The crude crystals were recrystallized from ethanol to give the title compound (0.44 g, yield 66%).

melting point: 292–294° C.

Reference Example 23–165

N-[4-[4-(1,1-dimethylethyl)phenyl]-5-(4-pyridyl)-1,3-thiazol-2-yl]nicotinamide

To a solution of [4-[4-(1,1-dimethylethyl)phenyl]-5-(4-pyridyl)-1,3-thiazol-2-yl]amine (0.50 g, 1.62 mmol) and 4-dimethylaminopyridine (0.06 g, 0.49 mmol) in N,N-dimethylacetamide (5 mL) was added nicotinoyl chloride hydrochloride (0.43 g, 2.42 mmol) and the mixture was stirred at 70° C. for 14 h. To the reaction mixture was poured aqueous sodium hydrogencarbonate solution and the precipitated solid was collected by filtration. The obtained solid was washed with water and dried. The crude crystals were recrystallized from ethanol to give the title compound (0.49 g, yield 73%).

melting point: 326–328° C.

Reference Example 23–168

N-[4-[4-(1,1-dimethylethyl)phenyl]-5-(4-pyridyl)-1,3-thiazol-2-yl]cyclopentanecarboxamide To a solution of [4-[4-(1,1-dimethylethyl)phenyl]-5-(4-pyridyl)-1,3-thiazol-2-yl]amine (0.50 g, 1.62 mmol) and 4-dimethylaminopyridine (0.06 g, 0.49 mmol) in N,N-dimethylacetamide (5 mL) was added cyclopentanecarbonyl chloride (0.32 g, 2.42 mmol) and the mixture was stirred at 70° C. for 14 h. To the reaction mixture was poured aqueous sodium hydrogencarbonate solution and the precipitated solid was collected by filtration. The obtained solid was washed with water and dried. The crude crystals were recrystallized from ethanol to give the title compound (0.43 g, yield 66%).

melting point: 309–311° C.

Reference Example 23–194

N-[4-(3,5-dimethylphenyl)-5-(4-pyridyl)-1,3-thiazol-2-yl]propionamide

To a solution of [4-(3,5-dimethylphenyl)-5-(4-pyridyl)-1,3-thiazol-2-yl]amine (0.51 g, 1.8 mmol) and 4-dimethylaminopyridine (0.06 g, 0.52 mmol) in N,N-dimethylacetamide (20 mL) was added propionyl chloride (0.18 g, 1.96 mmol) and the mixture was stirred at 80° C. for 14 h. To the reaction mixture was poured aqueous sodium hydrogencarbonate solution and the precipitated solid was collected by filtration. The obtained solid was washed with water and dried. The crude crystals were recrystallized from ethanol to give the title compound (0.41 g, yield 67%).

melting point: 291–293° C.

Reference Example 23–195

N-[4-(3,5-dimethylphenyl)-5-(4-pyridyl)-1,3-thiazol-2-yl]-2-methylpropionamide

To a solution of [4-(3,5-dimethylphenyl)-5-(4-pyridyl)-1,3-thiazol-2-yl]amine (0.50 g, 1.8 mmol) and 4-dimethylaminopyridine (0.06 g, 0.53 mmol) in N,N-dimethylacetamide (20 mL) was added 2-methylpropionyl chloride (0.20 g, 1.91 mmol) and the mixture was stirred at 80° C. for 14 h. To the reaction mixture was poured aqueous sodium hydrogencarbonate solution and the precipitated solid was collected by filtration. The obtained solid was washed with water and dried. The crude crystals were recrystallized from ethanol to give the title compound (0.52 g, yield 83%).

melting point: 270–272° C.

Reference Example 23–196

N-[4-(3,5-dimethylphenyl)-5-(4-pyridyl)-1,3-thiazol-2-yl]-2-phenylacetamide

To a solution of [4-(3,5-dimethylphenyl)-5-(4-pyridyl)-1,3-thiazol-2-yl]amine (0.51 g, 1.8 mmol) and 4-dimethylaminopyridine (0.06 g, 0.52 mmol) in N,N-dimethylacetamide (15 mL) was added 2-phenylacetyl chloride (0.32 g, 2.0 mmol) and the mixture was stirred at 80° C. for 14 h. To the reaction mixture was poured aqueous sodium hydrogencarbonate solution and the precipitated solid was collected by filtration. The obtained solid was washed with water and dried. The crude crystals were recrystallized from ethanol to give the title compound (0.33 g, yield 46%).

melting point: 226–229° C.

Reference Example 23–197

N-[4-(3,5-dimethylphenyl)-5-(4-pyridyl)-1,3-thiazol-2-yl]benzamide

To a solution of [4-(3,5-dimethylphenyl)-5-(4-pyridyl)-1,3-thiazol-2-yl]amine (0.51 g, 1.8 mmol) and 4-dimethylaminopyridine (0.06 g, 0.52 mmol) in N,N-dimethylacetamide (20 mL) was added benzoyl chloride (0.30 g, 2.15 mmol) and the mixture was stirred at 80° C. for 14 h. To the reaction mixture was poured aqueous sodium hydrogencarbonate solution and the precipitated solid was collected by filtration. The obtained solid was washed with water and dried. The crude crystals were recrystallized from ethanol to give the title compound (0.18 g, yield 26%).

melting point: 285–286° C.

Reference Example 23–198

N-[4-(3,5-dimethylphenyl)-5-(4-pyridyl)-1,3-thiazol-2-yl]cyclopentanecarboxamide To a solution of [4-(3,5-dimethylphenyl)-5-(4-pyridyl)-1,3-thiazol-2-yl]amine (0.51 g, 1.8 mmol) and 4-dimethylaminopyridine (0.07 g, 0.56 mmol) in N,N-dimethylacetamide (10 mL) was added cyclopentanecarbonyl chloride (0.33 g, 2.47 mmol) and the mixture was stirred at 70° C. for 14 h. To the reaction mixture was poured aqueous sodium hydrogencarbonate solution and the precipitated solid was collected by filtration. The obtained solid was washed with water and dried. The crude crystals were recrystallized from ethanol to give the title compound (0.41 g, yield 59%).

melting point: 275–278° C.

Reference Example 23–199

N-[4-(3,5-dimethylphenyl)-5-(4-pyridyl)-1,3-thiazol-2-yl]nicotinamide

To a solution of [4-(3,5-dimethylphenyl)-5-(4-pyridyl)-1,3-thiazol-2-yl]amine (0.52 g, 1.9 mmol) and 4-dimethylaminopyridine (0.07 g, 0.56 mmol) in N,N-dimethylacetamide (10 mL) was added nicotinoyl chloride hydrochloride (0.51 g, 2.86 mmol) and the mixture was stirred at 80° C. for 14 h. To the reaction mixture was poured aqueous sodium hydrogencarbonate solution and the precipitated solid was collected by filtration. The obtained solid was washed with water and dried. The crude crystals were recrystallized from ethanol to give the title compound (0.44 g, yield 61%).

melting point: 267–270° C.

Reference Example 23–200

N-[4-(3,5-dimethylphenyl)-5-(4-pyridyl)-1,3-thiazol-2-yl]isonicotinamide

To a solution of [4-(3,5-dimethylphenyl)-5-(4-pyridyl)-1,3-thiazol-2-yl]amine (0.51 g, 1.8 mmol) and 4-dimethylaminopyridine (0.07 g, 0.56 mmol) in N,N-dimethylacetamide (10 mL) was added isonicotinoyl chloride hydrochloride (0.48 g, 2.72 mmol) and the mixture was stirred at 80° C. for 14 h. To the reaction mixture was poured aqueous sodium hydrogencarbonate solution and the precipitated solid was collected by filtration. The obtained solid was washed with water and dried. The crude crystals were recrystallized from ethanol to give the title compound (0.22 g, yield 32%).

melting point; 302–304° C.

Reference Example 23–201

N-[4-(3,5-dimethylphenyl)-5-(4-pyridyl)-1,3-thiazol-2-yl]-N'-ethylurea

To a solution of [4-(3,5-dimethylphenyl)-5-(4-pyridyl)-1,3-thiazol-2-yl]amine (0.51 g, 1.8 mmol) in N,N-dimethylacetamide (10 mL) was added ethyl isocyanate (0.20 g, 2.8 mmol) and the mixture was stirred at 80° C. for 14 h. To the reaction mixture was poured aqueous sodium hydrogencarbonate solution and the precipitated solid was collected by filtration. The obtained solid was washed with water and dried. The crude crystals were recrystallized from ethanol to give the title compound (0.27 g, yield 42%).

melting point: 202–203° C.

Reference Example 23–202

N-[4-(3,5-dimethylphenyl)-5-(4-pyridyl)-1,3-thiazol-2-yl]-N'-propylurea

To a solution of [4-(3,5-dimethylphenyl)-5-(4-pyridyl)-1,3-thiazol-2-yl]amine (0.51 g, 1.8 mmol) in N,N-dimethylacetamide (15 mL) was added propyl isocyanate (0.23 g, 2.67 mmol) and the mixture was stirred at 80° C. for 14 h. To the reaction mixture was poured aqueous sodium hydrogencarbonate solution and the precipitated solid was collected by filtration. The obtained solid was washed with water and dried. The crude crystals were recrystallized from ethanol to give the title compound (0.23 g, yield 33%).

melting point: 128–130° C.

Reference Example 23–246

N-[4-(3,5-dimethylphenyl)-5-(4-pyridyl)-1,3-thiazol-2-yl]pyrazinecarboxamide

To a solution of [4-(3,5-dimethylphenyl)-5-(4-pyridyl)-1,3-thiazol-2-yl]amine (0.50 g, 1.8 mmol) and 4-dimethylaminopyridine (0.06 g, 0.53 mmol) in N,N-dimethylacetamide (5 mL) was added pyrazinecarbonyl chloride (0.44 g, 2.7 mmol) and the mixture was stirred at 70° C. for 14 h. To the reaction mixture was poured aqueous sodium hydrogencarbonate solution and the precipitated solid was collected by filtration. The obtained solid was washed with water and dried. The crude crystals were recrystallized from ethanol to give the title compound (0.41 g, yield 59%).

melting point: 269–270° C.

Reference Example 24

1-bromo-3-ethylbenzene

To a 50% aqueous sulfuric acid solution (43.6 g) of 3-ethylaniline (10.0 g, 82.5 mmol) was added dropwise at 0° C. an aqueous solution (16.5 mL) of sodium nitrite (6.83 g, 99.0 mmol) over 30 min. The obtained reaction mixture was stirred at 0° C. for 45 min. This diazonium salt solution was added by small portions to a 48% hydrobromic acid solution (82.5 mL) of copper(I) bromide (12.4 g, 86.6 mmol) being gently refluxed under heating. After the addition, the reaction mixture was refluxed under heating for 30 min. The reaction mixture was cooled to room temperature and extracted with ether. The extract was washed successively with 1N aqueous sodium hydroxide solution and saturated brine, filtrated, dried and concentrated. The residue was purified by silica gel column chromatography (hexane-ethyl acetate=20:1) to give the title compound (6.13 g, yield 40%). oil.

$^1$H-NMR (CDCl$_3$) δ: 1.23 (3H, t, J=7.5 Hz), 2.63 (2H, q, J=7.5 Hz), 7.11–7.20 (2H, m), 7.28–7.38 (2H, m).

Reference Example 25

In accordance with Reference Example 24, the following Reference Example compound 25 was synthesized using 3-(1-methylethyl)aniline instead of 3-ethylaniline.

Reference Example Compound 25: 1-bromo-3-(1-methylethyl)benzene oil.

$^1$H-NMR (CDCl$_3$) δ: 1.24 (6H, d, J=7.0 Hz), 2.77–2.99 (1H, m), 7.03–7.16 (2H, m), 7.27–7.34 (1H, m), 7.37 (1H, s).

Reference Example 26

3-ethylbenzoic acid

A solution (45 mL) of 1-bromo-3-ethylbenzene (5.1 g, 28 mmol) in tetrahydrofuran was added dropwise to a mixture (5.0 mL) of magnesium turnings (0.74 g, 31 mmol) and tetrahydrofuran under an argon atmosphere, and the mixture was stirred as it was for 30 min. The reaction mixture was added to the crushed dry ice and the mixture was stirred as it was for 1 h. 1N Hydrochloric acid was added to the reaction mixture and the mixture was extracted with ethyl acetate. The extract was dried, filtrated and concentrated. The residue was purified by silica gel column chromatography (hexane-ethyl acetate=5:1) to give the title compound (3.87 g, yield 93%). oil.

$^1$H-NMR (CDCl$_3$) δ: 1.28 (3H, t, J=7.5 Hz), 2.73 (2H, q, J=7.5 Hz), 7.34–7.50 (2H, m), 7.92–7.98 (2H, m).

Reference Example 27

In accordance with Reference Example 26, the following Reference Example compounds 27-1 and 27-2 were synthesized using 1-bromo-3-(1-methylethyl)benzene or 1-bromo-4-fluoro-3-methylbenzene instead of 1-bromo-3-ethylbenzene.

Reference Example Compound 27-1: 3-(1-methylethyl) benzoic acid oil.

$^1$H-NMR (CDCl$_3$) δ: 1.29 (6H, d, J=7.0 Hz), 2.98–3.06 (1H, m), 7.38–7.54 (2H, m), 7.90–8.02 (2H, m).

Reference Example Compound 27-2: 4-fluoro-3-methylbenzoic acid
melting point: 165–167° C.

Reference Example 28

3-ethylbenzoyl chloride

3-Ethylbenzoic acid (9.40 g, 62.6 mmol) was added slowly to thionyl chloride (45 mL) at 0° C., and N,N-dimethylformamide (3 drops) was added dropwise. The obtained reaction mixture was refluxed under heating as it was for 2 h. The reaction mixture was concentrated and used without purification in the next reaction.

Reference Example 29

In accordance with Reference Example 28, the following Reference Example compounds 29-1 to 29-3 were synthesized using 3-(1-methylethyl)benzoic acid, 4-fluoro-3-methylbenzoic acid or 4-cyclohexylbenzoic acid instead of 3-ethylbenzoic acid.

Reference Example Compound 29-1: 3-(1-methylethyl) benzoyl chloride
Used in the next reaction without purification.
Reference Example Compound 29-2: 4-fluoro-3-methylbenzoyl chloride
Used in the next reaction without purification.
Reference Example Compound 29-3: 4-cyclohexylbenzoyl chloride
Used in the next reaction without purification.

Reference Example 30

In accordance with Reference Example 14, the following Reference Example compounds 30-1 to 30-7 were synthesized respectively using 3-trifluoromethylbenzoyl chloride, 3,5-dichlorobenzoyl chloride, 3-ethylbenzoyl chloride, 3-(1-methylethyl)benzoyl chloride, 4-fluoro-3-methylbenzoyl chloride, 4-cyclohexylbenzoyl chloride and 3-fluorobenzoyl chloride instead of 4-chlorobenzoyl chloride.

Reference Example Compound 30-1: N-(3-trifluoromethylbenzoyl)propyleneimine oil.

$^1$H-NMR (CDCl$_3$) δ: 1.42 (3H, d, J=5.5 Hz), 2.20 (1H, d, J=3.3 Hz), 2.56–2.67 (2H, m), 7.61 (1H, t, J=7.7 Hz), 7.81 (1H, d, J=7.7 Hz), 8.21 (1H, d, J=7.7 Hz), 8.30 (1H, s).

Reference Example Compound 30-2; N-(3,5-dichlorobenzoyl)propyleneimine oil.

$^1$H-NMR (CDCl$_3$) δ: 1.40 (3H, d, J=5.1 Hz), 2.19 (1H, d, J=3.3 Hz), 2.57 (1H, t, J=5.5 Hz), 2.57–2.70 (1H, m), 7.54 (1H, t, J=1.8 Hz), 7.88 (2H, d, J=1.8 Hz).

Reference Example Compound 30-3: N-(3-ethylbenzoyl) propyleneimine oil.

$^1$H-NMR (CDCl$_3$) δ: 1.27 (3H, t, J=7.5 Hz), 1.40 (3H, d, J=5.5 Hz), 2.14 (1H, d, J=2.9 Hz), 2.52–2.61 (2H, m), 2.71 (2H, q, J=7.5 Hz), 7.32–7.41 (2H, m), 7.81–7.89 (2H, m).

Reference Example Compound 30-4: N-[3-(1-methylethyl) benzoyl]propyleneimine oil.

$^1$H-NMR (CDCl$_3$) δ: 1.29 (6H, d, J=7.0 Hz), 1.40 (3H, d, J=5.9 Hz), 2.14 (1H, d, J=3.7 Hz), 2.51–2.64 (2H, m), 2.87–3.10 (1H, m), 7.33–7.46 (2H, m), 7.84 (1H, dt, J=7.0, 1.8 Hz), 7.91 (1H, s).

Reference Example Compound 30-5: N-(4-fluoro-3-methylbenzoyl)propyleneimine oil.

$^1$H-NMR (CDCl$_3$) δ: 1.39 (3H, d, J=5.4 Hz), 2.14 (1H, d, J=3.4 Hz), 2.33 (s, 3H), 2.51–2.61 (2H, m), 7.06 (1H, t, J=8.8 Hz), 7.81–7.90 (2H, m).

Reference Example Compound 30-6: N-(4-cyclohexylbenzoyl)propyleneimine oil.

$^1$H-NMR (CDCl$_3$) δ: 1.22–1.54 (7H, m), 1.67–1.89 (6H, m), 2.12 (1H, d, J=3.2 Hz), 2.52–2.60 (3H, m), 7.28 (2H, d, J=8.3 Hz), 7.95 (2H, d, J=8.3 Hz).

Reference Example Compound 30-7: N-(3-fluorobenzoyl) propyleneimine oil.

$^1$H-NMR (CDCl$_3$) δ: 1.40 (3H, d, J=5.5 Hz), 2.16 (1H, d, J=3.3 Hz), 2.52–2.68 (2H, m), 7.25 (1H, ddd, J=8.4, 2.6, 1.1 Hz), 7.43 (1H, ddd, J=8.1, 7.7, 5.5 Hz), 7.69 (1H, ddd, J=8.1, 2.6, 1.5 Hz), 7.81 (1H, ddd, J=7.7, 1.5, 1.1 Hz).

Reference Example 31

In accordance with Reference Example 16, the following Reference Example compounds 31-1 to 31-7 were synthesized respectively using N-(3-trifluoromethylbenzoyl) propyleneimine, N-(3,5-dichlorobenzoyl)propyleneimine, N-(3-ethylbenzoyl)propyleneimine, N-[3-(1-methylethyl) benzoyl]propyleneimine, N-(4-fluoro-3-methylbenzoyl) propyleneimine, N-(4-cyclohexylbenzoyl)propyleneimine and N-(3-fluorobenzoyl)propyleneimine instead of N-(2-chlorobenzoyl)propyleneimine.

Reference Example Compound 31-1: 2-(4-pyridyl)-1-(3-trifluoromethylphenyl)ethanone oil.

$^1$H-NMR (CDCl$_3$) δ: 4.33 (2H, s), 7.21 (2H, d, J=6.0 Hz), 7.65 (1H, dd, J=8.4, 7.7 Hz), 7.87 (1H, d, J=7.7 Hz), 8.18 (1H, d, J=8.4 Hz), 8.26 (1H, s), 8.59 (2H, d, J=6.0 Hz).

Reference Example Compound 31-2: 1-(3,5-dichlorophenyl)-2-(4-pyridyl)ethanone
melting point: 163–164° C.

Reference Example Compound 31-3: 1-(3-ethylphenyl)-2-(4-pyridyl)ethanone
melting point: 102–103° C.

Reference Example Compound 31-4: 1-[3-(1-methylethyl) phenyl]-2-(4-pyridyl)ethanone
melting point: 50–52° C.

Reference Example Compound 31-5: 1-(4-fluoro-3-methylphenyl)-2-(4-pyridyl)ethanone
melting point: 86–88° C.

Reference Example Compound 31-6: 1-(4-cyclohexylphenyl)-2-(4-pyridyl)ethanone oil.

$^1$H-NMR (CDCl$_3$) δ: 1.32–1.52 (5H, m), 1.77–1.89 (5H, m), 2.58 (1H, m), 4.26 (2H, s), 7.20 (2H, d, J=6.3 Hz), 7.32 (2H, d, J=8.4 Hz), 7.93 (2H, d, J=8.4 Hz), 8.56 (2H, d, J=6.3 Hz).

Reference Example Compound 31-7; 1-(3-fluorophenyl)-2-(4-pyridyl)ethanone
Amorphous powder.
¹H-NMR (CDCl₃) δ: 4.28 (2H, s), 7.20 (2H, d, J=6.2 Hz), 7.33 (1H, ddd, J=8.1, 2.6, 1.1 Hz), 7.49 (1H, ddd, J=8.1, 7.7, 5.5 Hz), 7.68 (1H, ddd, J=9.5, 2.6, 1.5 Hz), 7.79 (1H, ddd, J=7.7, 1.5, 1.1 Hz), 8.58 (2H, d, J=6.2 Hz).

Reference Example 32

In accordance with Reference Example 17, the following Reference Example compounds 32-1 to 32-4 were synthesized using 2,4-lutidine or γ-collidine instead of γ-picoline.
Reference Example Compound 32-1: 1-(3-methylphenyl)-2-(2-methyl-4-pyridyl)ethanone.
melting point: 56–57° C.
Reference Example Compound 32-2: 1-(3,5-dimethylphenyl)-2-(2-methyl-4-pyridyl)ethanone oil.
¹H-NMR (CDCl₃) δ: 2.38 (6H, s), 2.54 (3H, s), 4.21 (2H, s), 6.98–7.10 (1H, m), 7.01 (1H, m), 7.06 (1H, s), 7.23 (1H, s), 7.60 (2H, s), 8.42–8.45 (1H, m).
Reference Example Compound 32-3: 2-(2,6-dimethyl-4-pyridyl)-1-(3-methylphenyl)ethanone
melting point: 46–48° C.
Reference Example Compound 32-4: 1-(3,5-dimethylphenyl)-2-(2,6-dimethyl-4-pyridyl)ethanone
melting point: 135–136° C.

Reference Example 33

2-(2-tert-butoxycarbonylamino-4-pyridyl)-1-(4-methoxyphenyl)ethanone

A solution of 2-tert-butoxycarbonylamino-4-methylpyridine (20 g, 97 mmol) in anhydrous tetrahydrofuran (300 mL) was cooled to −78° C. and 1.6 M n-butyllithium/hexane solution (140 mL, 0.23 mol) was added dropwise with stirring. After completion of the dropwise addition, the mixture was stirred at room temperature for 30 min and cooled to −78° C. A solution of N-(4-methoxybenzoyl)propyleneimine (25 g, 0.13 mol) in anhydrous tetrahydrofuran (50 mL) was added dropwise. After completion of the dropwise addition, the mixture was stirred at room temperature for 2 h. To the reaction mixture were added water (100 mL) and isopropyl ether (300 mL), and the obtained crude crystals were collected by filtration. The crude crystals were recrystallized from tetrahydrofuran-hexane to give the title compound (23 g, yield 69%).
melting point: 187–190° C.

Reference Example 34

In accordance with Reference Example 33, the following Reference Example compound 34-1 and 34-2 were synthesized respectively using N-(3-methylbenzoyl)propyleneimine and N-(3,5-dimethylbenzoyl)propyleneimine instead of N-(4-methoxybenzoyl)propyleneneimine.
Reference Example Compound 34-1: 2-(2-tert-butoxycarbonylamino-4-pyridyl)-1-(3-methylphenyl)ethanone
melting point: 144–146° C.
Reference Example Compound 34-2: 2-(2-tert-butoxycarbonylamino-4-pyridyl)-1-(3,5-dimethylphenyl)ethanone
melting point: 133–136° C.

Reference Example 35

2-fluoro-4-methylpyridine

Synthesized in accordance with the method described in Journal of Medicinal Chemistry, vol. 33, pp. 1667–1675 (1990). boiling point: 82–86° C. (10 kpa).

Reference Example 36

2-(2-fluoro-4-pyridyl)-1-(3-methylphenyl)ethanone

A solution of diisopropylamine (44 mL, 0.31 mol) in anhydrous tetrahydrofuran (300 mL) was cooled to −78° C. under an argon atmosphere, and 1.6 M n-butyllithium/hexane solution (190 mL, 0.31 mol) was added dropwise with stirring. After completion of the dropwise addition, the mixture was stirred for 10 min, and a solution of 2-fluoro-4-methylpyridine (34.5 g, 0.31 mol) in anhydrous tetrahydrofuran (30 mL) was added. The reaction mixture was stirred at −10° C. for 30 min. The reaction solution was cooled to −78° C. and a solution of N-(3-methylbenzoyl)propyleneimine (52 g, 0.30 mol) in anhydrous tetrahydrofuran (30 mL) was added dropwise. After completion of dropwise addition, the mixture was stirred at room temperature for 2 h. To the reaction mixture was added water (100 mL), and the mixture was extracted with ethyl acetate. The extract was washed with water, dried and the solvent was evaporated. The residue was recrystallized from isopropyl ether to give the title compound (35 g, yield 52%).
melting point: 66–67° C.

Reference Example 37

In accordance with Reference Example 36, the following Reference Example compound 37 was synthesized using N-(3-methoxybenzoyl)propyleneimine instead of N-(3-methylbenzoyl)propyleneimine.
Reference Example Compound 37: 2-(2-fluoro-4-pyridyl)-1-(3-methoxyphenyl)ethanone oil
¹H-NMR (CDCl₃) δ: 3.86 (3H, s), 4.31 (2H, s), 6.86 (1H, s), 7.03–7.19 (2H, m), 7.31–7.59 (3H, m), 8.18 (1H, d, J=5.6 Hz).

Reference Example 38

In accordance with Reference Example 21, the following Reference Example compounds 38-1 to 38-21 were synthesized respectively using 2-methylbenzonitrile, 3-methylbenzonitrile, 4-methylbenzonitrile, 2-chlorobenzonitrile, 3-chlorobenzonitrile, 4-chlorobenzonitrile, 3-methoxybenzonitrile, 4-methoxybenzonitrile, 2-fluorobenzonitrile, 3-fluorobenzonitrile, 4-fluorobenzonitrile, 4-nitrobenzonitrile, piperonylonitrile, 3-methoxycarbonylbenzonitrile, 4-methoxycarbonylbenzonitrile, butyronitrile, isobutyronitrile, valeronitrile, hexanenitrile, 3-phenylpropionitrile and 4-phenylbutyronitrile instead of 4-methylthiobenzonitrile.
Reference Example Compound 38-1: 2-methyl(thiobenzamide) oil
¹H-NMR (CDCl₃) δ: 2.37 (3H, s), 6.88 (1H, br s), 7.06–7.23 (3H, m), 7.24–7.31 (1H, m), 7.88 (1H, br s).
Reference Example Compound 38-2: 3-methyl(thiobenzamide)
melting point: 88–89° C.
Reference Example Compound 38-3: 4-methyl(thiobenzamide)
melting point: 172–174° C.
Reference Example Compound 38-4: 2-chlorothiobenzamide
melting point: 58–59° C.
Reference Example Compound 38-5: 3-chlorothiobenzamide
melting point: 114–115° C.
Reference Example Compound 38-6: 4-chlorothiobenzamide melting point: 130–131° C.

Reference Example Compound 38-7: 3-methoxythiobenzamide oil
$^1$H-NMR (CDCl$_3$) δ: 3.86 (3H, s), 7.02–7.08 (1H, m), 7.31–7.36 (3H, m), 7.46–7.49 (1H, m), 7.76 (1H, br s).

Reference Example Compound 38-8: 4-methoxythiobenzamide
melting point: 148–149° C.

Reference Example Compound 38-9: 2-fluorothiobenzamide
melting point: 113–114° C.

Reference Example compound 38-10: 3-fluorothiobenzamide
melting point: 151–152° C.

Reference Example Compound 38-11: 4-fluorothiobenzamide
melting point: 156–157° C.

Reference Example Compound 38-12: 4-nitrothiobenzamide
melting point: 159–160° C.

Reference Example Compound 38-13: thiopiperonylamide
melting point: 188–189° C.

Reference Example Compound 38-14: 3-methoxycarbonyl-thiobenzamide
melting point: 140–141° C.

Reference Example Compound 38-15: 4-methoxycarbonylthiobenzamide
melting point: 191–192° C.

Reference Example Compound 38-16: thiobutylamide oil
$^1$H-NMR (CDCl$_3$) δ: 0.99 (3H, t, J=7.6 Hz), 1.72–1.93 (2H, m), 2.64 (2H, t, J=7.6 Hz), 7.02 (1H, br s), 7.77 (1H, br s).

Reference Example Compound 38-17: thioisobutylamide oil
$^1$H-NMR (CDCl$_3$) δ: 1.28 (6H, d, J=5.8 Hz), 2.79–2.96 (1H, m), 6.99 (1H, br s), 7.71 (1H, br s).

Reference Example Compound 38-18: thiovaleramide oil
$^1$H-NMR (CDCl$_3$) δ: 0.94 (3H, t, J=7.3 Hz), 1.31–1.49 (2H, m), 1.68–1.83 (2H, m), 2.67 (2H, t, J=7.7 Hz), 6.92 (1H, br s), 7.73 (1H, br s).

Reference Example Compound 38-19: hexanethioamide oil
$^1$H-NMR (CDCl$_3$) δ: 0.90 (3H, t, J=6.9 Hz), 1.22–1.45 (4H, m), 1.70–1.84 (2H, m), 2.66 (2H, t, J=7.5 Hz), 7.05 (1H, br s), 7.91 (1H, br s).

Reference Example Compound 38-20: 3-phenyl (thiopropionamide)
melting point: 83–84° C.

Reference Example Compound 38-21: 4-phenyl (thiobutylamide)
melting point: 60–61° C.

Reference Example 39

In accordance with Reference Example 6, the following Reference Example compounds 39-1 to 39-13 were synthesized respectively using 2-(4-pyridyl)-1-(3-trifluoromethylphenyl)ethanone, 1-(3,5-dichlorophenyl)-2-(4-pyridyl ethanone, 1-(3-ethylphenyl)-2-(4-pyridyl)ethanone, 1-[3-(1-methylethyl)phenyl]-2-(4-pyridyl)ethanone, 1-(4-fluoro-3-methylphenyl)-2-(4-pyridyl)ethanone, 1-(4-cyclohexylphenyl)-2-(4-pyridyl)ethanone, 1-(3-fluorophenyl)-2-(4-pyridyl)ethanone, 2-(2-fluoro-4-pyridyl)-1-(3-methylphenyl)ethanone, 2-(2-fluoro-4-pyridyl)-1-(3-methoxyphenyl)ethanone, 1-(3-methylphenyl)-2-(2-methyl-4-pyridyl)ethanone, 1-(3,5-dimethylphenyl)-2-(2-methyl-4-pyridyl)ethanone, 2-(2,6-dimethyl-4-pyridyl)-1-(3-methylphenyl)ethanone and 1-(3,5-dimethylphenyl)-2-(2,6-dimethyl-4-pyridyl)ethanone instead of 1-(4-methoxyphenyl)-2-(3-pyridyl)ethanone.

Reference Example Compound 39-1: 2-bromo-2-(4-pyridyl)-1-(3-trifluoromethylphenyl)ethanone hydrobromide
Used in the next reaction without purification.

Reference Example Compound 39-2: 2-bromo-1-(3,5-dichlorophenyl)-2-(4-pyridyl)ethanone hydrobromide
melting point: 253–254° C.

Reference Example Compound 39-3: 2-bromo-1-(3-ethylphenyl)-2-(4-pyridyl)ethanone hydrobromide
melting point: 146–148° C.

Reference Example Compound 39-4: 2-bromo-1-[3-(1-methylethyl)phenyl]-2-(4-pyridyl)ethanone hydrobromide
melting point: 143–144° C.

Reference Example Compound 39-5: 2-bromo-1-(4-fluoro-3-methylphenyl)-2-(4-pyridyl)ethanone hydrobromide
melting point: 211–214° C.

Reference Example Compound 39-6: 2-bromo-1-(4-cyclohexylphenyl)-2-(4-pyridyl)ethanone hydrobromide
melting point: 189–191° C.

Reference Example Compound 39-7: 2-bromo-1-(3-fluorophenyl)-2-(4-pyridyl)ethanone hydrobromide
melting point: 191–194° C.

Reference Example Compound 39-8: 2-bromo-2-(2-fluoro-4-pyridyl)-1-(3-methylphenyl)ethanone hydrobromide
Used in the next reaction without purification.

Reference Example Compound 39-9: 2-bromo-2-(2-fluoro-4-pyridyl)-1-(3-methoxyphenyl)ethanone hydrobromide
Used in the next reaction without purification.

Reference Example Compound 39-10: 2-bromo-1-(3-methylphenyl)-2-(2-methyl-4-pyridyl)ethanone hydrobromide
melting point: 144–146° C.

Reference Example Compound 39-11: 2-bromo-1-(3,5-dimethylphenyl)-2-(2-methyl-4-pyridyl)ethanone hydrobromide
Used in the next reaction without purification.

Reference Example Compound 39-12: 2-bromo-2-(2,6-dimethyl-4-pyridyl)-1-(3-methylphenyl)ethanone hydrobromide
Used in the next reaction without purification.

Reference Example Compound 39-13: 2-bromo-1-(3,5-dimethylphenyl)-2-(2,6-dimethyl-4-pyridyl)ethanone hydrobromide
melting point: 208–212° C.

Reference Example 40

2-bromo-2-(2-tert-butoxycarbonylamino-4-pyridyl)-1-(4-methoxyphenyl)ethanone hydrobromide To a solution of 2-(2-tert-butoxycarbonylamino-4-pyridyl)-1-(4-methoxyphenyl)ethanone (0.36 g, 1.1 mmol) in acetic acid (5 mL) was added bromine (0.058 mL, 1.1 mmol) and the mixture was stirred at room temperature for 1 h. The reaction mixture was concentrated and the residue was washed with isopropyl ether to give the title compound (0.44 g, yield 82%).
Amorphous Powder
$^1$H-NMR (CDCl$_3$) δ: 1.55 (6H, s), 3.92 (3H, s), 6.35 (1H, s), 6.99–7.03 (2H, m), 7.66 (1H, dd, J=6.6, 1.8 Hz), 8.02–8.07 (2H, M), 8.20 (1H, d, J=6.6 Hz), 8.70 (2H, d, J=1.8 Hz), 11.02 (1H, br s).

Reference Example 41

In accordance with Reference Example 40, the following Reference Example compounds 41-1 and 41-2 were synthesized respectively using 2-(2-tert-butoxycarbonylamino-4-pyridyl)-1-(3-methylphenyl)ethanone and 2-(2-tertbutoxycarbonylamino-4-pyridyl)-1-(3,5-dimethylphenyl)ethanone instead of 2-(2-tert-butoxycarbonylamino-4-pyridyl)-1-(4-methoxyphenyl)ethanone.
Reference Example Compound 41-1: 2-bromo-2-(2-tert-butoxycarbonylamino-4-pyridyl)-1-(3-methylphenyl)ethanone hydrobromide
Used in the next reaction without purification.
Reference Example Compound 41-2: 2-bromo-2-(2-tert-butoxycarbonylamino-4-pyridyl)-1-(3,5-dimethylphenyl)ethanone hydrobromide
Used in the next reaction without purification.

Reference Example 42 ethyl (4-phenyl-1-piperazinyl)carbothioylcarbamate

1-Phenylpiperazine (10 g, 62 mmol) was added to a solution of ethyl isothiocyanatoformate (8.1 g, 62 mmol) in acetone (30 mL) and the mixture was refluxed under heating for 1 h. The reaction mixture was concentrated and the crude crystals were recrystallized from ethyl acetate to give the title compound (13 g, yield 73%).

melting point: 134–135° C.

Reference Example 43

4-phenyl-1-piperazinecarbothioamide

Ethyl (4-phenyl-1-piperazinyl)carbothioylcarbamate (13 g, 44 mmol) was added to conc. hydrochloric acid (44 mL) and the mixture was stirred at 80° C. for 2 h. The reaction mixture was made basic with 8N aqueous sodium hydroxide solution and the crystals were collected by filtration. The crystals were washed with water and dried to give the title compound (6.1 g, yield 63%).

melting point: 178–179° C.

Reference Example 44

In accordance with the methods described in Reference Examples 8 to 12, Reference Example 44-1, JP-A-61-10580 and U.S. Pat. No. 4,612,321, Reference Example compounds 44-1 to 44-129 shown in the following Tables 32–42 were synthesized.

TABLE 32

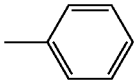

| Reference Example Compound | $R_a$ | $R_b$ | $R_c$ | m.p./° C. |
|---|---|---|---|---|
| 44-1 | 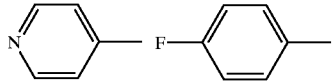 | 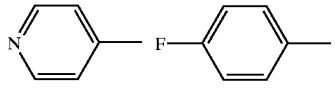 | 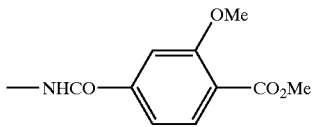 | 135–137 |
| 44-2 | —NH₂ | 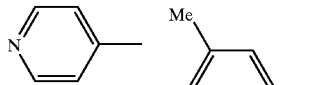 | 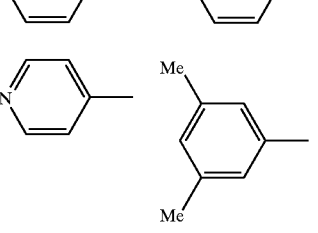 | 267–269 |
| 44-3 | 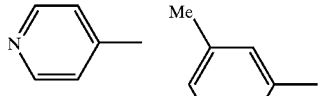 | 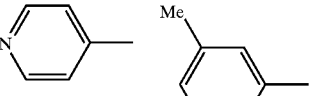 | 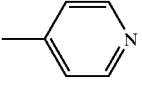 | 246–248 |
| 44-4 | —Me | 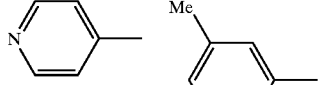 | 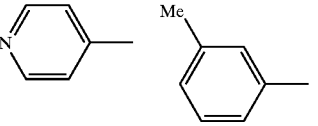 | 74–75 |
| 44-5 | 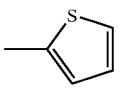 | 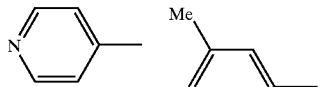 | | 110–111 |
| 44-6 | 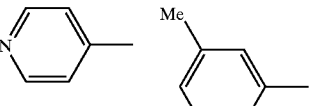 | | | 107–108 |

TABLE 32-continued
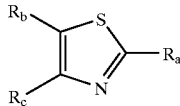
| Reference Example Compound | $R_a$ | $R_b$ | $R_c$ | m.p./° C. |
|---|---|---|---|---|
| 44-7 | 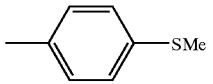 | 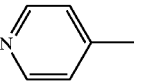 | 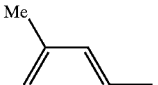 | 101–102 |
| 44-8 | 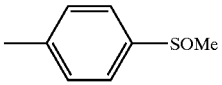 | 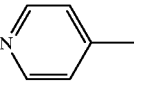 | 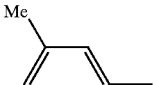 | 188–189 |
| 44-9 | —NH$_2$ |  | 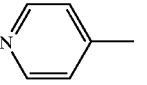 | 229–230 |
| 44-10 | —NHCOMe | 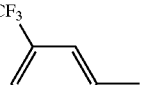 |  | 247–249 |
| 44-11 | 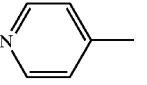 | 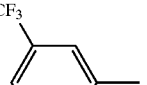 | 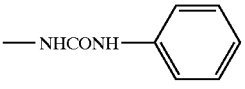 | 208–210 |
| 44-12 | 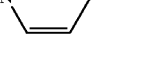 | 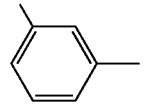 | 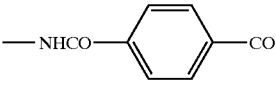 | 279–281 |
| 44-13 | 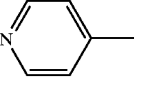 | 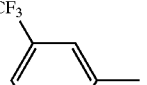 | 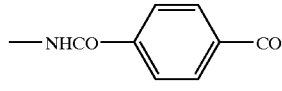 | 351–353 |
| 44-14 | 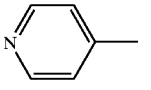 | 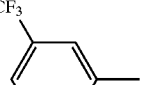 | 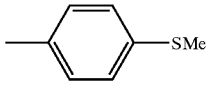 | 92–93 |

TABLE 33

Structure: 2-Ra, 4-Rc, 5-Rb thiazole

| Reference Example Compound | Ra | Rb | Rc | m.p./° C. |
|---|---|---|---|---|
| 44-15 | 4-(SMe)-C₆H₄– | 4-pyridyl | 4-Me-C₆H₄– | 153–154 |
| 44-16 | 4-(SOMe)-C₆H₄– | 4-pyridyl | 4-Me-C₆H₄– | 172–173 |
| 44-17 | 4-(SO₂Me)-C₆H₄– | 4-pyridyl | 4-Me-C₆H₄– | 221–222 |
| 44-18 | –NHCO-(2-OMe,4-CO₂H-C₆H₃) | 4-pyridyl | 3,5-diMe-C₆H₃– | 259–262 |
| 44-19 | –NHMe | 4-pyridyl | 3-Me-C₆H₄– | 199–202 |
| 44-20 | –NHCH₂Me | 4-pyridyl | 3-Me-C₆H₄– | 190–191 |
| 44-21 | –NMeCOMe | 4-pyridyl | 3-Me-C₆H₄– | 169–170 |
| 44-22 | –NMeCONH-C₆H₅ | 4-pyridyl | 3-Me-C₆H₄– | 190–191 |
| 44-23 | –NMeCO-(4-CO₂Me-C₆H₄) | 4-pyridyl | 3-Me-C₆H₄– | 134–135 |
| 44-24 | –CH₂Me | 4-pyridyl | 3-Me-C₆H₄– | 56–58 |

TABLE 33-continued

[Thiazole structure with Rb at 5-position, Ra at 2-position, Rc at 4-position]

| Reference Example Compound | Ra | Rb | Rc | m.p./° C. |
|---|---|---|---|---|
| 44-25 | 4-(CO2Me)phenyl | pyridin-4-yl | 3-methylphenyl | 152–153 |
| 44-26 | 4-(SO2Me)phenyl | pyridin-4-yl | 3-methylphenyl | 171–174 |
| 44-27 | —NHCOMe | pyridin-4-yl | 3,5-dichlorophenyl | 307–308 |
| 44-28 | —NH2 | pyridin-4-yl | 3-fluorophenyl | 263–264 |

TABLE 34

[Thiazole structure with Rb at 5-position, Ra at 2-position, Rc at 4-position]

| Reference Example Compound | Ra | Rb | Rc | m.p./° C. |
|---|---|---|---|---|
| 44-29 | —NHCOMe | pyridin-4-yl | 3-fluorophenyl | 326–328 |
| 44-30 | —NHCONH-phenyl | pyridin-4-yl | 3-fluorophenyl | 227–228 |
| 44-31 | 4-(SMe)phenyl | pyridin-4-yl | 3-fluorophenyl | 117–119 |

TABLE 34-continued

| Reference Example Compound | Ra | Rb | Rc | m.p./° C. |
|---|---|---|---|---|
| 44-32 | 4-CO2Me-phenyl | 4-pyridyl | 3-F-phenyl | 144–145 |
| 44-33 | —NH2 | 4-pyridyl | 4-(4-methylphenyl)cyclohexyl | 232–234 |
| 44-34 | 4-SO2Me-phenyl | 4-pyridyl | 3-F-phenyl | 188–189 |
| 44-35 | 4-CO2H-phenyl | 4-pyridyl | 3-F-phenyl | 316–318 |
| 44-36 | 4-SOMe-phenyl | 4-pyridyl | 3-F-phenyl | 165–166 |
| 44-37 | —NHCOMe | 4-pyridyl | 4-(4-methylphenyl)cyclohexyl | 304–306 |
| 44-38 | —NHCONH-phenyl | 4-pyridyl | 4-(4-methylphenyl)cyclohexyl | 210–213 |
| 44-39 | —NHCONH-(2-Cl-phenyl) | 4-pyridyl | 3-Me-phenyl | 223–224 |
| 44-40 | —NHCONH-(3-Cl-phenyl) | 4-pyridyl | 3-Me-phenyl | 206–207 |
| 44-41 | —NHCONH-(4-Cl-phenyl) | 4-pyridyl | 3-Me-phenyl | 205–206 |
| 44-42 | —NHCONH-(2-Me-phenyl) | 4-pyridyl | 3-Me-phenyl | 227–229 |

TABLE 35

| Reference Example Compound | $R_a$ | $R_b$ | $R_c$ | m.p./° C. |
|---|---|---|---|---|
| 44-43 | —NHCONH—(3-Me-phenyl) | 4-pyridyl | 3-Me-phenyl | 190–193 |
| 44-44 | —NHCONH—(4-Me-phenyl) | 4-pyridyl | 3-Me-phenyl | 220–221 |
| 44-45 | —NHCONH—(4-CN-phenyl) | 4-pyridyl | 3-Me-phenyl | 208–210 |
| 44-46 | 4-CO$_2$H-phenyl | 4-pyridyl | 3-Me-phenyl | 335–336 |
| 44-47 | 3-CO$_2$Me-phenyl | 4-pyridyl | 3-Me-phenyl | 103–104 |
| 44-48 | benzo[1,3]dioxol-5-yl | 4-pyridyl | 3-Me-phenyl | 143–145 |
| 44-49 | 2-Me-phenyl | 4-pyridyl | 3-Me-phenyl | oil |
| 44-50 | 3-Me-phenyl | 4-pyridyl | 3-Me-phenyl | 86–87 |
| 44-51 | 4-Me-phenyl | 4-pyridyl | 3-Me-phenyl | 137–138 |

TABLE 35-continued

| Reference Example Compound | R<sub>a</sub> | R<sub>b</sub> | R<sub>c</sub> | m.p./° C. |
|---|---|---|---|---|
| 44-52 | —NH₂ | 4-pyridyl | 3,5-dichlorophenyl | 332–333 |
| 44-53 | —NHCONH-(3-methoxyphenyl) | 4-pyridyl | 3-methylphenyl | 193–194 |
| 44-54 | —NHCONH-(4-methoxyphenyl) | 4-pyridyl | 3-methylphenyl | 164–166 |
| 44-55 | —NHCONH-(2-fluorophenyl) | 4-pyridyl | 3-methylphenyl | 197–199 |

TABLE 36

| Reference Example Compound | R<sub>a</sub> | R<sub>b</sub> | R<sub>c</sub> | m.p./° C. |
|---|---|---|---|---|
| 44-56 | —NHCONH-(3-fluorophenyl) | 4-pyridyl | 3-methylphenyl | 190–192 |
| 44-57 | —NHCONH-(4-fluorophenyl) | 4-pyridyl | 3-methylphenyl | 192–194 |
| 44-58 | cyclohexyl | 4-pyridyl | 4-methoxyphenyl | 133–134 |
| 44-59 | cyclohexyl | 4-pyridyl | 4-fluorophenyl | 153–154 |

TABLE 36-continued

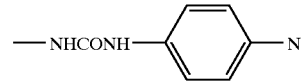

| Reference Example Compound | $R_a$ | $R_b$ | $R_c$ | m.p./° C. |
|---|---|---|---|---|
| 44-60 | —NHCONH—C₆H₄—NO₂ | 4-pyridyl | 3-methylphenyl | 158–163 |
| 44-61 | —NHCONH—C₆H₄—NMe₂ | 4-pyridyl | 3-methylphenyl | 168–170 |
| 44-62 | —NHCONH—C₆H₄(3-CO₂Et) | 4-pyridyl | 3-methylphenyl | 212–215 |
| 44-63 | —NHCONH—C₆H₄(4-CO₂Et) | 4-pyridyl | 3-methylphenyl | 203–205 |
| 44-64 | 3-chlorophenyl | 4-pyridyl | 3,5-dimethylphenyl | 131–132 |
| 44-65 | 4-chlorophenyl | 4-pyridyl | 3,5-dimethylphenyl | 152–153 |
| 44-66 | 2-chlorophenyl | 4-pyridyl | 3,5-dimethylphenyl | 123–124 |
| 44-67 | 3-pyridyl | 4-pyridyl | 3,5-dimethylphenyl | 142–144 |

TABLE 37
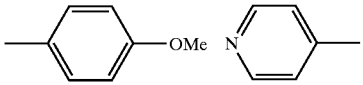
| Reference Example Compound | $R_a$ | $R_b$ | $R_c$ | m.p./° C. |
|---|---|---|---|---|
| 44-68 | 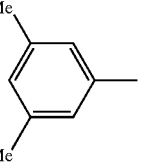 |  | 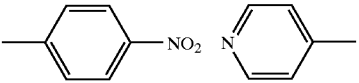 | 137–139 |
| 44-69 | 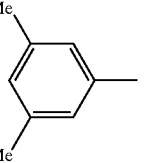 |  | 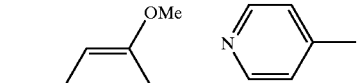 | 209–210 |
| 44-70 | 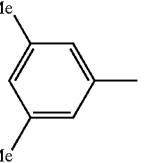 |  | 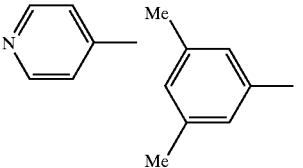 | 111–112 |
| 44-71 | —(CH$_2$)$_2$Me |  | 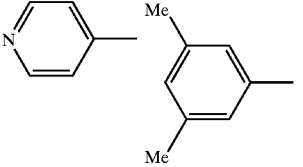 | 74–75 |
| 44-72 | —CHMe$_2$ |  | 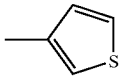 | 104–105 |
| 44-73 | 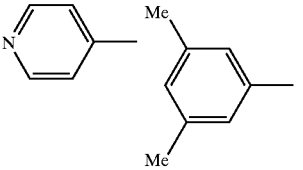 |  |  | 120–121 |
| 44-74 | —(CH$_2$)$_3$— 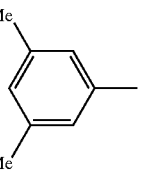 |  | | oil |

TABLE 37-continued

| Reference Example Compound | R<sub>a</sub> | R<sub>b</sub> | R<sub>c</sub> | m.p./° C. |
|---|---|---|---|---|
| 44-75 | —(CH$_2$)$_2$—phenyl | 4-pyridyl | 3,5-dimethylphenyl | oil |
| 44-76 | —(CH$_2$)$_3$Me | 4-pyridyl | 3,5-dimethylphenyl | oil |
| 44-77 | —(CH$_2$)$_4$Me | 4-pyridyl | 3,5-dimethylphenyl | oil |

TABLE 38

| Reference Example Compound | R$_a$ | R$_b$ | R$_c$ | m.p./° C. |
|---|---|---|---|---|
| 44-78 | 2-fluorophenyl | 4-pyridyl | 3,5-dimethylphenyl | 147–148 |
| 44-79 | 3-fluorophenyl | 4-pyridyl | 3,5-dimethylphenyl | 101–102 |
| 44-80 | 4-fluorophenyl | 4-pyridyl | 3,5-dimethylphenyl | 153–154 |

TABLE 38-continued

| Reference Example Compound | R_a | R_b | R_c | m.p./° C. |
|---|---|---|---|---|
| 44-81 | —NHCOMe | 4-pyridyl | 3-ethylphenyl | 253–254 |
| 44-82 | 4-(SMe)phenyl | 4-pyridyl | 3-ethylphenyl | 98–99 |
| 44-83 | —NH$_2$ | 4-pyridyl | 3-ethylphenyl | 201–202 |
| 44-84 | —NHCONH-(3-CO$_2$H-phenyl) | 4-pyridyl | 3-methylphenyl | 189–192 |
| 44-85 | —NHCONH-(4-CO$_2$H-phenyl) | 4-pyridyl | 3-methylphenyl | 217–220 |
| 44-86 | cyclohexyl | 4-pyridyl | 3,5-dimethylphenyl | 107–109 |
| 44-87 | 4-(CO$_2$Me)phenyl | 4-pyridyl | 3-chlorophenyl | 162–164 |
| 44-88 | 4-(CO$_2$H)phenyl | 4-pyridyl | 3-chlorophenyl | 332–334 |
| 44-89 | —NHCONH-phenyl | 4-pyridyl | 3,5-dichlorophenyl | 288–290 |

TABLE 39

| Reference Example Compound | $R_a$ | $R_b$ | $R_c$ | m.p./° C. |
|---|---|---|---|---|
| 44-90 | 4-(CO₂Me)phenyl | 4-pyridyl | 3-methoxy-5-methylphenyl | 130–131 |
| 44-91 | 4-(CO₂H)phenyl | 4-pyridyl | 3-methoxy-5-methylphenyl | 296–297 |
| 44-92 | 3-(CO₂H)-5-methylphenyl | 4-pyridyl | 3-methylphenyl | 251–252 |
| 44-93 | 4-(CO₂Me)phenyl | 4-pyridyl | 3,5-dimethylphenyl | 165–166 |
| 44-94 | 3-(CO₂Me)-5-methylphenyl | 4-pyridyl | 3,5-dimethylphenyl | 129–130 |
| 44-95 | 4-(CO₂H)phenyl | 4-pyridyl | 3,5-dimethylphenyl | 349–350 |
| 44-96 | 3-(CO₂H)-5-methylphenyl | 4-pyridyl | 3,5-dimethylphenyl | 269–270 |
| 44-97 | 4-(SOMe)phenyl | 4-pyridyl | 3-(MeCH₂)phenyl | 126–127 |
| 44-98 | 4-(CO₂Me)-(NHCO-)phenyl | 4-pyridyl | 3-(MeCH₂)phenyl | 290–291 |

TABLE 39-continued
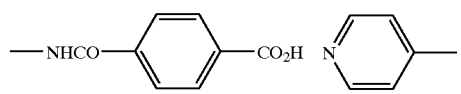
| Reference Example Compound | $R_a$ | $R_b$ | $R_c$ | m.p./° C. |
|---|---|---|---|---|
| 44-99 | —NHCO—C₆H₄—CO₂H | 4-pyridyl | 3-(MeCH₂)-phenyl | 324–326 |
| 44-100 | —NH₂ | 4-pyridyl | 3-(Me₂CH)-phenyl | 197–198 |
| 44-101 | —NHCO—C₆H₄—CN | 4-pyridyl | 3-Me-phenyl | 269–270 |
TABLE 40
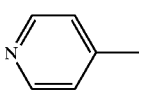
| Reference Example Compound | $R_a$ | $R_b$ | $R_c$ | m.p./° C. |
|---|---|---|---|---|
| 44-102 | —NHCO—C₆H₄—CN | 4-pyridyl | 3,5-diMe-phenyl | 315–316 |
| 44-103 | —C₆H₄—CO₂Me | 4-pyridyl | 2-Me-4-F-phenyl | 189–190 |
| 44-104 | —C₆H₄—CO₂H | 4-pyridyl | 2-Me-4-F-phenyl | 325–328 |
| 44-105 | —NH₂ | 4-pyridyl | 2-Me-4-F-phenyl | 249–251 |

TABLE 40-continued

| Reference Example Compound | $R_a$ | $R_b$ | $R_c$ | m.p./° C. |
|---|---|---|---|---|
| 44-106 | —NHCONH—C₆H₅ | 4-pyridyl | 2-Me-4-F-phenyl | 187–189 |
| 44-107 | —NHCONH—C₆H₅ | 4-pyridyl | 3-MeCH₂-phenyl | 169–171 |
| 44-108 | 4-CO₂Me-phenyl | 4-pyridyl | 3-MeCH₂-phenyl | 122–124 |
| 44-109 | —NHCONH—C₆H₅ | 4-pyridyl | 3-MeO-phenyl | 250–252 |
| 44-110 | 4-CO₂H-phenyl | 4-pyridyl | 3-MeO-phenyl | 295–296 |
| 44-111 | 4-CO₂Me-phenyl | 4-pyridyl | 3-Me₂CH-phenyl | 137–139 |
| 44-112 | 4-CO₂H-phenyl | 4-pyridyl | 3-Me₂CH-phenyl | 272–274 |
| 44-113 | —NHCONH—C₆H₅ | 4-pyridyl | 3-Me₂CH-phenyl | 170–173 |
| 44-114 | —NHCO—(4-CO₂Me-phenyl) | 4-pyridyl | 3-Me₂CH-phenyl | 299–300 |

TABLE 41

[Structure: thiazole ring with R_a at 2-position, R_b at 5-position, R_c at 4-position]

| Reference Example Compound | R_a | R_b | R_c | m.p./° C. |
|---|---|---|---|---|
| 44-115 | —NHCO—C6H4—CO2H (4-) | 4-pyridyl | Me2CH—, 3-(benzyl with methyl) | 385–387 |
| 44-116 | —NHCO—C6H4—(1H-tetrazol-5-yl) (4-) | 4-pyridyl | 3-methylphenyl (Me) | 281–285 |
| 44-117 | —NHCO—C6H4—(1H-tetrazol-5-yl) (4-) | 4-pyridyl | 3,5-dimethylphenyl | 287–290 |
| 44-118 | 4-phenylpiperazin-1-yl | 4-pyridyl | 3-methylphenyl | 120–121 |
| 44-119 | 4-phenylpiperazin-1-yl | 4-pyridyl | 3,5-dimethylphenyl | 147–148 |
| 44-120 | —CH2Me | 4-pyridyl | 3-chlorophenyl (Cl) | 87–88 |
| 44-121 | —CH2Me | 4-pyridyl | 4-chlorophenyl (Cl) | 90–91 |
| 44-122 | —CH2Me | 4-pyridyl | 4-methylphenyl (Me) | 83–84 |
| 44-123 | phenyl | 4-pyridyl | 3,5-dimethylphenyl | 118–120 |

TABLE 41-continued

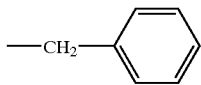

| Reference Example Compound | $R_a$ | $R_b$ | $R_c$ | m.p./° C. |
|---|---|---|---|---|
| 44-124 | —CH₂—phenyl | 4-pyridyl | 3,5-dimethylphenyl | oil |
| 44-125 | 4-(CONH₂)phenyl | 4-pyridyl | 3-methylphenyl | 266–267 |

TABLE 42

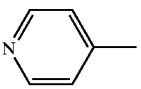

| Reference Example Compound | $R_a$ | $R_b$ | $R_c$ | m.p./° C. |
|---|---|---|---|---|
| 44-126 | 4-(1H-tetrazol-5-yl)phenyl | 4-pyridyl | 3-methylphenyl | 267–270 |
| 44-127 | 4-hydroxyphenyl | 4-pyridyl | 3-methylphenyl | 248–249 |
| 44-128 | 2,4-difluorophenyl | 4-pyridyl | 3-methylphenyl | 127–129 |
| 44-129 | 4-methylpiperazin-1-yl | 4-pyridyl | 3-methylphenyl | 154–155 |

Reference Example 44-1

4-(4-fluorophenyl)-2-phenyl-5-(4-pyridyl)-1,3-thiazole

A solution of 2-bromo-1-(4-fluorophenyl)-2-(4-pyridyl) ethanone hydrobromide (1.6 g, 4.1 mmol) and thiobenzamide (0.57 g, 4.2 mmol) in N,N-dimethylformamide (5 mL) was stirred at room temperature for 14 h. To the reaction mixture was poured aqueous sodium hydrogencarbonate solution and the precipitated solid was collected by filtration. The obtained solid was washed with water and dried. The crude crystals were recrystallized from ethyl acetate to give the title compound (0.27 g, yield 19%).

melting point: 135–137° C.

The proton nuclear magnetic resonance spectrum of the aforementioned Reference Example 44 is shown in the following Table 43.

TABLE 43

| Reference Example Compound No. | Proton Nuclear Magnetic Resonance Spectrum |
|---|---|
| 44-49 | $^1$H-NMR(CDCl$_3$)δ: 2.34(3H, s), 2.70(3H, s), 7.14–7.38(8H, m), 7.46(1H, s), 7.81(1H, ddd, J=6.6, 1.8, 1.1Hz), 8.56(2H, d, J=6.0Hz). |
| 44-74 | $^1$H-NMR(CDCl$_3$)δ: 2.04-2.26(8H, m), 2.79(2H, t, J=7.5Hz), 3.08(2H, t, J=7.6Hz), 6.97(1H, s), 7.08(2H, s), 7.17–7.35(7H, m), 8.50(2H, dd, J=4.6, 1.8Hz). |
| 44-75 | $^1$H-NMR(CDCl$_3$)δ: 2.27(6H, s), 3.13–3.23(2H, m), 3.31–3.41(2H, m), 6.98(1H, s), 7.08(2H, s), 7.19 (2H, dd, J=4.5, 1.7Hz), 7.24–7.37(5H, m), 8.50 (2H, dd, J=4.5, 1.7Hz). |
| 44-76 | $^1$H-NMR(CDCl$_3$)δ: 0.98(3H, t, J=7.3Hz), 1.43–1.55(2H, m), 1.76–1.88(2H, m), 2.26(6H, m), 3.05 (2H, t, J=7.7Hz), 6.97(1H, s), 7.08(2H, s), 7.21 (2H, dd, J=4.6, 1.8Hz), 8.50(2H, dd, J=4.6, 1.8 Hz). |
| 44-77 | $^1$H-NMR(CDCl$_3$)δ: 0.90–0.97(3H, m), 1.38–1.49(4H, m), 1.78–1.89(2H, m), 2.26(6H, s), 3.04(2H, t, J=7.9Hz), 6.97(1H, s), 7.08(2H, s), 7.21(2H, dd, J=4.5, 1.8Hz), 8.50(2H, dd, J=4.5, 1.8Hz). |
| 44-124 | $^1$H-NMR(CDCl$_3$)δ: 2.27(6H, s), 4.38(2H, s), 6.99 (1H, s), 7.10(2H, s), 7.16(2H, dd, J=4.9, 1.6Hz), 7.34–7.41(5H, m), 8.47(2H, dd, J=4.9, 1.6Hz). |

Reference Example 45

In accordance with Reference Example 21, the following Reference Example compound 45 was synthesized using pivalonitrile instead of 4-methylthiobenzonitrile. Reference Example compound 45: thiopivaloamide melting point: 117–119° C.

Reference Example 46

In accordance with the methods described in Reference Examples 8 to 12, Reference Example 44-1, JP-A-61-10580 and U.S. Pat. No. 4,612,321, Reference Example compounds 46-1 to 46-5 shown in the following Table 44 were synthesized.

TABLE 44

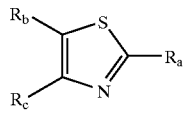

| Reference Example Compound | R$_a$ | R$_b$ | R$_c$ | m.p./° C. |
|---|---|---|---|---|
| 46-1 | —CH$_2$Me | 4-pyridyl | 3,5-dimethylphenyl | 100–101 |
| 46-2 | —CMe$_3$ | 4-pyridyl | 3-methylphenyl | 140–142 |
| 46-3 | —C$_6$H$_4$-SO$_2$Me | 4-pyridyl N-oxide | 3-methylphenyl | 196–197 |
| 46-4 | —NHCONHOMe | 4-pyridyl | 3-methylphenyl | 235–236 |

TABLE 44-continued

| Reference Example Compound | $R_a$ | $R_b$ | $R_c$ | m.p./°C. |
|---|---|---|---|---|
| 46-5 | —NHCONHO—(phenyl) | 4-pyridyl | 3-methylphenyl (Me) | 168–169 |
| 46-6 | —NH$_2$ | —NH-CH$_2$-phenyl attached to pyridyl | 4-fluorophenyl (F) | 380–381 |
| 46-7 | —NHCO—(3-pyridyl) | —NH-CH$_2$-phenyl attached to pyridyl | 3-methylphenyl (Me) | 220–222 |

Example 1

| | |
|---|---|
| (1) Reference Example compound 23-313 | 10.0 mg |
| (2) lactose | 60.0 mg |
| (3) cornstarch | 35.0 mg |
| (4) gelatin | 3.0 mg |
| (5) magnesium stearate | 2.0 mg |

A mixture of Reference Example compound 23-313 (10.0 mg), lactose (60.0 mg) and cornstarch (35.0 mg) is granulated using 10% aqueous gelatin solution (0.03 ml, 3.0 mg as gelatin) and passing through a 1 mm mesh sieve. The granules are dried at 40° C. and passed through the sieve again. The granules thus obtained are mixed with magnesium stearate (2.0 mg) and compressed. The obtained core tablet is coated with sugar coating made of an aqueous suspension of sucrose, titanium dioxide, talc and gum arabic. The coated tablet is polished with bee wax to give a coated tablet.

Example 2

| | |
|---|---|
| (1) Reference Example compound 23-313 | 10.0 mg |
| (2) lactose | 70.0 mg |
| (3) cornstarch | 50.0 mg |
| (4) soluble starch | 7.0 mg |
| (5) magnesium stearate | 3.0 mg |

Reference Example compound 23-313 (10.0 mg) and magnesium stearate (3.0 mg) are granulated using an aqueous solution (0.07 ml) of soluble starch (7.0 mg as soluble starch), dried and mixed with lactose (70.0 mg) and cornstarch (50.0 mg). The mixture is compressed to give tablets.

Example 3

| | |
|---|---|
| (1) Reference Example compound 23-313 | 5.0 mg |
| (2) sodium chloride | 20.0 mg |
| (3) distilled water to total | 2 ml |

Reference Example compound 23-313 (5.0 mg) and sodium chloride (20.0 mg) are dissolved in distilled water and water is added to make the total amount 2.0 ml. The solution is filtrated and aseptically filled in a 2 ml ampoule. The ampoule is sterilized and sealed to give a solution for injection.

Example 4

| | |
|---|---|
| (1) Reference Example compound 23-331 | 10.0 mg |
| (2) lactose | 60.0 mg |
| (3) cornstarch | 35.0 mg |
| (4) gelatin | 3.0 mg |
| (5) magnesium stearate | 2.0 mg |

A mixture of Reference Example compound 23-331 (10.0 mg), lactose (60.0 mg) and cornstarch (35.0 mg) is granulated using 10% aqueous gelatin solution (0.03 ml, 3.0 mg as gelatin) and passing through a 1 mm mesh sieve. The granules are dried at 40° C. and passed through the sieve again. The granules thus obtained are mixed with magnesium stearate (2.0 mg) and compressed. The obtained core tablet is coated with sugar coating made of an aqueous suspension of sucrose, titanium dioxide, talc and gum arabic. The coated tablet is polished with bee wax to give a coated tablet.

Example 5

| | |
|---|---|
| (1) Reference Example compound 23-331 | 10.0 mg |
| (2) lactose | 70.0 mg |
| (3) cornstarch | 50.0 mg |
| (4) soluble starch | 7.0 mg |
| (5) magnesium stearate | 3.0 mg |

Reference Example compound 23-331 (10.0 mg) and magnesium stearate (3.0 mg) are granulated using an aqueous solution (0.07 ml) of soluble starch (7.0 mg as soluble starch), dried and mixed with lactose (70.0 mg) and cornstarch (50.0 mg). The mixture is compressed to give tablets.

Example 6

| | |
|---|---|
| (1) Reference Example compound 23-331 | 5.0 mg |
| (2) sodium chloride | 20.0 mg |
| (3) distilled water to total | 2 ml |

Reference Example compound 23-331 (5.0 mg) and sodium chloride (20.0 mg) are dissolved in distilled water and water is added to make the total 2.0 ml. The solution is aseptically filtered and filled into a 2 ml ampoule. The ampoule is sterilized and sealed to give a solution for injection.

Experimental Example 1

The genetic manipulations described below were according to a method described in the book (Maniatis et al., Molecular Cloning, Cold Spring Harbor Laboratory, 1989) or methods described in the protocols attached to the reagents.

(1) Cloning of Human p38 MAP Kinase Gene and Preparation of Recombinant Baculovirus Cloning of human p38 MAP kinase gene was performed by a PCR method using a primer set P38-U: 5'-ACCACTCGAGATGGACTACAAGGACGACGATG ACAAGTCTCAGGAGAGGCCCACGTTCTACC-3' [SEQ ID NO:1] and PAG-L: 5'-ACCCGGTACCACCAGGTGCTCAGGACTCCATCTCT-3' [SEQ ID NO:2] made by the use of kidney cDNA (Toyobo, QUICK-Clone cDNA) as a template and referring to the base sequence of p38 MAP kinase gene reported by Han et al. (Science 265 (5173), 808–811 (1994)).

A PCR reaction was performed by a Hot Start method using AmpliWax PCR Gem 100 (Takara Shuzo). As the lower mixed solution, 2 µL 10×LA PCR Buffer, 3 µL 2.5 mM dNTP solution, each 2.5 µL of 12.5 µm primer solutions, and 10 µL sterile distilled water were mixed. As the upper mixed solution, 1 µL human cardiac cDNA (1 ng/mL) as a template, 3 µL 10×LA PCR Buffer, 1 µL 2.5 mM dNTP solution, 0.5 µL TaKaRa LA Taq DNA polymerase (Takara Shuzo)., and 24.5 µL sterile distilled water were mixed. one Ampliwax PCR Gem 100 (Takara Shuzo) was added to the prepared lower mixed solution and the mixture was treated at 70° C. for 5 min and for 5 min in an ice and, thereafter, the upper mixed solution was added to prepare a reaction solution for PCR. A tube containing the reaction solution was set at a thermal cycler (Perkin Elmer), which was treated at 95° C. for 2 min. Further, after repeating 35 times a cycle of 15 seconds at 95° C. and 2 minutes at 68° C., treatment was performed at 72° C. for 8 minutes. The resulting PCR product was subjected to agarose gel (1%) electrophoresis, 1.1 kb DNA fragment containing p38 MAP kinase gene was recovered from the gel and, thereafter, which was inserted into pT7Blue-T vector (Takara Shuzo) to make the plasmid pHP38.

The 4.8 kb XhoI-KpnI fragment of the plasmid pFAST-BAC1 (CIBCOBRL) and the 1.1 kb XhoI-Kpn fragment of the above plasmid pHP38 were ligated to make the plasmid pFBHP38.

The plasmid pFBHP38 and BAC-TO-BAC Baculovirus Expression System (GIBCOBRL) were used to prepare the recombinant baculovirus virusstock BAC-HP38.

(2) Cloning of Human MKK3 Gene and Preparation of Recombinant Baculovirus

Cloning of human MKK3 gene was performed by a PCR method using a primer set MKK-U: 5'-ACAAGAATTCATAACATATGGCTCATCATCATC ATCATCATTCCAAGCCACCCGCACCCAA-3' [SEQ ID NO:3] and MKK-L: 5'-TCCCGTCTAGACTATGAGTCTTCTCCCAGGAT-3' [SEQ ID NO:4] made by the use of kidney cDNA (Toyobo, QUICK-Clone cDNA) as a template and referring to the base sequence of MKK3 gene reported by Derijard, B. et al., Science 267 (5198), 682–685 (1995).

A PCR reaction was performed by a Hot Start method using AmpliWax PCR Gem 100 (Takara Shuzo). As the lower mixed solution, 2 µL 10×LA PCR Buffer, 3 µL 2.5 mM dNTP solution, each 2.5 µL of 12.5 µM primer solutions, and 10 µL sterile distilled water were mixed. As the upper mixed solution, 1 µL human kidney cDNA (1 ng/mL) as a template, 3 µL 10×LA PCR Buffer, 1 µL 2.5 mM dNTP solution, 0.5 µL TaKaRa LA Taq DNA polymerase (Takara Shuzo) and 24.5 µL sterile distilled water were mixed. One AmpliWax PCR Gem 100 (Takara Shuzo) was added to the prepared lower mixed solution and the mixture was treated at 70° C. for 5 minutes and for 5 minutes in an ice and, thereafter, the upper mixed solution was added to prepare a reaction solution for PCR. A tube containing the reaction solution was set at a thermal cycler (Perkin Elmer), which was treated at 95° C. for 2 minutes. Further, after repeating 35 times a cycle of 15 seconds at 95° C. and 2 minutes at 68° C., treatment was performed at 72° C. for 8 minutes. The resulting PCR product was subjected to agarose gel (1%) electrophoresis, 1.0 kb DNA fragment containing MKK3 gene was recovered from the gel and, thereafter, which was inserted into pT7Blue-T vector (Takara Shuzo) to make the plasmid pHMKK3.

In order to mutate MKK3 into a constitutive active form (from Ser to Glu at 189 position, from Thr to Glu at position 193), a primer set SER-U: 5'-GGCTACTTGGTGGACGAGGTGGCCAAGGAGAT GGATGCCGGCTGC-3' [SEQ ID NO:5] and SER-L: 5'-GCAGCCGGCATCCATCTCCTTGGCCACCTCGTC CACCAAGTAGCC-3' [SEQ ID NO:6] was used to introduce a mutation by QuikChange Site-Directed Mutagenesis Kit (Stratagene), to obtain pFBcaMKK3.

4.8 kb EcoRI-XbaI fragment of the plasmid pFASTBAC1 (CIBCOBRL) and the 1.0 kb EcoRI-XbaI fragment of the above plasmid pcaMKK 3 were ligated to make the plasmid pFBcaMKK3.

The plasmid pFBcaMKK3 and BAC-TO-BAC Baculovirus Expression System (GIBCOBRL) were used to prepare the recombinant baculovirus virusstock BAC-caMKK3.

(3) Preparation of Active Form p38 MAP Kinase

The Sf-21 cells were seeded on 100 mL Sf-900II SFM medium (GIBCOBRL) to 1×10⁶ cells/mL and cultured at 27° C. for 24 hours. After each 0.2 mL of the virusstock BAC-HP38 and BAC-caMKK3 of recombinant baculovirus were added, the culturing was further performed for 48 hours. After the cells were separated from the culturing solution by centrifugation (3000 rpm, 10 min), the cells were washed twice with PBS. After the cells were suspended in 10 ml Lysis buffer (25 mM HEPES (pH 7.5), 1% Triton X, 130 mM NaCl, 1 mM EDTA, 1 mM DTT, 25 mM β-glycerophosphate, 20 mM leupeptin, 1 mM APMSF, 1 mM Sodium orthovanadate), the cells were lysed by treating twice in a homogenizer (POLYTRON) at 20000 rpm for 2 minutes. From the supernatant obtained by centrifugation (40000 rpm, 45 minutes), active form p38 MAP kinase was purified using Anti-FLAG M2 Affinity Gel (Eastman Chemical).

(4) Measurement of the Enzyme Inhibitory Activity 2.5 μL of a test compound dissolved in DMSO was added to 37.5 μL reaction solution (25 mM HEPES (pH 7.5), 10 mM Magnesium Acetate) containing 260 ng active form p38 MAP kinase and 1 μg Myelin Basic Protein, which was maintained at 30° C. for 5 minutes. The reaction was initiated by adding 10 μL ATP solution (2.5 μM ATP, 0.1 μCi [g-$^{32}$P]ATP). After the reaction was performed at 30° C. for 60 minutes, the reaction was stopped by adding 50 μL 20% TCA solution. After the reaction solution was allowed to stand at 0° C. for 20 minutes, an acid insoluble fraction was transferred to GF/C filter (Packard Japan) using Cell Harvester (Packard Japan) and washed with 250 mM $H_3PO_4$. After drying at 45° C. for 60 minutes, 40 μL Microscint 0 (Packard Japan) was added and the radioactivity was measured with a Topcount (Packard Japan). The concentration ($IC_{50}$ value) of the test compound necessary for inhibiting uptake of $^{32}$P into an acid insoluble fraction by 50% was calculated with PRISM 2.01 (Graphpad Software). The results are shown in Table 45.

TABLE 45

| Reference Example Compound No. | $IC_{50}$ (μM) |
|---|---|
| 13-14 | 0.086 |
| 13-15 | 0.081 |
| 13-16 | 0.060 |
| 13-70 | 0.026 |
| 13-74 | 0.63 |

Experimental Example 2

Measurement of inhibiting activity of TNF-α production

After THP-1 cells which had been cultured on PRMI 1640 medium (manufactured by Life Technologies, Inc.) containing 1% inactivated bovine fetal serum (manufactured by Life Technologies, Inc., U.S.A.) and 10 mM HEPES (pH 7.5) seeded on a 96-well plate to 1×10$^5$ cells/well, 1 μL test compound dissolved in DMSO was added. After incubation at 37° C. for 1 hour in a $CO_2$ incubator, LPS (Wako Pure Chemicals) was added to the final concentration 5 μg/mL. After cultured at 37° C. for 4 hours in a $CO_2$ incubator, the supernatant was obtained by centrifugation. The concentration of TNF-α in the supernatant was measured by ELISA (R&D Systems, Quantikine Kit). The concentration ($IC_{50}$ value) of the test compound necessary for inhibiting TNF-α production by 50% was calculated using PRIMS 2.01 (Graphpad Software). The results are shown in Table 46.

TABLE 46

| Reference Example Compound No. | $IC_{50}$ (μM) |
|---|---|
| 13-16 | 0.14 |
| 13-70 | 0.18 |
| 23-60 | 0.046 |

From the above results, it can be seen that Compound (I) has an excellent inhibitory activity against p38 MAP kinase and TNF-α production.

Industrial Applicability

Compound (I) has an excellent p38 MAP kinase inhibitory activity and TNF-α inhibitory activity and can be used as a prophylactic and therapeutic agent for cytokine-mediated diseases, such as p38 MAP kinase related diseases, TNF-α related diseases and the like.

What is claimed is:

1. A method for treatment of cerebral hemorrhage, cerebral infarction, head trauma, spinal cord injury, brain edema, multiple sclerosis, Alzheimer's disease, Parkinson's disease, amyotrophic lateral sclerosis, diabetes, osteoporosis, Creutzfeldt-Jakob disease or virus infection, comprising administering an effective amount of a 1,3-thiazole compound to a mammal, wherein the 1,3-thiazole compound is a compound of the formula

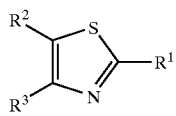

wherein $R^1$ represents a hydrocarbon group optionally having substituent(s) selected from the group consisting $C_{1-6}$ alkyl, $C_{2-6}$ alkenyl, $C_{2-6}$ alknyl, $C_{3-6}$ cycloalkyl, and $C_{6-14}$ aryl;

$R^2$ represents a pyridyl group optionally having substituent(s); and $R^3$ represents a $C_{6-14}$ monocyclic or fused polycyclic aromatic hydrocarbon group optionally having substituent(s), or a salt thereof.

2. The method of claim 1, wherein $R^1$ is a $C_{1-10}$ alkyl group, a $C_{2-6}$ alkenyl group, a $C_{2-6}$ alkynyl group, a $C_{3-6}$ cycloalkyl group, a $C_{6-14}$ aryl group or a $C_{7-16}$ aralkyl group which groups may have substituent(s) selected from the group consisting of $C_{1-6}$ alkyl, $C_{2-6}$ alkenyl, $C_{2-6}$ alkynyl, $C_{3-6}$ cycloalkyl, and $C_{6-14}$ aryl;

$R^2$ represents a pyridyl group optionally having substituent(s) selected from the group consisting of oxo, halogen atom, $C_{1-3}$ alkylenedioxy, nitro, cyano, optionally halogenated $C_{1-6}$ alkyl, optionally halogenated $C_{2-6}$ alkenyl, carboxy $C_{2-6}$ alkenyl, optionally halogenated $C_{2-6}$ alkynyl, optionally halogenated $C_{3-6}$ cycloalkyl, $C_{6-14}$ aryl, optionally halogenated $C_{1-8}$ alkoxy, $C_{1-6}$ alkoxy-carbonyl-$C_{1-6}$ alkoxy, hydroxy, $C_{6-14}$ aryloxy, $C_{7-16}$ aralkyloxy, mercapto, optionally halogenated $C_{1-6}$ alkylthio, $C_{6-14}$ arylthio, $C_{7-16}$ aralkylthio, amino, mono-$C_{1-6}$ alkylamino, mono-$C_{6-14}$ arylamino, di-$C_{1-6}$ alkylamino, di-$C_{6-14}$ arylamino, formyl, carboxy, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5 or 6 membered heterocyclic carbonyl, carbamoyl, thiocarbamoyl, mono-$C_{1-6}$ alkyl-carbamoyl, di-$C_{1-6}$ alkyl-carbamoyl, $C_{6-14}$ aryl-carbamoyl, 5 or 6 membered heterocyclic carbamoyl, $C_{1-6}$ alkylsulfonyl, $C_{6-14}$ arylsulfonyl, $C_{1-6}$ alkylsulfinyl, $C_{6-14}$ arylsulfinyl, formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino, $C_{6-14}$ arylsulfonylamino, $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy, nicotinoyloxy, 5 to 7 membered saturated cyclic amino optionally having 1 to 4 of one or two kinds of heteroatom(s) selected from a nitrogen atom, a sulfur atom and an oxygen atom in addition to one nitrogen atom and carbon atoms wherein the cyclic amino may have substituents selected from the group consisting of $C_{1-6}$ alkyl, $C_{6-14}$ aryl, $C_{1-6}$ alkyl-carbonyl, 5 to 10 membered aromatic heterocyclic group and oxo; and 5 to 10 membered aromatic heterocyclic group containing 1 to 4 of one or two kinds of heteroatom(s) selected from a nitrogen atom, a sulfur atom and an oxygen atom in addition to carbon atoms, sulfo, sulfamoyl, sulfinamoyl and sulfenamoyl; and $R^3$ represents a $C_{6-14}$ monocyclic or fused polycyclic aromatic hydrocarbon group optionally having substituents selected from the group consisting of oxo, halogen atom, $C_{1-3}$ alkylenedioxy, nitro, cyano, optionally halogenated $C_{1-6}$ alkyl, optionally halogenated $C_{2-6}$ alkenyl, carboxy $C_{2-6}$ alkenyl, optionally halogenated $C_{2-6}$ alkynyl, optionally halogenated $C_{3-6}$ cycloalkyl, $C_{6-14}$ aryl, optionally halogenated $C_{1-6}$ alkoxy, $C_{1-6}$ alkoxy-carbonyl-$C_{1-6}$ alkoxy, hydroxy, $C_{6-14}$ aryloxy, $C_{7-16}$ aralkyloxy, mercapto, optionally halogenated $C_{1-6}$ alkylthio, $C_{6-14}$ arylthio, $C_{7-16}$ aralkylthio, amino, mono-$C_{1-6}$ alkylamino, mono-$C_{6-14}$ arylamino, di-$C_{1-6}$ alkylamino, di-$C_{6-14}$ arylamino, formyl, carboxy, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5 or 6 membered heterocyclic carbonyl, carbamoyl, thiocarbamoyl, mono-$C_{1-6}$ alkyl-carbamoyl, di-$C_{1-6}$ alkyl-carbamoyl, $C_{6-14}$ aryl-carbamoyl, 5 or 6 membered heterocyclic carbamoyl, $C_{1-6}$ alkylsulfonyl, $C_{6-14}$ arylsulfonyl, $C_{1-6}$ alkylsulfinyl, $C_{6-14}$ arylsulfinyl, formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino, $C_{6-14}$ arylsulfonylamino, $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy, and nicotinoyloxy.

3. The method of claim 1, wherein $R^1$ is (a) a $C_{6-14}$ aryl group optionally having 1 to 5 $C_{1-6}$ alkyl substiluent(s), (b) $C_{1-8}$ alkyl group optionally having 1 to 5 $C_{1-6}$ alkyl substituent(s), (c) $C_{3-6}$ cycloalkyl group optionally having 1 to 5 $C_{1-6}$ alkyl substituent(s), or (d) $C_{7-16}$ aralkyl group.

4. The method of claim 1, wherein $R^1$ is a $C_{6-14}$ aryl group.

5. The method of claim 1, wherein $R^2$ is a 4-pyridyl group optionally having substituent(s).

6. The method of claim 1, wherein $R^1$ is a $C_{6-10}$ aryl group optionally having substituent(s).

7. The method of claim 1, wherein $R^3$ is a phenyl group optionally having substituent(s).

8. The method of claim 1, wherein $R^3$ is a $C_{6-14}$ aryl group optionally having substituent(s) selected from the group consisting of halogen atom, $C_{1-3}$ alkylenedioxy, optionally halogenated $C_{1-6}$ alkyl, carboxy $C_{2-6}$ alkenyl, optionally halogenated $C_{1-8}$ alkoxy, carboxy $C_{1-8}$ alkoxy, hydroxy, $C_{6-14}$ aryloxy, $C_{1-6}$ alkoxy-carbonyl, $C_{1-6}$ alkyl-carbonyloxy, mono- or di-$C_{1-6}$ alkylamino and $C_{1-6}$ alkoxy-carbonyl-$C_{1-6}$ alkoxy.

9. The method of claim 1, wherein $R^3$ is a phenyl group optionally having substituent(s) selected from the group consisting of halogen atom and $C_{1-6}$ alkyl group.

10. The method of claim 1, wherein $R^1$ is (a) $C_{6-14}$ aryl group or (b) $C_{1-6}$ alkyl group, $R^2$ is a pyridyl group, and $R^3$ is a $C_{6-14}$ aryl group optionally having 1 to 5 substituent(s) selected from halogen atom, optionally halogenated $C_{1-6}$ alkyl, optionally halogenated $C_{1-6}$ alkoxy and carboxy.

11. The method of claim 1, wherein $R^1$ is $C_{1-8}$ alkyl, $C_{3-6}$ cycloalkyl or $C_{6-14}$ aryl optionally having 1 to 5 $C_{1-6}$ alkyl substituent(s)

$R^2$ is a pyridyl group; and $R^3$ is a $C_{6-10}$ aryl group optionally having 1 to 3 substituent(s) selected from halogen atom, $C_{1-3}$ alkylenedioxy, optionally halogenated $C_{1-6}$ alkyl, carboxy $C_{2-6}$ alkenyl, optionally halogenated $C_{1-8}$ alkoxy, hydroxy $C_{7-16}$ aralkyloxy and $C_{1-6}$ alkyl-carbonyloxy.

12. The method of claim 1, wherein $R^1$ is a $C_{6-14}$ aryl group, $R^2$ is a pyridyl group, and $R^3$ is a $C_{6-14}$ aryl group optionally having halogen atom(s).

* * * * *

SEQUENCE LISTING

<160> NUMBER OF SEQ ID NOS: 6

<210> SEQ ID NO 1
<211> LENGTH: 62
<212> TYPE: DNA
<213> ORGANISM: Artificial Sequence
<220> FEATURE:
<223> OTHER INFORMATION: Description of Artificial Sequence - DNA PRIMER

<400> SEQUENCE: 1
accactcgag atggactaca aggacgacga tgacaagtct caggagaggc ccacgttcta     60
cc                                                                    62

<210> SEQ ID NO 2

```
<211> LENGTH: 35
<212> TYPE: DNA
<213> ORGANISM: Artificial Sequence
<220> FEATURE:
<223> OTHER INFORMATION: Description of Artificial Sequence - DNA PRIMER

<400> SEQUENCE: 2
acccggtacc accaggtgct caggactcca tctct                              35

<210> SEQ ID NO 3
<211> LENGTH: 61
<212> TYPE: DNA
<213> ORGANISM: Artificial Sequence
<220> FEATURE:
<223> OTHER INFORMATION: Description of Artificial Sequence - DNA PRIMER

<400> SEQUENCE: 3
acaagaattc ataacatatg gctcatcatc atcatcatca ttccaagcca cccgcaccca    60
a                                                                   61

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence - DNA PRIMER

<400> SEQUENCE: 4
tcccgtctag actatgagtc ttctcccagg at                                 32

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence - DNA PRIMER

<400> SEQUENCE: 5
ggctacttgg tggacgaggt ggccaaggag atggatgccg gctgc                   45

<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence - DNA PRIMER

<400> SEQUENCE: 6
gcagccggca tccatctcct tggccacctc gtccaccaag tagcc                   45
```